US006794167B2

(12) United States Patent
Parales et al.

(10) Patent No.: US 6,794,167 B2
(45) Date of Patent: Sep. 21, 2004

(54) MODIFIED NAPHTHALENE DIOXYGENASES AND METHODS OF USE

(75) Inventors: Rebecca Parales, Iowa City, IA (US); David Gibson, Iowa City, IA (US); Sol Resnick, Encinitas, CA (US); Kyoung Lee, Kyongnam (KR)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/843,250

(22) Filed: Apr. 26, 2001

(65) Prior Publication Data

US 2003/0022335 A1 Jan. 30, 2003

Related U.S. Application Data

(63) Continuation of application No. PCT/US99/25079, filed on Oct. 26, 1999.
(60) Provisional application No. 60/105,575, filed on Oct. 26, 1998.

(51) Int. Cl.$^{7}$ .............................. C12N 9/02; C12P 7/00; C12P 7/02; C12Q 1/26; C07K 17/00
(52) U.S. Cl. ........................ 435/189; 435/25; 435/132; 435/155; 435/156; 530/350
(58) Field of Search ......................... 435/189, 25, 132, 435/155, 156; 530/350

(56) References Cited

U.S. PATENT DOCUMENTS

| 4,476,296 A | 10/1984 | Ballard et al. ............... 528/481 |
| 4,508,822 A | 4/1985 | Taylor ......................... 435/155 |
| 4,548,737 A | 10/1985 | Ballard et al. ............... 252/500 |
| 4,876,200 A | 10/1989 | Schofield et al. ......... 435/253.3 |
| 5,470,728 A | 11/1995 | Grund ......................... 435/156 |

FOREIGN PATENT DOCUMENTS

| EP | 0076606 | 4/1983 | ............. C12P/7/02 |
| EP | 0125767 | 11/1984 | ........... H01L/23/30 |
| EP | 0154162 | 9/1985 | ............. C08F/8/00 |
| EP | 0336719 | 10/1989 | ........... C12N/15/00 |
| WO | 93/09240 | 5/1993 | ............. C12P/7/22 |
| WO | 93/09241 | 5/1993 | ............. C12P/7/22 |

OTHER PUBLICATIONS

Mondello et al. , Applied and Environmental Microbiology 63(8):3096–3103, Aug. 1997.*
Jiang et al. , J. Bacteriol. 178(11):3133–3139, 1996.*
Bork , Genome Research, 10:398–400, 2000.*
Seffernick et al. , J. Bacteriol. 183(8):2405–2410, 2001.*
Broun et al., Science 282:1315–1317, 1998.*
Witkowski et al. , Biochemistry 38:11643–11650, 1999.*
Brown, S.M., et al., "The Use of Arene–cis–Diols in Synthesis", In: Organic Synthesis: Theory and Applications, 2, pp. 113–176, (1993).

Carless, H.A., et al., "The Use of Cyclohexa–3,5–Diene–1, 2–Diols in Enantiospecific Synthesis", Tetrahedron: Asymmetry Report No. 9, v. 3 (7), pp. 795–826, (1992).
Denome, S., et al., "Metabolism of dibenzophiophene and naphthalene in pseudomonas strains: complete DNA sequence of an upper naphthalene catabolic pathway", J. Bacteriol., 175 (21), Accession No. AAA16131, Databse GenBank, 6890–6901, (Apr. 26, 1993).
Denome, S., et al., "Metabolism of dibenzothiopene and naphthalene in Pesudomas Strains: complete DNA sequence of an upper naphthalene catabolix pathway", J. Bacteriol., 175 (21), Accession No. AA16125, Database GenBank, 6890–6901, (Jun. 12, 1993).
Denome, S., et al., "Metabolism of dibenzothiophene and naphthalene in pseudomonas strains: complete DNA sequence of an upper naphthalene catabolic pathway", J. Bacteriol., 175 (21), Accession No. AAA16129, Database GenBank, 6890–6901, (Jun. 12, 1993).
Denome, S., et al., "Metabolism of dibenzothiophene and naphthalene in pseudomonas strains: complete DNA sequence of an upper naphthalene catabolic pathway", J. Bacteriol., 175 (26), Accession No. AAA16130, Database GenBank, 6890–6901, (Jun. 12, 1993).
Fuenmayor, S., et al., "Pseudomonas sp. U2", Accession No. AAD12619 Database GenBank, 1, (Feb. 4, 1999).
Hudlicky, T., et al., "An Evolutionary Perspective of Microbial Oxidations of Aromatic Compounds in Enantioselective Synthesis: History, Current Status, and Perspectives", In: Advances in Asymmetric Synthesis, 1, pp. 271–312, (1995).
Jerina, D.M., et al., "Cis–1, 2–Dihydroxy–1, 2–Dihydronaphthalene: A Bacterial Metabolite from Naphthalene", Archives of Biochemistry and Biophysics, 142, pp. 394–396, (1971).
Kauppi, B., et al., "Structure of an aromatic–ring–hydroxylating dioxygenase—naphthalene 1,2–dioxygenase", Structure, 6 (5), pp. 571–586, (1998).
Klecka, G.M., et al., "Metabolism of Dibenzo [1,4]dioxan by a Pseudomonas Species", The Biochemical Journal, 180 (3), pp. 639–645, (1979).

(List continued on next page.)

Primary Examiner—Rebecca E. Prouty
Assistant Examiner—Delia Ramirez
(74) Attorney, Agent, or Firm—Schwegman, Lundberg, Woessner & Kluth, P.A.

(57) ABSTRACT

The invention provides an NDO or NDO related complex comprising at least one alpha-subunit polypeptide that comprises: 1) a substituted amino acid at the position corresponding to position 352 in NDO, 2) a substituted amino acid at the position corresponding to position 201, 202, 260, 316, 351, 358, 362, or 366 in NDO, or 3) a substituted amino acid at the position corresponding to position 352 in NDO, and a substituted amino acid at the position corresponding to position 201, 202, 260, 316, 351, 358, 362, or 366 in NDO; or a catalytically active fragment thereof. The invention also provides DNA encoding such polypeptides, host cells augmented by such DNA, and methods for using the enzymes or host cells to provide useful and novel synthons. The invention also provides novel compounds prepared with the complexes or methods of the invention.

15 Claims, 2 Drawing Sheets

OTHER PUBLICATIONS

Kolb, H.C., et al., "Catalytic Asymmetric Dihydroxylation", *Chem. Rev., 94*, pp. 2483–2494, 2503–2515, 2526–2527, 2530–2531, and 2538–2541, (1994).

Ley, S.V., "Stereoselective synthesis of inositol phosphates", *Pure & App. Chem., 62* (*10*), pp. 2031–2034, (1990).

Resnick, S.M., et al. "Diverse reactions catalyzed by naphthalene dioxygenase from Pseudomonas sp strain NCIB 9816", *Journal of Industrial Microbiology, 17*, pp. 438–457, (1996).

Ribbons, D.W., et al., "Biodegradations Yield Novel Intermediates for Chemical Synthesis", *In: Advances in Applied Biotechnology Series, vol. 4, Biotechnology and Biodegradation*, D. Kamely, et al., (Eds), The Portfolio Publishing Company, The Woodlands, TX, pp. 213–245, (1990).

Sheldrake, G.N., "Chapter 6: Biologically Derived Arene cis–Dihydrodiols as Synthetic Building Blocks", *In: Chirality in Industry*, A.N. Collins, et al., (Eds.), John Wiley & Sons, Ltd., pp. 127–166, (1992).

Torok, D.S., et al., "Desaturation and Oxygenation of 1,2–Dihydronaphthalene by Toulene and Naphthalene Dioxygenase", *Journal of Bacteriology, 177* (*20*), pp. 5799–5805, (Oct. 1995).

Wackett, L.P., et al., "Benzylic Monooxygenation Catalyzed by Toluene Dioxygenase from Pseudomonas putida", *Biochemistry, 27*, pp. 1360–1367, (1988).

Widdowson, D.A., et al., "The Use of Substituted Cyclohexadiene Diols As Versatile Chiral Synthons", *Janssen, Chimica Acta, 8* (*3*), pp. 3–9, (1990).

* cited by examiner-

SEQUENCE LISTING

<160> NUMBER OF SEQ ID NOS: 65

<210> SEQ ID NO 1
<211> LENGTH: 2265
<212> TYPE: DNA
<213> ORGANISM: Artificial Sequence
<220> FEATURE:
<223> OTHER INFORMATION: A sequence encoding an NDO mutant.

<400> SEQUENCE: 1

```
gagggtagag aaatcgaatg cccccttgcat caaggtcggt ttgacgtttg cacaggcaaa        60
gccctgtgcg cacccgtgac acagaacatc aaaacatatc cagtcaagat tgagaacctg       120
cgcgtaatga ttgatttgag ctaagaattt taacaggagg caccccgggc cctagagcgt       180
aatcaccccc attccatctt ttttaggtga aacatgaat tacaataata aatcttggt         240
aagtgaatct ggtctgagcc aaaagcacct gattcatggc gatgaagaac ttttccaaca       300
tgaactgaaa accattttg cgcggaactg cttttctc actcatgata gcctgattcc         360
tgccccggc gactatgtta ccgcaaaaat ggggattgac gaggtcatcg tctcccggca       420
gaacgacggt tcgattcgtg cttttctgaa cgtttgccgg catcgtggca agacgctggt       480
gagcgtggaa gccggcaatg ccaaggtttt tgtttgcagc tatcacggct ggggcttcgg       540
ctccaacggt gaactgcaga gcgttccatt tgaaaaagat ctgtacggcg agtcgctcaa       600
taaaaaatgt ctggggttga agaagtcgc tcgcgtggag agcttccatg gcttcatcta       660
cggttgcttc gaccaggagg cccctcctct tatggactat ctgggtgacg ctgcttggta       720
cctggaacct atgttcaagc attccggcgg tttagaactg gtcggtcctc caggcaaggt       780
tgtgatcaag gccaactgga aggcaccccgc ggaaaacttt gtgggagatg cataccacgt      840
gggttggacg cacgcgtctt cgcttcgctc ggggagtct atcttctcgt cgctcgctgg       900
caatgcggcg ctaccacctg aaggcgcagg cttgcaaatg acctccaaat acggcagcgg       960
catgggtgtg ttgtgggacg atattcagg tgtgcatagc gcagacttgg ttccggaatt      1020
gatggcattc ggaggcgcaa agcaggaaag gctgaacaaa gaaattggcg atgttcgcgc      1080
tcggatttat cgcagccacc tcaactgcac cgttttcccg aacaacagca tgctgacctg      1140
ctcgggtgtt ttcaaagtat ggaacccgat cgacgcaaac accaccgagg tctgaccta      1200
cgccattgtc gaaaaagaca tgcctgagga tctcaagcgc cgcttggccg actctgttca      1260
gcgaacggtc gggcctgctg gcttctggga aagcgacgac aatgacaata tggaaacagc      1320
ttcgcaaaac ggcaagaaat atcaatcaag agatagtgat ctgcttcaa accttggttt      1380
cggtgaggac gtatacggcg acgcggtcta tccaggcgtc gtcggcaaat cggcgatcgg      1440
cgagaccagt tatcgtggtt tctaccgggc ttaccaggca cacgtcagca gctccaactg      1500
ggctgagttc gagcatgcct ctagtacttg gcatactgaa cttacgaaga ctactgatcg      1560
ctaacagacg agtcgaccat gatgatcaat attcaagaag acaagctggt ttccgcccac      1620
gacgccgaaa agattcttcg ttttcttcaat tgccacgact ctgctttgca caagaagcc      1680
actacgctgc tgacccagga agcgcatttg ttggacattc aggcttaccg tgcttggtta      1740
gagcactgcg tggggtcaga ggtgcaatat caggtcattt cacgcgaact gcgcgcagct      1800
tcagagcgtc gttataagct caatgaagcc atgaacgttt acaacgaaaa ttttcagcaa      1860
ctgaaagttc gagttgagca tcaactggat ccgcaaaact ggggcaacag cccgaagctg      1920
cgctttactc gctttatcac caacgtccag gccgcaatgg acgtaaatga caaagagcta      1980
cttcacatcc gctccaacgt cattctgcac cgggcacgac gtggcaatca ggtcgatgtc      2040
ttctacgccg cccgggaaga taatggaaa cgtggcgaag gtggagtacg aaaattggtc      2100
cagcgattcg tcgattaccc agagcgcata cttcagacgc acaatctgat ggtctttctg      2160
tgattcagtg accatttta caaatggtca ctgcaaccgc ggtcaccatt aatcaaaggg      2220
```
aatgtacgtg tatgggcaat caacaagtcg tttcgataac cggtg         2265

<210> SEQ ID NO 2
<211> LENGTH: 449
<212> TYPE: PRT
<213> ORGANISM: Artificial Sequence
<220> FEATURE:
<223> OTHER INFORMATION: A polypeptide encoded by SEQ ID NO:1

<400> SEQUENCE: 2

```
Met Asn Tyr Asn Asn Lys Ile Leu Val Ser Glu Ser Gly Leu Ser Gln
 1               5                  10                  15

Lys His Leu Ile His Gly Asp Glu Glu Leu Phe Gln His Glu Leu Lys
                20                  25                  30

Thr Ile Phe Ala Arg Asn Trp Leu Phe Leu Thr His Asp Ser Leu Ile
            35                  40                  45

Pro Ala Pro Gly Asp Tyr Val Thr Ala Lys Met Gly Ile Asp Glu Val
        50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
                85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
    290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Val
            340                 345                 350

Gly Pro Ala Gly Phe Trp Glu Ser Asp Asp Asn Asp Asn Met Glu Thr
```

-continued

```
        355                 360                 365

Ala Ser Gln Asn Gly Lys Lys Tyr Gln Ser Arg Asp Ser Asp Leu Leu
    370                 375                 380

Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Gln Ala His Val Ser Ser Ser Asn Trp Ala Glu Phe
            420                 425                 430

Glu His Ala Ser Ser Thr Trp His Thr Glu Leu Thr Lys Thr Thr Asp
        435                 440                 445

Arg

<210> SEQ ID NO 3
<211> LENGTH: 9841
<212> TYPE: DNA
<213> ORGANISM: Artificial Sequence
<220> FEATURE:
<223> OTHER INFORMATION: A modified DNA molecule encoding valine at the
      position corresponding to the F352 amino acid in
      NDO.

<400> SEQUENCE: 3
gaattcatca ggaagacatt caaatgaacg taaacaataa gggcagcgtc tgtatttgcg     60
gcagcgaaat gctccctaaa ttcctcattt accccatctg aggattgctt tatgacagta    120
aagtggattg aagcagtcgc tctttctgac atccttgaag gtgacgtcct cggcgtgact    180
gtcgagggca aggagctggc gctgtatgaa gttgaaggcg aaatctacgc taccgacaac    240
ctgtgcacgc atggttccgc ccgcatgagt gatggttatc tcgagggtag agaaatcgaa    300
tgccccttgc atcaaggtcg gtttgacgtt tgcacaggca aagccctgtg cgcacccgtg    360
acacagaaca tcaaaacata tccagtcaag attgagaacc tgcgcgtaat gattgatttg    420
agctaagaat tttaacagga ggcaccccgg gccctagagc gtaatcaccc ccattccatc    480
ttttttaggt gaaaacatga attacaataa taaaatcttg gtaagtgaat ctggtctgag    540
ccaaaagcac ctgattcatg gcgatgaaga acttttccaa catgaactga aaaccatttt    600
tgcgcggaac tggctttttc tcactcatga tagcctgatt cctgcccccg gcgactatgt    660
taccgcaaaa atggggattg acgaggtcat cgtctcccgg cagaacgacg gttcgattcg    720
tgcttttctg aacgtttgcc ggcatcgtgg caagacgctg gtgagcgtgg aagccggcaa    780
tgccaaaggt tttgtttgca gctatcacgg ctggggcttc ggctccaacg gtgaactgca    840
gagcgttcca tttgaaaaag atctgtacgg cgagtcgctc aataaaaaat gtctggggtt    900
gaaagaagtc gctcgcgtgg agagcttcca tggcttcatc tacggttgct tcgaccagga    960
ggcccctcct cttatggact atctgggtga cgctgcttgg tacctggaac ctatgttcaa   1020
gcattccggc ggtttagaac tggtcggtcc tccaggcaag gttgtgatca aggccaactg   1080
gaaggcaccc gcggaaaact ttgtgggaga tgcataccac gtgggttgga cgcacgcgtc   1140
ttcgcttcgc tcgggggagt ctatcttctc gtcgctcgct ggcaatgcgg cgctaccacc   1200
tgaaggcgca ggcttgcaaa tgacctccaa atacggcagc ggcatgggtg tgttgtggga   1260
cggatattca ggtgtgcata gcgcagactt ggttccggaa ttgatggcat tcggaggcgc   1320
aaagcaggaa aggctgaaca aagaaattgg cgatgttcgc gctcggattt atcgcagcca   1380
cctcaactgc accgttttcc cgaacaacag catgctgacc tgctcgggtg ttttcaaagt   1440
```

-continued

| | |
|---|---|
| atggaacccg atcgacgcaa acaccaccga ggtctggacc tacgccattg tcgaaaaaga | 1500 |
| catgcctgag gatctcaagc gccgcttggc cgactctgtt cagcgaacgg tcgggcctgc | 1560 |
| tggcttctgg gaaagcgacg acaatgacaa tatggaaaca gcttcgcaaa acggcaagaa | 1620 |
| atatcaatca agagatagtg atctgctttc aaaccttggt ttcggtgagg acgtatacgg | 1680 |
| cgacgcggtc tatccaggcg tcgtcggcaa atcggcgatc ggcgagacca gttatcgtgg | 1740 |
| tttctaccgg gcttaccagg cacacgtcag cagctccaac tgggctgagt tcgagcatgc | 1800 |
| ctctagtact tggcatactg aacttacgaa gactactgat cgctaacaga cgagtcgacc | 1860 |
| atgatgatca atattcaaga agacaagctg gtttccgccc acgacgccga agagattctt | 1920 |
| cgtttcttca attgccacga ctctgctttg caacaagaag ccactacgct gctgacccag | 1980 |
| gaagcgcatt tgttggacat tcaggcttac cgtgcttggt tagagcactg cgtggggtca | 2040 |
| gaggtgcaat atcaggtcat ttcacgcgaa ctgcgcgcag cttcagagcg tcgttataag | 2100 |
| ctcaatgaag ccatgaacgt ttacaacgaa aattttcagc aactgaaagt tcgagttgag | 2160 |
| catcaactgg atccgcaaaa ctggggcaac agcccgaagc tgcgctttac tcgctttatc | 2220 |
| accaacgtcc aggccgcaat ggacgtaaat gacaaagagc tacttcacat ccgctccaac | 2280 |
| gtcattctgc accgggcacg acgtggcaat caggtcgatg tcttctacgc cgcccgggaa | 2340 |
| gataaatgga acgtggcga aggtggagta cgaaaattgg tccagcgatt cgtcgattac | 2400 |
| ccagagcgca tacttcagac gcacaatctg atggtctttc tgtgattcag tgaccatttt | 2460 |
| tacaaatggt cactgcaacc gcggtcacca ttaatcaaag ggaatgtacg tgtatgggca | 2520 |
| atcaacaagt cgtttcgata accggtgcag gctcaggaat cggtctcgaa ctggttcggt | 2580 |
| cctttaagtc ggccggttat tacgtatccg ctctcgtacg aaacgaggag caagaggcgc | 2640 |
| ttctttgcaa agagttcaag gacgcactcg agattgtagt gggcgatgtc cgggaccacg | 2700 |
| caacaaatga gaagctgata aagcaaacaa tcgatagatt cggtcatctt gattgtttta | 2760 |
| ttgcaaatgc cggtatctgg gattacatgc tgagcatcga agagccttgg gagaaaatat | 2820 |
| cgagcagttt tgacgaaata ttcgacatta atgtcaagag ctatttcagt ggcatcagtg | 2880 |
| ccgccctgcc ggaactgaaa aagactaacg gatcagtggt gatgaccgct tcggtgtcgt | 2940 |
| cccatgcggt cggtggtggt ggttcttgct acatcgccag caagcatgcg gtgctcggta | 3000 |
| tggttaaggc tttggcctac gaattggccc ccgaagttcg cgtgaacgct gtttcgccgg | 3060 |
| ggggcaccgt gacgtctctg tgcggtcccg cgagcgccgg tttcgacaaa atgcacatga | 3120 |
| aagacatgcc cggcatcgac gatatgatca aaggtctcac gcctcttggg tttgcagcca | 3180 |
| agcccgaaga cgtggtggca ccctatttgt tgctggcttc gcgaaagcaa ggaaaattca | 3240 |
| tcaccggcac cgtgattagc attgatgcg gtatggcgct cggtcgcaag tgagcttgta | 3300 |
| gccgatcaga agttatagac acatttcagg tgacgcccca tgaagacaaa actgtttatc | 3360 |
| aataacgcct ggatcgattc tagtgaccag cagaccttcg agcgcataca ccccgtcagc | 3420 |
| agcgatgtgg tgactgagag cgcaaacgcc acagtgacgg acgcgataaa ggcggcgcaa | 3480 |
| gcggccgagg aggcgttcaa gacctggaag gccgttggac cttcagagcg tcgccgcctt | 3540 |
| ctcctaaagg tcgccgatgt catggaaagt aaaacaccca agttcatcga agtgatggcc | 3600 |
| atggaggtgg gagcttccgc cctttgggcc ggattcaacg tccatgcgtc tgccaatgtg | 3660 |
| ttccgagagg ctgcctcgct ggctacccaa attcagggtg aaaccatccc aacggacaaa | 3720 |
| gccgaaacgc tctcaatgac actacgtcag ccggtcggcc cgatcctaag catcgttcca | 3780 |
| tggaacggca ccgcagtgct tgcggcacga gccatcgctt atccgctggt ctgtggcaac | 3840 |

```
actgtggtgt tcaaaggctc tgaatttagt cccgcgacgc atgccctgat cacccagtgc    3900
gtgcaggaag ccgggctgcc cgctggcgtg ctcaattacc tcaactcttc gcctgaccgt    3960
tcgcccgaga tcgctgacgc actgatctct gccaaggaga tccgccgcat caacttcacg    4020
ggttccaccc gcgtgggcag cattatcgcg cagaaagccg cgcaacacct caagcgctgc    4080
ctgctggagc tcggcggcaa gtccccgctt attgttctgg atgatgcaga catcgatgcg    4140
gcggtcaagg cagcggtgtt cggtagcttc ctgttccaag gtcagatctg catgtccact    4200
gagcgcttga tcgttgatga gaagatagcc gacgaatttg tcgcaaaatt tgtcgaaaaa    4260
actaagcgct gagcgcagg cgacccgtgc gtaactggcg actgcatcat cggcccgatg    4320
gtctcgccaa attcgggtga gcggatcaat ggtttgttca agacgcgat cgacaaaggg    4380
gcaaaagttg tttgcggcgg cttggcccaa ggtgcgctca tgccggccac gatcctggat    4440
cacgtcaaat ctgacatgcg gatttacgat gaggagacct ttggtcccat caccgtggta    4500
atccgttgta aggcgaagc agaggccgtc cgcattgcca acgacagcgt ctatggcctg    4560
tcgtcgggcg tatttggccg cgacatcaac cgcgctctac gcgtgggtat gtccatcgaa    4620
tatggttctg tacacatcaa cggttcgacc gtccagaacg aggcgcaggc tccttacgga    4680
ggcaccaaga acaccggcta cgggcgcttc gacggccgtg ctgtaatcga cgagttcaca    4740
gagatcaagt ggctgaccat cgaacctttc gagcagcaat atcccttctg ataagcacta    4800
actcccagga atcaaactat gagtaagcaa gctgcagtta tcgagctcgg atacatgggt    4860
atctcggtca aggaccctga tgcgtggaaa tcatttgcca cggatatgct aggtctgcaa    4920
gttcttgatg agggtgagaa ggaccgtttc tatctgcgga tggattactg gcatcatcgg    4980
atcgtagtcc atcacaacgg acaggacgac ttggagtacc taggctggcg tgtagccggc    5040
aagccggagt tcgaagctct gggtcaaaag cttattgatg ccggttacaa gatccgcatc    5100
tgcgacaaag ttgaggctca ggagcgtatg gtgttgggtc tgatgaagac agaagatccg    5160
ggcggcaacc cgaccgagat attctgggc ccccggatcg acatgagcaa cccgttccat    5220
cccggtcgcc cctgcacgg aaagtttgtg accggtgacc aaggcttggg ccattgcatc    5280
gttcgccaaa ccgacgtcgc agaagctcat aagtttata gcctgctggg cttccgtggg    5340
gacgtcgaat accggattcc gttgcccaac ggcatgactg ccgaactgtc gttcatgcat    5400
tgcaacgccc gtgatcactc cattgctttt ggtgccatgc ccgctgccaa acgactcaat    5460
cacttgatgc ttgagtacac ccatatggaa gacttgggat acacgcacca acagtttgta    5520
aagaacgaaa ttgacattgc cttgcagctt ggcattcacg ccaacgacaa ggcgttgacg    5580
ttctatggtg caacgccttc gggctggctc attgagcccg ctggcgagg tgccacggcc    5640
atagatgaag cggagtatta cgtcggcgac atcttcggcc atggcgtgga ggccactgga    5700
tatggcctgg atgtaaaact gagctaaaga tgcgcgctcg ttgggcgagg ctctagtcca    5760
gcatcttcat acgcaaccaa ccttgcaggg cgatgagatc aaaggacgtt aaagcgaagg    5820
ggaagtggtt cgggccatgc gcataccgat ccatgacatt tgtttcatag tatataggta    5880
gataggtgaa tcaagcgctt agtcaactag tggacacatc tgttccatga ggctatctac    5940
tatctattca aaacaagaat aataaatagg atgaaaataa taatgataaa agaacgatt    6000
tgtcttgtgt atcctctatt ctgtttggca agccccacat gggccgaaga gtcgccttgg    6060
acgtaccgta ttggtatgac taatgtagct ttcgatgcta gcgcaaaagt atacttaaat    6120
ggtcagcggg tgccaggagg aagcgctgat gcgagcgata caacgcgct tacattcgac    6180
```

-continued

```
ttcggctacg ccatcaacga ccagtggaat gtacgtgcga ttgtcggtat tccgcctaca      6240
actaaagtga cgggcgcagg cacacttcct ggtatccagc tggggaaaat aacttacgct      6300
ccaacagtat taacgttgaa ctataacctc cccgctttgg gtcccgttcg ccctcacata      6360
ggtgcgggag tcaattacac gcggattttt gaaagtcggg acgctaatct aaaatcgttc      6420
gatgccgacc acgcttggtc ccccgcgcta catgttggtg ccgatattga cgttaaccgt      6480
ggttggttcg ttagcattga tatccggaag ttatacctga aaaccgacgc atcagggtac      6540
ttggggccac aggaggctaa agcacgggta actcttgacc cattactaac ttcgatcgcg      6600
atcggacgcc aattctgatg attctgttta agttcttta tctatctaac cgcaaagggt       6660
gtttccatgt cgaataaaat tatgaaaacg tcgcgtctta ccgccgaaga tatcaacggc      6720
gcctggacta taatgcccac accctcgacg cctgatgctt ctgattggcg cagcactgcc      6780
accgtggact tagaagagac tgcccgcata gttgaagagc tgattgcagc tggtgtcaac      6840
ggtattctaa gtatgggtac ttttggtgag tcgccacgt tgacctggga tgaaaaacgt       6900
gattatgtct cgacgattgt cgagaccatt cgtggtcgcg tgccttattt ctgtggcacg      6960
acagccttaa ataccccgaga agtcatccgc cagacccgag agcttatcga tattggcgcc     7020
aacggcacta tgctcggggt gccgatgtgg gtgaagatgg acctgcctac agcggttcag      7080
ttctatcgtg atgttgcaga tgcggtacca gaggctgcca ttgcgattta cgccaacccc      7140
gaagcattca agttcgactt ccctcgccca ttctgggcag agatgtccaa aattccgcag      7200
gtagtgactg cgaagtatct aggcatcgga atgcttgact tggacctgag actggcaccc      7260
aacatccgct tccttcccca cgaagatgac tattacgcgg ccgcacgcat caatcccgag      7320
cgcataaccg cgttctggtc aagcgggggcc atgtgcggcc cggctaccgc catcatgttg      7380
cgtgacgaag tggtgcgggc caagagcacc ggtgactggg ccaaggccaa agccatctcc      7440
gatgatatgc gtgcagccga ctcgacattg tttccgcgtg gcgactttc ggagttctcg       7500 aagtataata tcgggcttga aaaggcacgg atggatgcgg ctggttggct caaggctggg      7560
ccctgccgtc cgcccctacaa ccttgttcca gaagactacc tcgctggtgc acagaaatca     7620
ggcaaggctt gggccgcgct gcacgctaaa tacagtaatg aattgaagta gttcacctcc     7680
gcagacctga gtgacagggt ggcgcagacg ctgagggtgc aggaattaag tgagctaaag      7740
cacatttctt gcgccaggca ttgccagatc agcaaagttt gctgatctgg cagtttcaaa     7800
aatttgggcg aaagctgata tcaggaatac gggataaagg cagtgcacca taacgacggg     7860
gcgtgccatt cgtgatgaac gattttgcta ttgtgccgac ttctgttctt ggagtgtttg     7920
attgtgattg tcgattttta tttcgatttt ttgagtccgt tctcttactt ggccaaccat      7980
cgtttgtcaa agcttgcgca agactatggc tttttccattc gttattacgc aatcgatttg    8040
gcgcgagtta aaatagccat cggaaacgtt ggtccatcta atcgcgacct gatagtcaag      8100
ctggactatt tgaaagtaga tttgcaacgg tgggccgagc tttacgaaat accgttggta     8160
ttcccagcta actacaacag ccgacggatg aatactgggc tttattactc gggagccatg     8220
gcacagactg gtgcctatgt gaatgtagta tttaatgcgg tttggggaga tggcatagct      8280
ccagatttgg aaagcttgcc tgctctggta tctgaaaaac taggctggga tcgtagcgcc      8340
ttcgaggact ttatcagcag cgatgccgca acagagaggt atgacgagca gacacatgcc      8400
gcgatcgaac gcaaagtgtt cggtgtgcca acgatgtttt tgggcgatga atgtgggtgg      8460
ggaaacgacc gtctatttat gctcgagaac gcagtgggag gtgcgcctgt aaatggagaa      8520
tagtcgctac ggagcgcttg tgccggctaa atgccgatat aagtggttga cctgatcgtt     8580
```

-continued

```
atttgctcga tacagcgctt tcaaaatcag cggctactga agtcagataa aaatgcggga   8640
ctacttcagg catcctgtgc gacacaaagt tttacctgta attgtccacc tattccgagt   8700
ttggaatggt agctgactcg ctatgcgacc agcgatagcc taacaagaca tgcatcactg   8760
gtaacggtgg ggtgtgaagc tcctgcaaca atgtagcccc ttgatgtgtg tatttgctgc   8820
gaggtgaagc acagatgctc ggagccgtac cggcttgtgg cgctaggctg gcaagtatga   8880
gcaacgtaag tgggggttgg ggcgcaatgg gaaccaaaaa ccaacgcaag ccttaccagc   8940
gtcgttcggt gccttcctcc catgcctccg cctcgataaa gcagctgcgc atatcggctt   9000
cctggctgat ctcggttagt aggtcatgca aggtcttgtc cagcgcctcg tcgctccgat   9060
acggaatggt cagctcgtaa tggccggtct ccgaccgctt catgccgtag ggctccaggc   9120
agtagcgctc gatgttctcc gtggcccgct tccgaccgcg catgaacttg ctgttgttca   9180
ccaccgccag gcgcagggtg acggtggcca cccgctcgac ggttgactct gccggtgacg   9240
cgatattgcg cttttgacct cgcgccaggg cgctcttctg gtacgtcccg atctcgacgc   9300
cacggtggcg taggtagctg tacagggtgc tcttggagat gtgcaacttc tcgccgatgg   9360
cgctgacgct caggcggccc tcgcggtaca gggtctccgc cgccatggcg gtggcctcgg   9420
ccttggctgg caggcccttg ggacggcgac cgatccggcc tcgagtccgt gccgccgaca   9480
ggcccgcctg agtccgctcg cggatcagct cgcgctcgaa ctgaacaggt tgaacaccag   9540
gcgatcttgg gcgtgggtgc tgtcaatggg gtcgttcagg ctctgcaagc cgactttgcg   9600
tgcagccagc tagccgacca actcaaccag gtgcttgagc gagcgaccga ggcgatccag   9660
cttccagatc accacggcat cgcccgctcg aacatgggct agcaacttgt ccaactccgg   9720
ccgcgcgctt tttgcgccgc tggcgatgtc ttgatagatg cgttcgcacc cggcctgttt   9780
cagggcatcg acctggaggt cggcgttcta atcccgagtg ctcacccgcg tataaccgat   9840
c                                                                  9841
```

<210> SEQ ID NO 4
<211> LENGTH: 2515
<212> TYPE: DNA
<213> ORGANISM: Artificial Sequence
<220> FEATURE:
<223> OTHER INFORMATION: A modified DNA molecule encoding valine at the position corresponding to the F352 amino acid in NDO.

<400> SEQUENCE: 4

```
gaattcatca ggaagacatt caaatgaacg taaacaataa gggcagcgtc tgtatttgcg     60
gcagcgaaat gctccctaaa ttcctcattt accccatctg aggattgctt tatgacagta    120
aagtggattg aagcagtcgc tctttctgac atccttgaag gtgacgtcct cggcgtgact    180
gtcgagggca aggagctggc gctgtatgaa gttgaaggcg aaatctacgc taccgacaac    240
ctgtgcacgc atggttccgc ccgcatgagt gatggttatc tcgagggtag agaaatcgaa    300
tgccccttgc atcaaggtcg gtttgacgtt tgcacaggca aagccctgtg cgcacccgtg    360
acacagaaca tcaaaacata tccagtcaag attgagaacc tgcgcgtaat gattgatttg    420
agctaagaat tttaacagga ggcaccccgg gccctagagc gtaatcaccc ccattccatc    480
ttttttaggt gaaaacatga attacaataa taaaatcttg gtaagtgaat ctggtctgag    540
ccaaaagcac ctgattcatg gcgatgaaga acttttccaa catgaactga aaaccatttt    600
tgcgcggaac tggctttttc tcactcatga tagcctgatt cctgccccccg gcgactatgt    660
```

-continued

```
taccgcaaaa atggggattg acgaggtcat cgtctcccgg cagaacgacg gttcgattcg    720
tgcttttctg aacgtttgcc ggcatcgtgg caagacgctg gtgagcgtgg aagccggcaa    780
tgccaaaggt tttgtttgca gctatcacgg ctggggcttc ggctccaacg gtgaactgca    840
gagcgttcca tttgaaaaag atctgtacgg cgagtcgctc aataaaaaat gtctggggtt    900
gaaagaagtc gctcgcgtgg agagcttcca tggcttcatc tacggttgct tcgaccagga    960
ggcccctcct cttatggact atctgggtga cgctgcttgg tacctggaac ctatgttcaa   1020
gcattccggc ggtttagaac tggtcggtcc tccaggcaag gttgtgatca aggccaactg   1080
gaaggcaccc gcggaaaact ttgtgggaga tgcataccac gtgggttgga cgcacgcgtc   1140
ttcgcttcgc tcgggggagt ctatcttctc gtcgctcgct ggcaatgcgg cgctaccacc   1200
tgaaggcgca ggcttgcaaa tgacctccaa atacggcagc ggcatgggtg tgttgtggga   1260
cggatattca ggtgtgcata gcgcagactt ggttccggaa ttgatggcat tcggaggcgc   1320
aaagcaggaa aggctgaaca aagaaattgg cgatgttcgc gctcggattt atcgcagcca   1380
cctcaactgc accgttttcc cgaacaacag catgctgacc tgctcgggtg ttttcaaagt   1440
atggaacccg atcgacgcaa acaccaccga ggtctggacc tacgccattg tcgaaaaaga   1500
catgcctgag gatctcaagc gccgcttggc cgactctgtt cagcgaacgg tcgggcctgc   1560
tggcttctgg gaaagcgacg acaatgacaa tatggaaaca gcttcgcaaa acggcaagaa   1620
atatcaatca agagatagtg atctgctttc aaaccttggt ttcggtgagg acgtatacgg   1680
cgacgcggtc tatccaggcg tcgtcggcaa atcggcgatc ggcgagacca gttatcgtgg   1740
tttctaccgg gcttaccagg cacacgtcag cagctccaac tgggctgagt tcgagcatgc   1800
ctctagtact tggcatactg aacttacgaa gactactgat cgctaacaga cgagtcgacc   1860
atgatgatca atattcaaga agacaagctg gtttccgccc acgacgccga agagattctt   1920
cgtttcttca attgccacga ctctgctttg caacaagaag ccactacgct gctgacccag   1980
gaagcgcatt tgttggacat tcaggcttac cgtgcttggt tagagcactg cgtggggtca   2040
gaggtgcaat atcaggtcat ttcacgcgaa ctgcgcgcag cttcagagcg tcgttataag   2100
ctcaatgaag ccatgaacgt ttacaacgaa aattttcagc aactgaaagt tcgagttgag   2160
catcaactgg atccgcaaaa ctggggcaac agcccgaagc tgcgctttac tcgctttatc   2220
accaacgtcc aggccgcaat ggacgtaaat gacaaagagc tacttcacat ccgctccaac   2280
gtcattctgc accgggcacg acgtggcaat caggtcgatg tcttctacgc cgcccgggaa   2340
gataaatgga aacgtggcga aggtggagta cgaaaattgg tccagcgatt cgtcgattac   2400
ccagagcgca tacttcagac gcacaatctg atggtctttc tgtgattcag tgaccatttt   2460
tacaaatggt cactgcaacc gcggtcacca ttaatcaaag ggaatgtacg tgtat        2515
```

```

<210> SEQ ID NO 5
<211> LENGTH: 9706
<212> TYPE: DNA
<213> ORGANISM: Artificial Sequence
<220> FEATURE:
<223> OTHER INFORMATION: A modified DNA molecule encoding valine at the
      position corresponding to the F352 amino acid in
      NDO.

<400> SEQUENCE: 5
gctgatttcg accaattatt ccacgccgtc tgcgccagca aggccgtaat cagttcgtaa     60
aggggagccc gcagtaacag cgaaccgacg ccggtagctg cgcgcgtgaa tcctgagatc    120
acaaattctt ggcgattatc gcatttcaat ttcacccaag cgccgttcct tgcgctgctg    180
```

-continued

```
tagcggcggc catcacgctt ctccacgatt ccctccagct gcatccggca agcgttggcc      240
agcagctgca ctgggtaagc ttccagggta tcgctgaagc gtacgcgctc caatgggcag      300
tgctcgagga gcgcctcaag tacctggcgg ctcagttcaa cgccctctcc ccgcagatct      360
gcaccgtcga ggtagagcag gtcgaacgcc acgtacacaa atttgtcggt acaccgtgcg      420
gcgaacgctg actgcaggGC ttgaaatgct ggtcgaccgt cgtcatactg gaatacgacc      480
tcaccgtcga gccaggctga atggacggct aggcgtccca gctatttggc caggagtggc      540
atatgatcga tctagtcaaa cccgttttTG gtgaaaagct gcacctggtc accatcgatc      600
cgtgctaaca gacgatacca gtcgtacttg atctcgtatc gccatgctcc tgccgacgac      660
agtgtcagta gagtaaccag ttgtggcgcg atccaacacg ggtttggtgc cttgggcggt      720
ttcactatcg ccacctcgct ataggaacat tccttcaggg tggagtgcgt aattttctga      780
aaggggagcc aggttatgag tattcacatt ggtgataaac aacatcactt atgcgttatt      840
gacatataac gtcgtattca cgattattta ccatataagt cttataataa cgaagccata      900
ttatggaact cctcatacaa ccgaaaaatc gcataattcc cttcagtgcc ggtgccaacc      960
ttctggaagt gcttcgcgag aacggtgtag ctatttccta cagttgcttg tctgggcgtt     1020
gcggaacctg tcgctgccgg gttatagatg gcagtgtcat tgattctggg gcggaaaatg     1080
ggcaatcaaa cctcaccgac aagcagtatg tgctcgcctg tcagtcagta ctcactggca     1140
attgcgctat cgaagtccca gaagccgacg aaattgtcac tcacccgcg cgaatcatca     1200 agggcacagt ggtcgcagtc gagtcgccca ctcacgatat ccgtcgctta cgcgtacgcc     1260
tctccaagcc cttcgagttc tcacccggac agtacgcgac actgcagttc agccctgagc     1320
atgcgcgtcc gtattcaatg gcaggtttgc cagatgacca agaaatggag ttccacatac     1380
gcaaggtgcc gggtgggcgc gtcacggagt atgttttcga acacgtccgc gaaggtacaa     1440
gcatcaagtt gagcgggcct cttggtacgg cttatctacg tcagaagcac accggaccga     1500
tgctgtgtgt aggtggcggg accggactcg caccggtgct gtcgattgtt cgcggcgcgc     1560
tgaagtcggg tatgacgaac cccatcctcc tttatttcgg ggtgcgcagt cagcaagacc     1620
tctacgacgc agagcgattg cacaaactcg ccgctgacca ccctcaactg accgtacaca     1680
cggtgattgc aacgggcccg attaatgagg gtcagcgagc cggcctaatt accgatgtga     1740
tcgaaaaaga catcctttcg ctggctgggt ggagggccta cctgtgcggc gcaccagcga     1800
tggttgaagc gttgtgcacc gtcaccaagc atcttggaat atcacccgaa catatttatg     1860
ccgatgcctt ctatcccggt gggatctgaa tagttcccgg ccatgcacct ctgtccatcg     1920
agaattcatc aggaagacat tcaaatgaac gtaaacaata agggcagcgt ctgtatttgc     1980
ggcagcgaaa tgctccctaa attcctcatt taccccatct gaggattgct ttatgacagt     2040
aaagtggatt gaagcagtcg ctcttcctga catccttgaa ggtgacgtcc tcggcgtgac     2100
tgtcgagggc aaggagctgg cgctgtatga agttgaaggc gaaatctacg ctaccgacaa     2160
cctgtgcacg catggttccg cccgcatgag tgatggttat ctcgagggta gagaaatcga     2220
atgccccttg catcaaggtc ggtttgacgt ttgcacaggc aaagccctgt gcgcacccgt     2280
gacacagaac atcaaaacat atccagtcaa gattgagaac ctgcgcgtaa tgattgattt     2340
gagctaagaa ttttaacagg aggcaccccg ggccctagag cgtaatcacc cccattccat     2400 ctttttttagg tgaaaacatg aattacaata ataaaatctt ggtaagtgaa ctgtggtctga     2460 gccaaaagca cctgattcat ggcgatgaag aacttttcca acatgaactg aaaaccattt     2520
```

```
ttgcgcggaa ctggcttttt ctcactcatg atagcctgat tcctgccccc ggcgactatg   2580
ttaccgcaaa aatggggatt gacgaggtca tcgtctcccg gcagaacgac ggttcgattc   2640
gtgcttttct gaacgtttgc cggcatcgtg gcaagacgct ggtgagcgtg gaagccggca   2700
atgccaaagg ttttgtttgc agctatcacg gctggggctt cggctccaac ggtgaactgc   2760
agagcgttcc atttgaaaaa gatctgtacg gcgagtcgct caataaaaaa tgtctggggt   2820
tgaaagaagt cgctcgcgtg gagagcttcc atggcttcat ctacggttgc ttcgaccagg   2880
aggcccctcc tcttatggac tatctgggtg acgctgcttg gtacctggaa cctatgttca   2940
agcattccgg cggtttagaa ctggtcggtc tccaggcaa ggttgtgatc aaggccaact   3000
ggaaggcacc cgcggaaaac tttgtgggag atgcatacca cgtgggttgg acgcacgcgt   3060
cttcgcttcg ctcgggggag tctatcttct gctcgctcgc tggcaatgcg cgctaccac   3120 ctgaaggcgc aggcttgcaa atgacctcca atacggcag cggcatgggt gtgttgtggg   3180
acggatattc aggtgtgcat agcgcagact tggttccgga attgatgca ttcggaggcg   3240 caaagcagga aaggctgaac aaagaaattg gcgatgttcg cgctcggatt tatcgcagcc   3300
acctcaactg caccgttttc ccgaacaaca gcatgctgac ctgctcgggt gttttcaaag   3360
tatggaaccc gatcgacgca aacaccaccg aggtctggac ctacgccatt gtcgaaaaag   3420
acatgcctga ggatctcaag cgccgcttgg ccgactctgt tcagcgaacg gtcgggcctg   3480
ctggcttctg ggaaagcgac gacaatgaca atatggaaac agcttcgcaa aacggcaaga   3540
aatatcaatc aagagatagt gatctgcttt caaaccttgg tttcggtgag gacgtatacg   3600
gcgacgcggt ctatccaggc gtcgtcggca atcggcgat cggcgagacc agttatcgtg   3660
gtttctaccg ggcttaccag gcacacgtca gcagctccaa ctgggctgag ttcgagcatg   3720
cctctagtac ttggcatact gaacttacga agactactga tcgctaacag acgagtcgac   3780
catgatgatc aatattcaag aagacaagct ggtttccgcc cacgacgccg aagagattct   3840
tcgtttcttc aattgccacg actctgcttt gcaacaagaa gccactacgc tgctgaccca   3900
ggaagcgcat ttgttggaca ttcaggctta ccgtgcttgg ttagagcact gcgtggggtc   3960
agaggtgcaa tatcaggtca tttcacgcga actgcgcgca gcttcagagc gtcgttataa   4020
gctcaatgaa gccatgaacg tttacaacga aaattttcag caactgaaag ttcgagttga   4080
gcatcaactg gatccgcaaa actggggcaa cagcccgaag ctgcgcttta ctcgctttat   4140
caccaacgtc caggccgcaa tggacgtaaa tgacaaagag ctacttcaca tccgctccaa   4200
cgtcattctg caccgggcac gacgtggcaa tcaggtcgat gtcttctacg ccgcccggga   4260
agataaatgg aaacgtggcg aaggtggagt acgaaaattg gtccagcgat tcgtcgatta   4320
cccagagcgc atacttcaga cgcacaatct gatggtcttt ctgtgattca gtgaccattt   4380
ttacaaatgg tcactgcaac cgcggtcacc attaatcaaa gggaatgtac gtgtatgggc   4440
aatcaacaag tcgtttcgat aaccggtgca ggctcaggaa tcggtctcga actggttcgg   4500
tcctttaagt cggccggtta ttacgtatcc gctctcgtac gaaacgagga gcaagaggcg   4560
cttctttgca aagagttcaa ggacgcactc gagattgtag tgggcgatgt ccgggaccac   4620
gcaacaaatg agaagctgat aaagcaaaca atcgatagat tcggtcatct tgattgtttt   4680
attgcaaatg ccggtatctg ggattacatg ctgagcatcg aagagccttg ggagaaaata   4740
tcgagcagtt ttgacgaaat attcgacatt aatgtcaaga gctatttcag tggcatcagt   4800
gccgccctgc cggaactgaa aaagactaac ggatcagtgg tgatgaccgc ttcggtgtcg   4860
tcccatgcgg tcggtggtgg tggttcttgc tacatcgcca gcaagcatgc ggtgctcggt   4920
```

```
atggttaagg ctttggccta cgaattggcc cccgaagttc gcgtgaacgc tgtttcgccg    4980
gggggcaccg tgacgtctct gtgcggttcc gcgagcgccg gtttcgacaa aatgcacatg    5040
aaagacatgc ccggcatcga cgatatgatc aaaggtctca cgcctcttgg gtttgcagcc    5100
aagcccgaag acgtggtggc accctatttg ttgctggctt cgcgaaagca aggaaaattc    5160
atcaccggca ccgtgattag cattgatggc ggtatggcgc tcggtcgcaa gtgagcttgt    5220
agccgatcag aagttataga cacatttcag gtgacgcccc atgaagacaa aactgtttat    5280
caataacgcc tggatcgatt ctagtgacca gcagaccttc gagcgcatac accccgtcag    5340
cagcgatgtg gtgactgaga gcgcaaacgc cacagtgacg gacgcgataa aggcggcgca    5400
agcggccgag gaggcgttca agacctggaa ggccgttgga ccttcagagc gtcgccgcct    5460
tctcctaaag gtcgccgatg tcatggaaag taaaacaccc aagttcatcg aagtgatggc    5520
catggaggtg ggagcttccg cccttttggc cggattcaac gtccatgcgt ctgccaatgt    5580
gttccgagag gctgcctcgc tggctaccca aattcagggt gaaaccatcc caacggacaa    5640
agccgaaacg ctctcaatga cactacgtca gccggtcggc ccgatcctaa gcatcgttcc    5700
atggaacggc accgcagtgc ttgcggcacg agccatcgct tatccgctgg tctgtggcaa    5760
cactgtggtg ttcaaaggct ctgaatttag tcccgcgacg catgccctga tcacccagtg    5820
cgtgcaggaa gccgggctgc cgctggcgt gctcaattac ctcaactctt cgcctgaccg    5880
ttcgcccgag atcgctgacg cactgatctc tgccaaggag atccgccgca tcaacttcac    5940
gggttccacc cgcgtgggca gcattatcgc gcagaaagcc gcgcaacacc tcaagcgctg    6000
cctgctggag ctcggcggca agtccccgct tattgttctg gatgatgcag acatcgatgc    6060
ggcggtcaag gcagcggtgt tcggtagctt cctgttccaa gtcagatct gcatgtccac    6120
tgagcgcttg atcgttgatg agaagatagc cgacgaattt gtcgcaaaat tgtcgaaaa    6180
aactaagcgc ttgagcgcag gcgacccgtg cgtaactggc gactgcatca tcggcccgat    6240
ggtctcgcca aattcgggtg agcggatcaa tggtttgttc aaagacgcga tcgacaaagg    6300
ggcaaaagtt gtttgcggcg gcttggccca aggtgcgctc atgccggcca cgatcctgga    6360
tcacgtcaaa tctgacatgc ggatttacga tgaggagacc tttggtccca tcaccgtggt    6420
aatccgttgt aaaggcgaag cagaggccgt ccgcattgcc aacgacagcg tctatggcct    6480
gtcgtcgggc gtatttggcc gcgacatcaa ccgcgctcta cgcgtgggta tgtccatcga    6540
atatggttct gtacacatca acggttcgac cgtccagaac gaggcgcagg ctccttacgg    6600
aggcaccaag aacaccggct acgggcgctt cgacggccgt gctgtaatcg acgagttcac    6660
agagatcaag tggctgacca tcgaaccttt cgagcagcaa tatcccttct gataagcact    6720
aactcccagg aatcaaacta tgagtaagca agctgcagtt atcgagctcg atacatggg    6780
tatctcggtc aaggaccctg atgcgtggaa atcatttgcc acggatatgc taggtctgca    6840
agttcttgat gagggtgaga aggaccgttt ctatctgcgg atggattact ggcatcatcg    6900
gatcgtagtc catcacaacg gacaggacga cttggagtac ctaggctggc gtgtagccgg    6960
caagccggag ttcgaagctc tgggtcaaaa gcttattgat gccggttaca agatccgcat    7020
ctgcgacaaa gttgaggctc aggagcgtat ggtgttgggt ctgatgaaga cagaagatcc    7080
gggcggcaac ccgaccgaga tattctgggg ccccgggat cacatgagca cccgttcca    7140
tcccggtcgc ccctgcacg gaaagttggt gaccggtgac caaggctgg gccattgcat    7200
cgttcgccaa accgacgtcg cagaagctca taagtttat agcctgctgg gcttccgtgg    7260
```

```
ggacgtcgaa taccggattc cgttgcccaa cggcatgact gccgaactgt cgttcatgca   7320
ttgcaacgcc cgtgatcact ccattgcttt tggtgccatg cccgctgcca aacgactcaa   7380
tcacttgatg cttgagtaca cccatatgga agacttggga tacacgcacc aacagtttgt   7440
aaagaacgaa attgacattg ccttgcagct tggcattcac gccaacgaca aggcgttgac   7500
gttctatggt gcaacgcctt cgggctggct cattgagccc ggctggcgag gtgccacggc   7560
catagatgaa gcggagtatt acgtcggcga catcttcggc catggcgtgg aggccactgg   7620
atatggcctg gatgtaaaac tgagctaaag atgcgcgctc gttgggcgag gctctagtcc   7680
agcatcttca tacgcaacca accttgcagg gcgatgagat caaaggacgt taaagcgaag   7740
gggaagtggt tcgggccatg cgcataccga tccatgacat ttgtttcata gtatataggt   7800
agataggtga atcaagcgct tagtcaacta gtggacacac ctgttccatg aggctatcta   7860
ctatctattc aaaacaagaa taataaatag gatgaaaata ataatgataa aagaacgat    7920
ttgtcttgtg tatcctctat tctgtttggc aagccccaca tgggccgaag agtcgccttg   7980
gacgtaccgt attggtatga ctaatgtagc tttcgatgct agcgcaaaag tatacttaaa   8040
tggtcagcgg gtgccaggag gaagcgctga tgcgagcgat aacaacgcgc ttacattcga   8100
cttcggctac gccatcaacg accagtggaa tgtacgtgcg attgtcggta ttccgcctac   8160
aactaaagtg acgggcgcag gcacacttcc tggtatccag ctggggaaaa taacttacgc   8220
tccaacagta ttaacgttga actataacct ccccgctttg ggtcccgttc gccctcacat   8280
aggtgcggga gtcaattaca cgcggatttt tgaaagtcgg gacgctaatc taaaatcgtt   8340
cgatgccgac cacgcttggt cccccgcgct acatgttggt gccgatattg acgttaaccg   8400
tggttggttc gttagcattg atatccggaa gttatacctg aaaagcgacg catcagggta   8460
cttggggcca caggaggcta aagcacgggt aactcttgac ccattactaa cttcgatcgc   8520
gatcggacgc caattctgat gattctgttt aaagttcttt atctatctaa ccgcaaaggg   8580
tgtttccatg tcgaataaaa ttatgaaaac gtcgcgtctt accgccgaag atatcaacgg   8640
cgcctggact ataatgccca caccctcgac gcctgatgct tctgattggc gcagcactgc   8700
caccgtggac ttagaagaga ctgcccgcat agttgaagag ctgattgcag ctggtgtcaa   8760
cggtattcta agtatgggta cttttggtga gtgcgccacg ttgacctggg atgaaaaacg   8820
tgattatgtc tcgacgattg tcgagaccat tcgtggtcgc gtgccttatt tctgtggcac   8880
gacagcctta ataccccgag aagtcatccg ccagacccga gagcttatcg atattggcgc   8940
caacggcact atgctcgggg tgccgatgtg ggtgaagatg gacctgccta cagcggttca   9000
gttctatcgt gatgttgcag atgcggtacc agaggctgcc attgcgattt acgccaaccc   9060
cgaagcattc aagttcgact ccctcgccc attctgggca gagatgtcca aaattccgca   9120
ggtagtgact gcgaagtatc taggcatcgg aatgcttgac ttggacctga gactggcacc   9180
caacatccgc ttccttcccc acgaagatga ctattacgcg gccgcacgca tcaatcccga   9240
gcgcataacc gcgttctggt caagcggggc catgtgcggc ccggctaccg ccatcatgtt   9300
gcgtgacgaa gtggtgcggg ccaagagcac cggtgactgg gccaaggcca agccatctc   9360
cgatgatatg cgtgcagccg actcgacatt gtttccgcgt ggcgactttt cggagttctc   9420
gaagtataat atcgggcttg aaaaggcacg gatggatgcg gctggttggc tcaaggctgg   9480
gccctgccgt ccgccctaca accttgttcc agaagactac ctcgctggtg cacagaaatc   9540
aggcaaggct tgggccgcgc tgcacgctaa atacagtaat gaattgaagt agttcacctc   9600
cgcagacctg agtgacaggg tggcgcagac gctgagggtg caggaattaa gtgagctaaa   9660
```

-continued gcacatttct tgcgccaggc attgccagat cagcaaagtt tgctga 9706

<210> SEQ ID NO 6
<211> LENGTH: 2294
<212> TYPE: DNA
<213> ORGANISM: Artificial Sequence
<220> FEATURE:
<223> OTHER INFORMATION: A modified DNA molecule encoding valine at the position corresponding to the F352 amino acid in NDO.
<221> NAME/KEY: misc_feature
<222> LOCATION: (186)...(186)
<223> OTHER INFORMATION: n = a or t or g or c

<400> SEQUENCE: 6
agggcagckt ctgtatttgc ggcagcgaaa tgctccctaa attcctcatt taccccatct 60
gaggattgct ttatgacagt aaagtggatt gaagcagtcg ctctttctga catccttgaa 120
ggtgacgtcc tcggcgtgac tgtcgagggc aaggagctgg cgctgtatga agttgaaggc 180
gaaatntacg ctaccgacaa cctgtgcacg catggttccg cccgcatgag tgatggttat 240
ctcgagggta gagaaatcga atgccccttg catcaaggtc ggtttgacgt ttgcacaggc 300
aaagccctgt gcgcacccgt gacacagaac atcaaaacat atccagtcaa gattgagaac 360
ctgcgcgtaa tgattgattt gagctaagaa ttttaacagg aggcaccccg ggccctagag 420
cgtaatcacc cccattccat cttttttagg tgaaaacatg aattacaata ataaaatctt 480
ggtaagtgaa tttggtctga gccaaaagca cctgattcat ggcgatgaag aacttttcca 540
acatgaactg aaaaccattt ttgcgcggaa ctggcttttt ctcactcatg atagcctgat 600
tcctgccccc ggcgactatg ttaccgcaaa aatggggatt gacgaggtca tcgtctcccg 660
gcagaacgac ggttcgattc gtgcttttct gaacgtttgc cggcatcgtg gcaagacgct 720
ggtgagcgtg gaagccggca atgccaaagg ttttgtttgc agctatcacg gctggggctt 780
cggctccaac ggtgaactgc agagcgttcc atttgaaaaa gatctgtacg gcgagtcgct 840
caataaaaaa tgtctggggt tgaaagaagt cgctcgcgtg gagagcttcc atggcttcat 900
ctacggttgc ttcgaccagg aggcccctcc tcttatggac tatctgggtg acgctgcttg 960
gtacctggaa cctatgttca agcattccgg cggtttagaa ctggtcggtc ctccaggcaa 1020
ggttgtgatc aaggccaact ggaaggcacc cgcggaaaac tttgtgggag atgcatacca 1080
cgtgggttgg acgcacgcgt cttcgcttcg ctcgggggag tctatcttct cgtcgctcgc 1140
tggcaatgcg gcgctaccac ctgaaggcgc aggcttgcaa atgacctcca aatacggcag 1200
cggcatgggt gtgttgtggg acggatattc aggtgtgcat agcgcagact tggttccgga 1260
attgatggca ttcggaggcg caaagcagga aaggctgaac aaagaaattg gcgatgttcg 1320
cgctcggatt tatcgcagcc acctcaactg caccgttttc ccgaacaaca gcatgctgac 1380
ctgctccggt gttttcaaag tatggaaccc gatcgacgca aacaccaccg aggtctggac 1440
ctacgccatt gtcgaaaaag acatgcctga ggatctcaag cgccgcttgg ccgactctgt 1500
tcagcgaacg gtcgggcctg ctggcttctg ggaaagcgac gacaatgaca atatggaaac 1560
agcttcgcaa aacggcaaga aatatcaatc aagagatagt gatctgcttt caaaccttgg 1620
tttcggtgag gacgtatacg gcgacgcggt ctatccaggc gtcgtcggca aatcggcgat 1680
cggcgagacc agttatcgtg gtttctaccg ggcttaccga gcacacgtca gcagctccaa 1740
ctgggctgag ttcgagcatg cctctagtac ttggcatact gaacttacga agactactga 1800
tcgctaacag acgagtcgac catgatgatc aatattcaag aagacaagct ggtttccgcc 1860

-continued

```
cacgacgccg aagagattct tcgtttcttc aattgccacg actctgcttt gcaacaagaa   1920
gccactacgc tgctgaccca ggaagcgcat ttgttggaca ttcaggctta ccgtgcttgg   1980
ttagagcact gcgtggggtc agaggtgcaa tatcaggtca tttcacgcga actgcgcgca   2040
gcttcagagc gtcgttataa gctcaatgaa gccatgaacg tttacaacga aaattttcag   2100
caactgaaag ttcgagttga gcatcaactg gatccgcaaa actggggcaa cagcccgaag   2160
ctgcgcttta ctcgctttat caccaacgtc caggccgcaa tggacgtaaa tgacaaagag   2220
ctacttcaca tccgctccaa cgtcattctg caccgggcac gacgtggcaa tcaggtcgat   2280
gtcttctacg ccgc                                                     2294
```

<210> SEQ ID NO 7
<211> LENGTH: 4355
<212> TYPE: DNA
<213> ORGANISM: Artificial Sequence
<220> FEATURE:
<223> OTHER INFORMATION: A modified DNA molecule encoding valine at the position corresponding to the F352 amino acid in NDO.

<400> SEQUENCE: 7

```
atcgataaaa ccatgagggt aataaataat gatgaaggag actatctaga attcgttctg     60
gagacggtgc cggtggcata accgtagacc agcaggctga gcaaaatacc tcggggtgat    120
aagccgcgct accgcgtccg ccatatgcct gagtgagtgc gctaaggtcg ggccgctcaa    180
tggcttcgag aataaagcgg gccaggtgat cttctgtcaa tctcgccgaa tgggtggaag    240
cacatcaacc tgaccggcga ttacgtctgg cggcagagcc gcagactgga ggtcgggaag    300
ttccggccgt tacggcggcc ctgaaaacct tagtgtacga ttttttccgt cttctctatt    360
cggcctgcgt tgcgacgttc gatctgacta gggcgcagcg gcaacatcgg ctgagtacga    420
tccagcgcct ggatctgggt tatttcgtca accgacaaca ccagagcgtt atccggtggg    480
ttcaggtaaa gcccaaccac attgactacc tctcggcaaa atgagggtcg ttactaattt    540
tgaacgtctt caagcgatgg ggttttaggt cggaagctgc ccagacctgc ccaacctacc    600
acgtcgtgac ccgagcatat tcggcccgcg gcggcaaaaa acacagaaat gagcgggtga    660
cccgatcgcc tttgatcgat tctccgcttt caaaatgggc gggggctgaa gtcagccaga    720
aatacatgac tacttcagac gattcgcagt attcacgctg gtgataaaca aattcaacta    780
tgctttattg acaaataaaa gcacgctcac catcatcgcg aatacaaatc ttataaaaat    840
taagccggat ttatggaact tctcatacag ccaaacaatc gcctcattag ctttagtccc    900
ggcgccaacc ttctggaagt gcttcgcgaa aacggtgtcg ctatttccta cagttgtatg    960
tctgggcgtt gcggaacctg ccgctgtcgg gttacagatg gcagtgtaat tgattcgggg   1020
gcgggaagcg ggttaccaaa cctcgtggac gagcattatg tgctcgcctg tcagtcagta   1080
cttactcaca attgcgcgat cgaaatccca gaaaccgacg aaatcgtcac ccacccggcg   1140
agaatcatca agggcactgt ggtcgccgtc gagtcgccca ctcacgatat ccgtcgccta   1200
cgcgtacgcc tcgctaagcc cttcgagttc tcacccggac agtacgcgac attgcagttc   1260
agtcctgagc atgcgcgtcc gtattcaatg gcaggtctgc cagatgacca agaaatggag   1320
ttccacatac gcaaggtgcc gggtgggcgc gtaacggagt atgttttcga gcacgtccgc   1380
gaaggtacaa gcatcaagtt gagcgggcca cttggtacgg cttatttgcg tcagaaccac   1440
accgggccga tgctctgtgt gggcggtggg accggactag caccggtgct gtcgattgtt   1500
```

```
cgcggcgcgc tgaagttggg tatgacaaac cccatcctcc tttatttcgg agtgcgcagt    1560
cagcaagacc tctacgacgc agagcgattg cacaaactcg ccgctgatca ccctcaactg    1620
accgtacaca cggtaatcgc aatgggcccg attaatgaga gtcagcgagc cggtctagtt    1680
accgatgtga tcgaaaaaga catcatttcg ctggctgggt ggagggccta cctgtgcggc    1740
gcaccagcga tggttgaagc gctttgcacc gttaccaagc atcttggaat atcacccgaa    1800
catatttatg ccgatgcctt ctatcccggt ggaatctgaa tagtccctttt ccctgcacct    1860 ctgtccatcg aggactcatc aggaggatac tcaaataagc gcaaataata acagtcgcgt    1920
cagtatttgc ggcagcgaaa tggtttccct ctccctcatt tacccatct gaggatagtt     1980 ttatgacaga aaatggatt gaagcagtcg ccctttctga catcccagaa ggtgatgtcc     2040
tcggcgtgac tgtcgagggc aaggagctgg cgttgtacga agtggaaggc gaaatctacg    2100
ctaccgacaa cctgtgcacg catggtgccg cccgcatgag cgatggttat ctcgaggggc    2160
gagaaatcga atgcccctt g catcaaggtc ggtttgacgt ttgtacaggc agagccctct    2220
gcgcccccgt gacagagaac atcaaaacat atgcagtcaa gattgagaac ctgcgcgtaa    2280
tgattgattt gagcggagag ttttaatagg aggtaccccg gaccctagcg cgtaactacc    2340
ccaattccat cttttttagg tgaaaacatg aattacaaaa acaaaatatt ggtgagtgaa    2400
tctgggctga cccaaaagca cctgattcat ggcgatgaag aacttttcca gcacgaactg    2460
agaaccattt ttgcgcggaa ctggcttttt ctcactcatg acagcctgat tccatccccc    2520
ggcgactatg ttaccgcaaa aatgggtatt gacgaggtca tcgtctctcg gcagagcgac    2580
ggttcgattc gtgccttcct gaacgtttgt cggcaccgtg gcaagacgct ggttaacgcg    2640
gaagccggca atgccaaagg tttcgtttgc agctatcacg gctggggctt cggctccaac    2700
ggtgaactgc agagcgttcc attcgaaaaa gagctgtacg gcgagtcgct caacaaaaaa    2760
tgtctggggt tgaaagaagt cgctcgcgtg gagagcttcc atggcttcat ctatggttgc    2820
ttcgatcagg aggcccctcc tcttatggac tatctgggtg acgctgcttg gtacctagag    2880
cccatcttca aacattcagg cggtttagaa ctggtcggtc ctccaggcaa ggttgtgatc    2940
aaggccaact ggaaggcacc cgcggaaaac tttgtggggg atgcatacca cgtgggttgg    3000
acgcacgcgt cttcgcttcg ctcgggagag tctatcttcg cgtcgctcgc tggcaacgca    3060
gtgctgcccc ctgaaggtgc aggcttgcaa atgacctcca aatacggcag cggcatgggt    3120
gtgttgtggg acggatattc aggcgtgcat agcgcagact tggttccgga gttgatggca    3180
ttcggcggct ctaagcagga aaggctgaac aaagaaattg gcgatgttcg cgcccggatt    3240
tatcgcagcc acctcaactg caccgttttc ccgaacaaca gcatgctgac ctgctcgggt    3300
gttttcaaag tatggaaccc gatcgacgca aacaccaccg aggtctggac ctacgccatt    3360
gtcgaaaaag acatgcccga ggatctcaag cgccgcttgg ccgactcggt tcagcgtacg    3420
gttgggcctg ctgcttctg ggaaagcgac gacaatgaca atatgaaac agcgtcgcaa      3480 aacggcaaga aatatcaatc cagagatagt gatctgcttt caaaccttgg tttcggtaag    3540
gacgtatacg gcgacgcggt ctatcctggc gtcgtcggca atcggcgat cggcgagacc     3600 agttatcgtg gtttctaccg ggcttaccag gcacacgtca gcagctccaa ctgggctgag    3660
ttcgaggatg cctctagtac ttggcatacc gaactgacga agactactga tcgctaacag    3720
acgagtcgac catgatgatc aatattcaag aagacaagct ggtctccgcc cacgacgccc    3780
aagagtttct tcgtttcttc aattgccacg acgcggcttt gcaacaagaa gccaccacgc    3840
tgctgaaccg ggaagcgcat ctgttggaca ttcaggctta ccgggcttgg ttagagcact    3900
```

```
gcgtggggtc agaggttcaa tatcaggtca tttcacgcga actgcgcgcc gcttccgagc    3960
gccgttataa gctcaatgaa gccatgaacg tttacaacga aaattttcag caactgaaag    4020
ttcgaatcga gcatcaactg gatccgcaaa actggagcaa cagcccgaag ctgcgcttta    4080
ctcgcttcat caccaatgtc caggccgcaa gggacgtaga tgacgaagag ctacttcaca    4140
tccgctccaa cgtcattctg cacccgggcac gacgtggcaa tcaggtcgat gtcttctacg    4200
ccgcccggga agacaaatgg aaacgtggcg aaggtggagt gcgaaaattg gtccagcgat    4260
tcgtggatta cccagagcgc atacttcaga gcacaatct gatggtcttt ctgtgatcca    4320
gtgaccactt ttacaaatgg tgactgctac cgcgg                                4355
```

<210> SEQ ID NO 8
<211> LENGTH: 2176
<212> TYPE: DNA
<213> ORGANISM: Artificial Sequence
<220> FEATURE:
<223> OTHER INFORMATION: A modified DNA molecule encoding valine at the
      position corresponding to the F352 amino acid in
      NDO.

<400> SEQUENCE: 8

```
gtgatgtcct cggcgtgact gtcgagggta a

```
gtttcgggaa ggatgtatac ggcgacgcgg tctatcctgg cgtcgtcgga aaatcggcga    1560
tcggcgagac cagttatcgt ggtttctacc gggcttacca ggcacacgtc agcagctcca    1620
actgggctga gttcgaggat gcctctagta cttggcatac cgaactgacg aagactactg    1680
atcgctaaca gacgagtcga ccatgatgat caatactcaa gaagacaagc tggtatccgc    1740
ccatgacgcc gaaagttttc ttcgtttctt caattgccac gactcggctt tgcaacaaga    1800
agccaccacg ctgctgaccc gggaagcgca tctgctggac attcaggctt accggacttg    1860
gttagagcac tgcgtggggt cagaggttca atatcaagtc atttcacgcg aactgcgcgc    1920
cgcttccgag cgccgttata agctcaatga agccatgaac gtttacaacg aaaatttcca    1980
gcaactgaaa gttcgagtcg agcatcaact ggattcacaa aactggagca acagcccgaa    2040
gctgcgcttt actcgcttca tcaccaatgt ccaggccgca atggacgtaa atgatgaaga    2100
tctgcttcac gtccgctcca acgtcgttct gcaccgggca cgacgtggca atcaagtcga    2160
tgtcttctac gccgcc                                                    2176

<210> SEQ ID NO 9
<211> LENGTH: 14462
<212> TYPE: DNA
<213> ORGANISM: Artificial Sequence
<220> FEATURE:
<223> OTHER INFORMATION: A modified DNA molecule encoding valine at the
      position corresponding to the F352 amino acid in
      NDO.

<400> SEQUENCE: 9
gtcgactccg gtggccaaat cgacgggagc acaagcgtta cagcatcggg gctatcggcc      60
tcaaccgctg agacgcatct acatacccaa aagcaatggc aagaagcgtc cgctgggaat     120
tccaacgatg cgggatcgtg cgatgcaggc g

-continued

```
ggagccgacg cagaatcggg cctggtacat catgtccatg cacagccgcc aacgtggctg   1380
acgtgacgga agttgcccat ctgttgcacg gtggcgagaa cgttgtctgt gcttggggtt   1440
acaccggcgt agagaaacgg cctgagcacg acggtcggca agtgatctgg cagatctgcg   1500
cgacgcagca cctacaagca tttgagcaaa cgcagtgcgc cgtacaaggc caggcgcaag   1560
atcgagaagg ccaaagccca ggtacgtgcg aaggtcgaac atccgtttcg ggtgatcaag   1620
cgtcagttcg gttatgtgaa gacccgcttc cgtgtcctgg ccaagaatac ggcggaattg   1680
accacactgt tcgcgctgtc gaactctgtg atggtgcgc cggcaattat tgcctgctgc   1740
gggagaggtg cgcccgtgag tgacagaaaa ccagggcttt gcctcggtta ccaataaca   1800 cagcgactga aaatcgggca tttcggcatc cctaagccgc ccatttccga ctgatgagca   1860
acttgttcgg agtttcccta agcacaagc gcaagccatc agaaaagagt gcctgagtgt   1920
gctccaagat agcccgaaac taaggccgga catggaaaag accaagatca cccatgtgaa   1980
tgatggactt gtttttgtgg gccatcggat cattcgcaag cgtagccgat acggagatat   2040
gcgtgtgatc acgacgatcc gagacaaagc cagaagattc gcagcctcac tgacggcgct   2100
gctatcaggt aaccacagtg aaagtaagat cgacatggtt gaatcagtca accgaaagct   2160
taaaggctgg gcggcgttta tcaattcgtt gattcaaagc caaagtattc agctatatcg   2220
atcgtgtcgt gttttggaaa ctggcccatt ggctggctca aaaataccgc tcccaggttt   2280
gtcttgcctg ttcctggccc gccgatgaac accacattct gcgcggtatc tgtgaactcc   2340
aggttggacc gctccctatg ggcatcaaca atatctcgtg gccttggctg ggatacgcaa   2400
ctaaccaaaa tgcgcgactg gcgcatgcag cttccatatg ggagacgctg gaagcgtcgg   2460
aatagaccgt caatcagaag accttcttcg ctcccgtcga actgaaagcc tcaccgagtg   2520
cgaacgtcaa cgggaaaggc gcgcaaagac ttgccttgct cacctcgtca cgagcgtaca   2580
aacgctgtga gctggctgta cgggtgcgct gcttagcgtt ggttttttccg ttctgtgagc   2640 caacccccgtg atatcgtagt gcaggaccat gccgttaagg agggctgcct ggtcagcatt   2700
ttcagccagc gccggaagtt cctgcacttc ggccttgaac tggcgttcca atgcctggat   2760
atggccatag ggaggtacgc tttggcgtaa ggcgttgcat gcagcttggt gctgtcgagg   2820
ctgatggtgc ggagcttgag cagcttcatt tgccctgcca actccaccgc ctgaaggaag   2880
ttcccggcca agtcatcgag gaagcgctgc cggaagctgg ccggggtgac tcttgcggcg   2940
aggtggcgaa aagcgagcga gtcgtaactg gcgcgctcaa tcctggagct gggaactttg   3000
ccggtggcat aaccatagac catcgggctg agcacaatgc ctcgggggtg ataagccgct   3060
accgcgtccg ccatatgcct gagtgagggc gctaaggtcg ggccgctcaa tggcttcgag   3120
aataaagcgg gccaggtgat cttctgccat ctctcccgaa tgggtggaag cacatcaacc   3180
tgaccagcga ttacgtctgc gcagagccgc agactagagg tcgggaagtt ccggccgtta   3240
cggctgcccg gaaaacctca gtgtacgatt ttttcagtct cctctattcg acctgcgttg   3300
cgacgttcga tctgactagg gcgcagcggc aacatcggct gagtacgatc cagcgcctgg   3360
atttgggtta tttcgttaac cgacaacacc agagcgttat cctgcgggtt caggcagagc   3420
ccaaccacat gactacctct cggcaaaatg agggtcgtta ctaattttga acgtcttcaa   3480 gcgatgggt tttaggtcga aagctgccca ggcctgcgga acctaccaca tcgtaacccg   3540
agcatattcg gcccgcggcg gctaaaaaca cagaaatgag cggggtgacc cgatcgcctt   3600
tgatcgattc tccgctttca aaagcggcag gggctgaagt cagccggaaa tacccagacc   3660
```

```
aatcacaaca ttcatgctgg tgataaataa attcaactat gctttattga caaataaaag    3720
cacactcacc atcatcgcga atacaaatct tataaaatta agccggattt atgaaacttc    3780
tcatacagcc aaacaatcgc ctcattagct ttagtcccgg cgccaacctt ctggaagtgc    3840
ttcgcgagaa cggtgtcgct atttcctaca gttgtatgtc tgggcgttgc ggaacctgcc    3900
ggtgccgggt tacagatggt agtgtaattg attcggggac gggaagcggg ttaccacacc    3960
tcgtggacga gcattatgtg ctcgcctgtc ggtcagtact tactaacaat tgcgcgatcg    4020
aaatcccaga agccgacgaa atcgtcaccc acccggcgag aatcatcaag ggcactgtgg    4080
tcgctattga gtcgcccact cacgatatcc gtcgcctacg cgtacgcctc gccaagccct    4140
tcgagttctc acccggacag tacgcgacat tgcagttcag tcctgagcat gcgcgtccgt    4200
attcaatggc aggtctgcca gatgaccaag aaatggagtt ccacatacgc aaggtgccgg    4260
gtgggcgcgt aactgagtat gttttcgagc acgtccgcga aggtacaagc atcaaattga    4320
gcgggccact tggtacggct tatttacgtc agaaccacac cgggccgatg ctctgtgtgg    4380
gcggtggaac cggactagca ccggtgctgt cgattattcg cggcgcgctg aagttgggta    4440
tgacaaaccc catcctcctt tatttcggag tgcgcagtca gcaagacctc tacgacgcag    4500
agcgattgca taacctcgcg gctgatcacc ctcaactgac cgtacacacg gtaatcgcaa    4560
tgggcccgat taatgagagt cagcgagccg gtctagttac cgatgcgatc gaaaaagaca    4620
tcagttcgct ggctgggtgg agggcctatc tgtgcggtgc accagcgatg gttgaagcgc    4680
tttgcaccgt taccaaacat cttggaatat caccggaaca tatttatgcc gatgccttct    4740
atcccggtga atctgaatc gtcccttttcc ctcacctcgg tccattgagg actcatcagg    4800
aggatactca aataggcgca aataataaca gccgcgtcac tatgtgcggc agcgaaatgg    4860
tttccctctc cctcatttgc cccatcggag atagttttta tgacagaaaa atggattgaa    4920
gcagtcgccc tttgtgacat tccagaaggt gatgtcctcg gcgtgactgt cgagggtaag    4980
gatctggcac tgtacgaagt ggaaggcgaa atctacgcta ccgacgacct gtgcacgcat    5040
ggtgccgccc gcatgagcga tggttatctc gagggggcgag aaatcgaatg ccccttgcat    5100
caaggtcggt ttgacgtttg tacaagcaga gccctctgcg ccccccgtgac agagaacatc    5160 aaaacatatg cagtcaagat tgagaacctg cgcgtaatga ttgatttaag ctgagaattt    5220
ttaataggcg gcgccccgga ccatagagcg tgattatccc cattccatct ttttttaggt    5280
gaaaacatga attacaaaaa caaaatcttg gtaagtgagt ctgggctgac ccaaaagcac    5340
ctgattcatg gcggtgaagg gcttttccag cacgaactga gagccgtttt tgcgcggaac    5400 tggcttttc tcactcatga cagcctgatt ccttcccccg gcgactatgt taccgcaaaa    5460
atggggattg acgaggtcat cgtctctcgg caaagcgacg gttcgattcg tgccttcctg    5520
aacgtttgcc ggcaccgcgg caagacactg tgaacgcgg aagccggcaa tgctaaaggt    5580
ttcgtttgca gttatcacgg ctggggcttc ggctccaacg gcgaactgca gagcgttcca    5640
ttcgaaaaag agctgtacgg cgagtcgctc aacaaaaaat gtctgggtt gaaagaagtc    5700 gctcgcgtag agagcttcca tgggttcatc tatgcctgca tcgatcagga ggccccttct    5760
cttatggact atctcggtga cgctgcttgg tacctggaac ccatcttcaa acattcaggc    5820
ggtttagaac tggtaggccc tccaggtaag gttgtgatca aggccaactg gaaggcacct    5880
gcggaaaact ttgtgggtga tgcataccac gtcggttgga cgcacgcgtc ttcgctctgc    5940
acaggcgagt ctatcttctc gtcgctcgct ggcaacgcag tgctgccgcc tgaaggtgcg    6000
ggcttgcaaa tgacctccaa atacggcagc ggtatgggtg tgttgtggga cggatattca    6060
```

```
ggcgtgcata gcgcagactt ggttccggaa ttgatggcat tcggcggcgc taagcaggaa    6120
aggctgaaca agaaattgg cgatgttcgc gcccggattt atcgcagcca cctcaactgc    6180
accgttttcc cgaacaacag cgtgctgacc tgctcgggtg ttttcaaagt atggaacccg    6240
atcgacgcaa acaccaccga ggtctggacc tacgccattg tcgaaaaaga catgcccgag    6300
gatctcaagc gccgcttggc cgacgcggtt cagcgaacgg tcgggcctgc tggcttctgg    6360
gaaagcgacg acaatgacaa tatggaaaca gcatcgcaaa acggcaaaaa atatcaatcc    6420
agagatagtg atctgatttc caaccttggt ttcgggaagg atgtatacgg cgacgcggtc    6480
tatcctggcg tcgtcggaaa atcggcgatc ggcgagacca gttatcgtgg tttctaccgg    6540
gcttaccagg cacacgtcag cagctccaac tgggctgagt tcgaggatgc ctctagtact    6600
tggcataccg aactgacgaa gactactgat cgctaacaga cgagtcgacc atgatgatca    6660
atactcaaga agacaagctg gtatccgccc atgacgccga agagtttctt cgtttcttca    6720
attgccacga ctcggctttg caacaagaag ccaccacgct gctgacccgg aagcgcatc    6780
tgctggacat tcaggcttac cggacttggt tagagcactg cgtggggtca gaggttcaat    6840
atcaagtcat ttcacgcgaa ctgcgcgccg cttccgagcg acgttataag ctcaatgaag    6900
ccatgaacgt ttgcgacgaa aatttccagc aactgaaagt tcgagtcgag catcaactgg    6960
attcacaaaa ctggagcaac agcccgaagc tgcgctttac tcgcttcatc accaatgtcc    7020
aggccgcaat cgagctaaat gatgaagatc tgcttcacgt ccgctccaac gtcgttctgc    7080
accgggcacg acgtggcaat caagtcgatg tcttctacgc cgcccgggaa gacaaatgga    7140
aacgtggcga aggtggagtg cgaaaattgg tgcagcgatt cgtggattac ccagagcgca    7200
tacttcagac gcacaatctg atggtctttc tgtgatccgg tgaccacttt tacaaatggt    7260
gactgctacc gcggtcacca ttaatcaaaa gggaatgtac gtgtatgggc aatcaacaag    7320
tcgtttcaat aaccggtgcc ggctcaggaa tcggtctcga actggttcga tccttcaagt    7380
cggccggtta ttgcgtatcc gctctcgtac gaaacgagga gcaagaggcg cttctttgca    7440
atgaattcaa ggacgcactc gagatcgttg tgggcgatgt ccgagatcac gcaataaatg    7500
agaagctgat caagcagaca atcgctagat tcggtcatct cgattgtttc atcgcaaatg    7560
ccggtatttg ggattacatg ctgagcatcg aagagccttg ggagaaaatc tccagcagtt    7620
ttgacgaaat attcgacatc aatgtaaaga gctatttcag tggcatcagt gcagctctgc    7680
cggaactgaa aaagacgaac ggatcggtgg tgatgaccgc ttcggtgtcg tcccatgcgg    7740
tcggtggtgg tggttcttgc tacatcgcca gcaagcatgc ggtgttaggt atggtcaagg    7800
ctttggccta cgaattggct cccgaaattc gcgtgaacgc tgtctcgccg ggcggcaccg    7860
tgacgtctct gtgcggtcct gcaagcgccg gtttcgacaa aatgcacatg aaagacatgc    7920
ccggcatcga cgatatgatc aaaggcctca ctcctcttgg gtttgcagcc aagcccgaag    7980
acgtggtgga gccctatctg ttgctggctt cgcgaaagca gggaaaattc atcaccggca    8040
ccgtgattag cattgatggc ggtatggcgc tcggtcgcaa gtgagcttgc agccgatcaa    8100
aggttataga aacattttta ggtgacgccc catgaagaca aaactgttta tcaacaacgc    8160
ctggatcgat tccagtgacc agcagaccct cgagcgcaag cacccgtca acagcgaggt    8220
gatgactgag agcgcaaacg ccacggtgac ggacgcgata aggcggcgc aagtggccga    8280
ggaggcattc aagacctgga aggacgttgg accttcggag cgtcgccgcc ttctcctgaa    8340
ggtcgccgat gtcatggaaa gtaaaacacc caagtttatc gaagtgatgg ccatggaggt    8400
```

| | |
|---|---|
| gggagcttcc gctctttggg ccggattcaa cgtccatgcg tctgccaatg tgttccggga | 8460 |
| ggctgcctcg ctggccactc aaattcaggg cgaaaccatc ccaacggaca aagccgaaac | 8520 |
| gctctcaatg acactacgtc agccggtcgg cccgatcctg agcatcgtcc catggaacgg | 8580 |
| caccgcagtg ctgcggcac gagccatcgc gtatccgctg gtctgtggca acacggtggt | 8640 |
| gttcaaaggc tctgaattta gtcccgcgac gcatgccctg atcacccagt gcgtccagga | 8700 |
| agccgggctg cccgctggcg tgctcaacta tctcaactcc tcgcctgacc gttcgcccga | 8760 |
| gatcgccgac gcactgatct ccgcgaagga gatccgccgc atcaacttca cgggttcaac | 8820 |
| ccgcgtgggc agcattatcg cgcagaaggc cgcgcaacac ctcaagcgct gcctactgga | 8880 |
| gctcggcggc aagtccccgc ttattgttct ggatgacgca acattgacg cggcggtcaa | 8940 |
| ggcagcggtg ttcggtagct tcctgttcca aggtcagatc tgcatgtcca ctgagcgctt | 9000 |
| ggtggttgat gagaagattg ccgacgaatt tgtcgccaag tttgtcgaaa aaactaagcg | 9060 |
| cttgagcgtg ggcgacccgt gcgtaactgg cgactgcatc atcggcccaa tggtctcgcc | 9120 |
| aaattcgggc gagcggatca atggtttgtt caaggacgcg atcgataaag gggccaaagt | 9180 |
| tgtttgcggc ggcatggccc agggtgcggt catgccggcc acgatcctgg atcacgtgaa | 9240 |
| atctgacatg cggatctacg atgaggagac ctttggtccc atcacagtgg tgatccgttg | 9300 |
| caaaggggaa gcagaggcca tccgcattgc caacgacagc gtttatggtc tgtcgtcggg | 9360 |
| cgtgttttggc cgcgacatca accgtgctct gcgagtgggt atgtcgatcg aatatggttg | 9420 |
| cgtacacatc aacggctcga ccgtccagaa cgaggcgcag gctccttacg gaggtaccaa | 9480 |
| gaacaccggc tacgggcgct tcgacggccg tgccgtggtc gacgagttca cagagctcaa | 9540 |
| gtggctgacc attgagccat tcgagcagca atatcccttc tgaaagcact aactccaagg | 9600 |
| aatcaaacga tgagtaagca agctgcagtt atcgagctcg gatacatggg catctcagtc | 9660 |
| aaggatcctg atgcgtggaa atcgtttgcc atgaatatgc tgggtctgca agtactcgat | 9720 |
| gagggtgaga aggaccgttt ctatctgcgg atggattact ggcaccatcg tatcgtagtt | 9780 |
| catcacggcg gagaggacga cttggaatat ctaggctggc gtgtagccgg caagccggag | 9840 |
| ttcgaagctt tggggcaaaa gctcattgat gccggttaca agatccgtgt ctgcgacaaa | 9900 |
| gttgaggctc aggagcgtat ggtgttgggc ctgatgaaga cagaagatcc aggcggcaac | 9960 |
| ccgaccgaga tattctgggg gccccggatc gacatgagca atccgttcca tcccggccgc | 10020 |
| cctctgcacg gcaagtttgt gaccggtgac cagggcttag gtcattgcat cgttcgccaa | 10080 |
| accgacgtcg ctgcggccca taaattctac agcctgctgg gcttccgtgg ggacgtcgaa | 10140 |
| taccgcattc cattgcccaa cggcatgact gccgaactgt cattcatgca ttgcaacgcc | 10200 |
| cgtgatcact ccattgcgtt tggtgccatg cctgctgcca agcggctcaa tcacctgatg | 10260 |
| cttgagtaca cccatatgga agacttggga tatacgcatc aacagttcgt gaagaacgaa | 10320 |
| attgacatcg ccttgcagct tggcattcac gccaacgaca aggcgttgac gttctacggc | 10380 |
| gcaacgcctt cgggctggct tatcgagccc ggctggcgag gtgctacggc catagacgaa | 10440 |
| gcggagtatt acgtcggcga catcttcggc catggcgtcg aggcacctgg atatggcctg | 10500 |
| gatgtaaaac tgagttaaaa gcgattatgc gtacatcggg tttctgacgt tttctgcttt | 10560 |
| ctatacagcg caataacaat aacaactaag tgggaatatt aataatgata aaaaaaacgt | 10620 |
| ttctttacat gcctcgcttt acttgttcac tcagcaccgc atgggccgaa gaatcacctt | 10680 |
| ggacataccg catcggcatg agtaatattg cttttgatac aagcgccaaa gtgtacttgg | 10740 |
| gaggccagcg tgtgccggga ggaagcgctg acgcgagcaa taacaacgcg ctcacattcg | 10800 |

```
acttcggcta tgccatcaac gaccaatgga atgcacgttt gattgtcggt attccaccta   10860
caactaaagt taagggcgca ggcacacttc cgggcattca gctgggaaaa ataacttatg   10920
ctccaacatt actgacgtta aactataacc tcccagcttt tgggcccgtt cgtcctcaca   10980
tcggtgcagg agtcaattac acgcgaattt tggaaagcaa ggacgctaat ctaaaatcat   11040
tcgatgccga ccacgcttgg tcccccgcgc tgcatgttgg tgccgatatt gacgtgagtc   11100
gcaactggtt cgtcagcatt gatattcgga agttatacct gaaaaccgac gcatcaggtt   11160
acttagggcc acaggaggct aaagcaaagg taactcttga cccattgata acatcgatcg   11220
caatcggacg ccaattttga tgccccmttt taaggctctc tatctatcta actgcaaagg   11280
gtatttttat gttgaataaa attagtaaaa ccgcgcgtct taccgctgaa gatatcaatg   11340
gtgcctggac tataatgccc acaccgtcga cgcctgatgc ttctgattgg cgcacgacta   11400
acactgtgga cttagacgag actgcccgca tagttgaaga gctgattgct gctggtgtca   11460
acggtatttt gagtatgggt acctttggtg agtgcgccac gttgacctgg gaggagaaac   11520
gtgattatgt ttcgacggtt gtcgagacca ttcgcggtcg tgtaccttat ttctgcggca   11580
cgacggccct gaatacccga gaagtcattc ggcagacccg agagcttatc gatattggcg   11640
ctaacggcac catgctaggc gtgccgatgt gggttaagat ggacctgccc acagcggtcc   11700
agttctatcg tgatgttgca ggcgcggtac cggaggctgc cattgcgatt tacgccaacc   11760
ccgaagcatt caaattcgac ttccctcgcc cattttgggc agagatgtct aaaattcctc   11820
aggtagtgac tgccaagtat ctaggcatcg gaatgcttga cttggacctg aaattggcgc   11880
ctaacatccg cttccttcca cacgaggacg actattacgc ggccgcacgc atcaatcccg   11940
agcgcattac tgcgttctgg tcaagcgggg ccatgtgcgg cccggctacc gctatcgcgt   12000
tgcgtgatga agtggagcgg gccaagagta ccggtgactg gatcaaggcc aaagccatct   12060
ccgatgatat gcgtgcagcc gattcgacat tgtttccgcg tggcgacttt tcggagttct   12120
cgaagtataa tatcgggctt gaaaaggcac ggatggacgc ggctggttgg ctcaaggctg   12180
gtccctgccg tcctccctac aatcttgttc cagaagatta cctcgttggt gcacagaaat   12240
caggcaagtc gtgggccgcg ctgcacgcta aatacagtaa agaattaaag tagttcacct   12300
ccgcatgcct gagcgcgagg ggtgacgtaa acgccgagcg gtgcgggaag taagtgagtt   12360
agagttcatt tcttgtgcca ggcactgcta gatcagcaaa gttagctgat ctagcagtct   12420
cgaaaatttg ggcgaaagct gatcttagga atgcgggata aaggcagtac accgtaacga   12480
tcggggtgtg ccgttcatgt tgaacgacac cgctattgcg ccgacttctc ttcttcggag   12540
tgtttgattg tgattgtcga tttctatttc gatttttga gtccgttctc ttacttggcc   12600
aatcagcgtt tgtcaaagct gcgcaagat catggcctta ccacgtgtta taacgcgatc   12660
gatttggcgc gggtcaaaat agcgatcggt aacgttggtc catctaatcg cgacttggaa   12720
gtaaaattgg actatttgaa agtagatttg caacggtggg cccagcttta cggaataccg   12780
ctggtatttc cagctaacta caacagcaga cggatgaata ctgggcttta ttactcggag   12840
gccgaggtgc aggccgctgc ctatgtgaat gtagtattta atgcgatttg gggagaaggc   12900
atagcaccag atttggaaag cttgcctgcc ctggtatctg aaaagctagg ctgggatcgt   12960
agtgccttcg agcgctttct cagcagcaac gccgcaacag agaggtatga cgagcagaca   13020
catttcgcca tcgagcgcaa ggtgttcggt gtgccaacga tgttttttggg cgatgaaatg   13080 tggtggggga acgaccgtct gtttatgctc gagagcgcaa tggggcgctt gtgccggaaa   13140
```

-continued aatgccgatt taagtagttg atctgatcgt tatttgctcg atgagtcgct ttcaagatca 13200
gcggatactg aagtcagcta aatgcgggac tacttcaggc catgcttcag gggcggtcag 13260
ggcggactgg cgtgtgcacg gtagttgttg cgtgaggcat gtttttaaga tactattttc 13320
agtgcctgct gctctctctg ggttgagtgt gagggcgccg atagtctcaa atctcgcgtt 13380
gtacctgacc agagatacgg gtgtttatga tggcatcgct ggtacagcgc atgacgccat 13440
gctgcttcac ttcgagtgta ttcacgacct cgacgctagc aatctcaacg agccagatga 13500
tcgccagcca gggcggaagc tagtcgtgat tcgggttttc tacgttgtac ccgaatgcaa 13560
tcctggtctt aacggtccac gccttaaacg tggaatgcca aatctgcgat gtcgacattg 13620
gcccatataa tgttttggct ctcctctagt cagaaatcag taaggtgtgc atggtgataa 13680
ctggtcaagc cgggaatcag cggaatcgct gcgctggcgc cactggcgat caaacagcgg 13740
tcaaatacta ccattgaact ggcctaagag ggtgtggaca aaataaagta aacttcttgc 13800
ctcctttcta tgcagcattg agccatgcct aaaactggac gcccaccgta atcgctacgc 13860
accattaccc tctgctgacc aggctcgctc atacgcagcc ttattccagt caagccgaac 13920
tggcgcaaga ttccatgcag aaacgggcat caccgcgcat cccgacacct ttgcaaaagc 13980
gctgagactg gccgggatcg ttcgagtaaa ggagcgtgcc aaaggtagct tccagcctcc 14040
cgagcctcgt aagtcttatg gctataccga ggcacaccgg cgtcagttgc cggagcaacg 14100
ctatcccagt tgcctgactg atgcagaatg gacgttggtc gctgatttat ttgaagtctc 14160
gggaggtcgc ggcgtaccgc tcgccactcc cgacgcactc ttttggaagc ctgctgttat 14220
gtcgtgcgca cagggtgctc ctggcgaatg ctgcttcgcg agtttcccta ttgggacaat 14280
gtctataaaa cctttcggcg ctggagcgtc agggcaagtt tgagcaaatg cacgaccggc 14340
tccgtgccca atggcgagag cgggtggatc gtgatgaacg gccgtcagcc gctgttctgg 14400
attcccaatc aacgcgcacg tctccccaag gcggtgaaag cggttacgac gcaggcaaaa 14460
ag 14462

<210> SEQ ID NO 10
<211> LENGTH: 12808
<212> TYPE: DNA
<213> ORGANISM: Artificial Sequence
<220> FEATURE:
<223> OTHER INFORMATION: A modified DNA molecule encoding valine at the position corresponding to the F352 amino acid in NDO.

<400> SEQUENCE: 10
gtcgacgcat gatgcaggac tgggccgatc gcctcgacct cttcgagcag aaccaggtcg 60
aggcggccag catgccgctc accgtgcatc tggaaggtgt gcccgcattc ccgagtgagc 120
aaaccgcaag cgcgccctct acgccggttg ccgcttcgcc aagcctgctc gtgacgaagc 180
cgggtgacgc catgccgttg gtttctgccg ccgcacatcg gctgccggca gtgccgcccc 240
agcgatcggc cgcgccgctg gtgccttcgg acattcagcg cgagagaatg gatttgttcg 300
atgtcttcga agcgccgcac aaccttcccg tcgctgcgtt tgccaagatg gcgggcaaat 360
ctcgcaggtg gatcagctac gagatccagg cgggcaactt gctggcgttg aacgtgggca 420
accgcggcca gcgcgtgccg gactggcacc tcgacccgct caagcacgag ctgatccagt 480
ctgtcctgaa gctgaccagg ggtgcggacc cttggcagat ctaccatgca ctgctgcagc 540
cgcgctcgat gctgcggggg cgctcggcac tggagggcgt gactgccagc aatctcgaca 600
agctcgtcat ggccgtgagc acagcggtga aggaaagcga atggaccccg ctgcgggtcg 660

-continued

```
gtggtcgtgt agtcaaacaa cgggccggta agggatggcc tggacattat tcatattagt      720
gatactaata ttcatttatg gtttattgac tattagaata cagtcaatga tcatggaacc      780
ataaagcata taaataaaga agctagatct atggaacttc tcgtactacc gaacaatcgc      840
cgcttgcctt ttgattccgg tgccaacctt ttggaagtgc tccgtgagca ccgtgtgggt      900
atttcctaca gctgtatgtc tggacgatgc ggtacttgcc gctgccgagt tatagatggc      960
agcgtcatta gttcggcggc gaaaagcggt gactcaaatc gcatcgaaga gcattatgta     1020
ctcgcctgtc agtcagtgct caccagcaat gcgcaattg agatcataga ctcagacgac      1080
atagtcactc acccggcgcg aatcatcaaa ggcatggttg tcgccgtcga gtcgcccact     1140
cacgatattc gccgcatccg cattcgcctc gccaagccct tcgagttctc acccggacag     1200
tacgcgatgc tacagttcag tcccgaacat gtgcgtccat attcaatggc tggtctgcca     1260
gatgaccaag aaatggagtt ccatatccgc aaagtgccgg gcgggcgtgt cacggagtat     1320
attttcgagc acgtccgcga aggtacaagc attaagttga gtgggcctct tggtacggcc     1380
tatctgcgtc aggctcacac cgggccgatg ctgtgtgtgg gcggcgggac cggactcgca     1440
ccggtgctgt cgattgttcg cggcgcgctg aagtcgggaa tgacgaaccc catccacctt     1500
tatttcgggg tgcgcagtca gcaagaccttt tacgacgcag accgattgaa ccaactcgcg     1560
gctatccacc ctcaactgac tgtccataca gtgatcgcga cgggcccgat taatgagggc     1620
cagcgggccg gcctaattac cgatttgatt gaaaaagaca ttccctcgct ggctgggtgg     1680
agagcctacc tgtgcggcgc accagcgatg gttgacgctc tatgcaccgt cgccaaagat     1740
cttggaatat cgcccgagca tatttatgcc gacgccttct atcccagcgg ggtctgaatt     1800
gccccgaccc ttcacctctg tacatcgaga attcatcagg aagacactta aatgagcatc     1860
actaacaaca gccgcgtctg aatatttagg acagctggat gatctctaac tccatcatta     1920
ccccatttga agatagcttt atgacagaaa atggattga cgcagtcgct ctttatgaaa      1980
tccctgaagg tgacgtcctc ggcgtgacag tcgaaggtaa ggaactagcg ctgtatgaag     2040
tggaaggcga aatctacgct accgacaacc tgtgcacaca tggtgctgcc cgcatgagtg     2100
atggctttct agaaggcaga gaaattgaat gtccttttgca tcaaggtaga tttgatgttt     2160
gcacaggcag ggccttgtgc gcccctgtga cacagaacat caaaacatac ccggtgaaga     2220
ttgagggcca gcgtgtgatg attgatttga gctgagaatt ttaataggag gcaccccgga     2280
ccctagagcg taatcccccc cattcgatct cttgaggtga aaatatgaat tacaaaaata     2340
aaaacttggt gagtgaatct gggctgaccc aaaaacacct gattcatggc gacgaagaac     2400
ttttccagcg cgaactggaa accatttttg ctcggaactg gcttttcctg actcatgaca     2460
gcctgattcc gtccctggc gactatgtta cggcaaaaat gggggttgat gaggttatcg      2520
tctccaggca gaacgacggt tcgattcgtg ctttttctgaa cgtttgtcgt caccgtggca     2580
agacgctggt acacgcagaa gcaggtaatg ctaaaggttt cgtttgcagc tatcacggct     2640
ggggcttcgg cgctaacggt gaactgcaga gcgtcccgtt tgaaaaagaa ctgtatggcg     2700
aggcgctcga caagaaatgt atgggattga agaagtcgc tcgtgtagag agcttccatg      2760
gcttcatcta tggttgcttc gatgaggaag ccccttctct caaagactac atggggacg      2820 ctggctggta cctggagcct atgtttaagc attccggagg gctagaactg atcggtcctc     2880
caggaaaggt cataatcaag gctaactgga agcgcccgc ggaaaacttt acggggatg       2940 cgtaccacgt gggttggacg catgcgtctt cgcttcgctc agggcagtcg gtcttctcgt     3000
```

-continued

```
cgttagctgg caacgcagct ttgcccccag aaggtgcagg tctgcaaatg acctccaaat    3060
acggcagcgg catgggtgtg ttgtgggacg gatattcagg cgtgcacagc gcagacctgg    3120
ttccggaatt gatggccttc ggcggtgcta agcaggaacg gctgaacaaa gaaattggcg    3180
aggttcgcgc acgaatctat cgcagccacc tcaactgcac cgttttcccg aacaacagtt    3240
ttctgacctg ctcgggtgtc ttcaaggtat ggcacccgat cgacgcaaat accactgagg    3300
tatggaccta cgccatggtc gaaaaagaca tgcccgagga tctcaagcgc cgcttggtcg    3360
acgcggttca gagaacggtt gggcctgctg gcttctggga aagcgacgac aacgacaata    3420
tggaaacggt atcgcaaaac gccagaaaat atcagtccag agatggcgat ctggtttcca    3480
acctgggttt cggcggggac gtatacggcg acgaggttta tcctggcatc gtcggcaaat    3540
cggcgattgg cgagaccagt tatcgtggct ctatcgggc ttacgcgcg cacatcagca    3600 gctctagctg ggctgaattc gaggatgtct ctaaaaattg gcataccgaa ctggcaaaga    3660
ctactgatcg ctaacagacg agagggacca tgatgattaa tattcaggaa gacaagcttg    3720
tctccgccca cgacgccgaa gagtttcttc gtttcttcaa ttccggcgac gaggctttgc    3780
aacaagaagc taccacgttg ctaacccggg aagcgcatct tttagacatt caggcttacc    3840
gcgcctggtt agagcactgc gtggactcag aggtgaaata tcagattatc tcacgcgaac    3900
tgcgctcagc ttccgagcgc cgttaccagc tcaatgaaac catgaacatt ttcaacgaga    3960
attatgaaca actggaagtt cgcgtagcgc atcaactgga tccgcaaaac tggggcaata    4020
gtccaaaggt gcgctttact cgtttcatca caaatatcca ggctgcaatg gacgaaaatg    4080
aagatttgct tcacattcgc tccaacctaa ttgttcaccg agcacgacgc ggcaatcaag    4140
tcgatgtctt ctatgccact cgggaggata aatggaagcg cggcgaagat ggagcgcgta    4200
agttggtcca acgattgatt gattatccag agcgcacatt ccagacgcac aatgtgatga    4260
tctttatgtg acccaataat cgcctttaca aatggtgact gctacaagcg gtcccattgt    4320
tcaaaaggaa atttatgtgt atgagcaatc aacaagtcgt ttcgataacc ggtgctggct    4380
caggaattgg tctcgaactg gttcgatcct ttaagtccgc cggttattgc gtatccgctc    4440
tcgtacaaaa cgaggagcaa aaggcgagcc tttgcaatga gttcaaggac gcactcgaga    4500
tcgtcgtggg cgatgtccgg gaccacgcaa caaatgagaa gctgataaag caaacaaccg    4560
atagattcgg ccatctcgat tgtttcattg caaatgccgg tatttgggat tacatgcttg    4620
gcatcgaaga gccttgggag aaaatatcga gcagttttga tgagatattc aacatcaatg    4680
tcaagagcta tttcagcggt atcagggccg ccctgcagga actgaaaaag actagcggat    4740
cagtggtgat gaccgcttca gtgtcgtccc atgcggtcgg tgctggtggt tcttgctaca    4800
tcgccagcaa gcatgcggtc ctgggcatga tgaaagcttt ggcttacgaa ttggctcccc    4860
acattcgcgt caacgccgta gcaccgggcg gcactgtgac gcctctgagc ggtcccgcaa    4920
gcgccggctt cgacaaaact cacatggaaa acatgcccgg tatcgaggac atgatcaagg    4980
gtctaacgcc tcttggaatt tcagccaagg ccgaagacgt agtggcaccc tatttgttgt    5040
tggcgtcgcg agatcaaggg aaattcatta ccgggactgt cattaatata gatgagggga    5100
tggcgctcgg tcgcaagtag gtttgtcgcc tatcttgaaa aataactaa atttctggta    5160 aaaccgcatg aatacaaaat tgtttatcaa caatgtctgg atcaattcca gtgaccaaca    5220
gaccttcgag cgaaagcacc ccgtcagtgg tgaggtgatg acggagtgtg caaactccac    5280
ggtgatggat gcgttaaagg ccgcgcaagc tgcccaagag gctttccaga cctgaaagac    5340
tgttggacct tcggagcgtc gccgccttct gctgagggtc gctgaggtta tggaaagtaa    5400
```

```
aacacccgag tttatcgaag tgatggccaa ggaggtggga gcctccgctc tttgggccgg   5460
cttcaatgtc cagatgtcag ccaatgtgtt ccgtgaagcg gcatcgctgg ctacacaaat   5520
tcaggggggaa actattccga cagacaagtc tgacacgctc tcaatgacgc tacgtcagcc   5580
ggtcggtccg atcctgagca tcgtgccgtg aacggcacc gcagtgctgg cggcacgagc    5640
catcgcttat ccgctggtct gcggcaacgc ggtggtattc aaaggttctg agtttagtcc   5700
cgcgacgcat gccctgatca cccagtgcgt gcaggaagcc gggctgcctg ctggcgtgct   5760
caactatctc aactcttcgc ctgaccgttc gcccgagatc gccgacgcac tgatctcagc   5820
caaggagatc cgacgcatca acttcacggg ctccacccgc gtgggcagta ttatcgcgca   5880
gaaggccgcg caaacctca agcgctgcct gctggagctc ggtggcaagt ccccacttat    5940
tgttctggat gatgcagaca tcgatgcggc ggtcaaggca gcggtgttcg gtagcttcct   6000
gttccaaggt cagatctgca tgtccactga gcgcttgatc gttgatgaga agatagccga   6060
cgaatttgtc gcaaaatttg tcgaaaaaac taagcgcttg agcgcaggcg acccgtgcgt   6120
aactggcgac tgcatcatcg gcccgatggt ctcgccaaat tcgggtgagc ggatcaatgg   6180
tttgttcaaa gacgcgatcg acaaagggggc aaaagttgtt tgcggcggct tggcccaagg   6240
tgcgctcatg ccggccacga tcctggatca cgtcaaatct gacatgcgga tttacgatga   6300
ggagaccttt ggtcccatca ccgtggtaat ccgttgtaaa ggcgaagcag aggccgtccg   6360
cattgccaac gacagcgtct atggcctgtc gtcgggcgta tttgggcgcg acatcaaccg   6420
cgctctacgc gtgggtatgt ccatcgaata tggttctgta cacatcaacg gttcgaccgt   6480
ccagaacgag gcgcaggctc cttacggagg caccaagaac accggctacg gcgcttcga    6540
cggccgtgct gtaatcgacg agttcacaga gatcaagtgg ctgaccatcg aacctttcga   6600
gcagcaatat cccttctgat aagcactaac tcccaggaat caaactatga gtaagcaagc   6660
tgcagttatc gagctcggat acatgggtat ctcggtcaag gaccctgatg cgtggaaatc   6720
atttgccacg gatatgctag gtctgcaagt tcttgatgag ggtgagaagg accgtttcta   6780
tctgcggatg gattactggc atcatcggat cgtagtccat cacaacggac aggacgactt   6840
ggagtaccta ggctggcgtg tagccggcaa gccggagttc gaagctctgg gtcaaaagct   6900
tattgatgcc ggttacaaga tccgcatctg cgacaaagtt gaggctcagg agcgtatggt   6960
gttgggtctg atgaagacag aagatccggg cggcaacccg accgagatat tctggggccc   7020
ccggatcgac atgagcaacc cgttccatcc cggtcgcccc ctgcacggaa agtttgtgac   7080
cggtgaccaa ggcttgggcc attgcatcgt tcgccaaacc gacgtcgcag aagctcataa   7140
gttttatagc ctgctgggct tccgtgggga cgtcgaatac cggattccgt tgcccaacgg   7200
catgactgcc gaactgtcgt tcatgcattg caacgcccgt gatcactcca ttgcttttgg   7260
tgccatgccc gctgccaaac gactcaatca cttgatgctt gagtacaccc atatggaaga   7320
cttgggatac acgcaccaac agtttgtaaa gaacgaaatt gacattgcct tgcagcttgg   7380
cattcacgcc aacgacaagg cgttgacgtt ctatggtgca acgccttcgg gctggctcat   7440
tgagcccggc tggcgaggtg ccacggccat agatgaagcg gagtattacg tcggcgacat   7500
cttcggccat ggcgtggagg ccactggata tggcctggat gtaaaactga gctaaagatg   7560
cgcgctcgtt gggcgaggct ctagtccagc atcttcatac gcaaccaacc ttgcagggcg   7620
atgagatcaa aggacgttaa agcgaagggg aagtggttcg ggccatgcgc ataccgatcc   7680
atgacatttg tttcatagta tataggtaga taggtgaatc aagcgcttag tcaactagtg   7740
```

-continued

```
gacacatctg ttccatgagg ctatctacta tctattcaaa acaagaatga taaataggat    7800
gaaaataata atgataaaaa gaacgatttg tcttgtgtat cctctattct gtttggcaag    7860
ccccacatgg gccgaagagt cgccttggac gtaccgtatt ggtatgacta atgtagcttt    7920
cgatgctagc gcaaaagtat acttaaatgg tcagcgggtg ccaggaggaa gcgctgatgc    7980
gagcgataac aacgcgctta cattcgactt cggctacgcc atcaacgacc agtggaatgt    8040
acgtgcgatt gtcggtattc cgcctacaac taaagtgacg ggcgcaggca cacttcctgg    8100
tatccagctg gggaaaataa cttacgctcc aacagtatta acgttgaact ataacctccc    8160
cgctttgggt cccgttcgcc ctcacatagg tgcgggagtc aattacacgc ggattttga    8220 aagtcgggac gctaatctaa atcgttcga tgccgaccac gcttggtccc ccgcgctaca    8280
tgttggtgcc gatattgacg ttaaccgtgg ttggttcgtt agcattgata tccgaagtt    8340 atacctgaaa accgacgcat cagggtactt ggggccacag gaggctaaag cacgggtaac    8400
tcttgaccca ttactaactt cgatcgcgat cggacgccaa ttctgatgat tctgtttaaa    8460
gttctttatc tatctaaccg caaaggtgt ttccatgtcg aataaaatta tgaaaacgtc    8520
gcgtcttacc gccgaagata tcaacggcgc ctggactata atgcccacac cctcgacgcc    8580
tgatgcttct gattggcgca gcactgccac cgtggactta aagagactg cccgcatagt    8640 tgaagagctg attgcagctg tgtcaacgg tattctaagt atgggtactt ttggtgagtg    8700
cgccacgttg acctgggatg aaaaacgtga ttatgtctcg acgattgtcg agaccattcg    8760
tggtcgcgtg ccttatttct gtggcacgac agccttaaat acccgagaag tcatccgcca    8820
gacccgagag cttatcgata ttggcgccaa cggcactatg ctcgggtgc cgatgtgggt    8880 gaagatggac ctgcctacag cggttcagtt ctatcgtgat gttgcagatg cggtaccaga    8940
ggctgccatt gcgatttacg ccaaccccga agcattcaag ttcgacttcc ctcgcccatt    9000
ctgggcagag atgtccaaaa ttccgcaggt agtgactgcg aagtatctag gcatcggaat    9060
gcttgacttg gacctgagac tggcacccaa catccgcttc cttccccacg aagatgacta    9120
ttacgcggcc gcacgcatca atcccgagcg cataaccgcg ttctggtcaa gcggggccat    9180
gtgcggcccg gctaccgcca tcatgttgcg tgacgaagtg gtgcgggcca agagcaccgg    9240
tgactgggcc aaggccaaag ccatctccga tgatatgcgt gcagccgact cgacattgtt    9300
tccgcgtggc gacttttcgg agttctcgaa gtataatatc gggcttgaaa aggcacggat    9360
ggatgcggct ggttggctca aggctgggcc ctgccgtccg ccctacaacc ttgttccaga    9420
agactacctc gctggtgcac agaaatcagg caaggcttgg gccgcgctgc acgctaaata    9480
cagtaatgaa ttgaagtagt tcacctccgc agacctgagt gacagggtgg cgcagacgct    9540
gagggtgcag gaattaagtg agctaaagca catttcttgc gccaggcatt gccagatcag    9600
caaagtttgc tgatctggca gtttcaaaaa tttgggcgaa agctgatatc aggaatacgg    9660
gataaaggca gtgcaccata acgacggggg cgtgccattc gtgatgaacg atttgctat    9720 tgtgccgact tctgttcttg gagtgtttga ttgtgattgt cgattttat ttcgattttt    9780 tgagtccgtt ctcttacttg gccaaccatc gtttgtcaaa gcttgcgcaa gactatggct    9840
tttccattcg ttattacgca atcgatttgg cgcgagttaa aatagccatc ggaaacgttg    9900
gtccatctaa tcgcgacctg atagtcaagc tggactattt gaaagtagat ttgcaacggt    9960
gggccgagct ttacgaaata ccgttggtat tcccagctaa ctacaacagc cgacggatga   10020 atactggggct ttattactcg ggagccatgg cacagactgg tgcctatgtg aatgtagtat   10080
ttaatgcggt ttgggggagat ggcatagctc cagatttgga aagcttgcct gctctggtat   10140
```

-continued

```
ctgaaaaact aggctgggat cgtagcgcct tcgaggactt tatcagcagc gatgccgcaa    10200
cagagaggta tgacgagcag acacatgccg cgatcgaacg caaagtgttc ggtgtgccaa    10260
cgatgttttt gggcgatgaa atgtggtggg gaaacgaccg tctatttatg ctcgagaacg    10320
cagtgggagg tgcgcctgta aatggagaat agtcgctacg gagcgcttgt gccggctaaa    10380
tgccgatata agtggttgac ctgatcgtta tttgctcgat acagcgcttt caaaatcagc    10440
ggctactgaa gtcagataaa aatgcgggac tacttcaggc atcctgtgcg acacaaagtt    10500
ttacctgtaa ttgtccacct attccgagtt tggaatggta gctgactcgc tatgcgacca    10560
gcgatagcct aacaagacat gcatcactgg taacggtggg gtgtgaagct cctgcaacaa    10620
tgtagcccct tgatgtgtgt atttgctgcg aggtgaagca cagatgctcg gagccgtacc    10680
ggcttgtggc gctaggctgg caagtatgag caacgtaagt gggggttggg gcgcaatggg    10740
aaccaaaaac caacgcaagc cttaccagcg tcgttcggtg ccttcctccc atgcctccgc    10800
ctcgataaag cagctgcgca tatcggcttc ctggctgatc tcggttagta ggtcatgcaa    10860
ggtcttgtcc agcgcctcgt cgctccgata cggaatggtc agctcgtaat ggccggtctc    10920
cgaccgcttc atgccgtagg gctccaggca gtagcgctcg atgttctccg tggcccgctt    10980
ccgaccgcgc atgaacttgc tgttgttcac caccgccagg cgcagggtga cggtggccac    11040
ccgctcgacg gttgactctg ccggtgacgc gatattgcgc ttttgacctc gcgccagggc    11100
gctcttctgg tacgtcccga tctcgacgcc acggtggcgt aggtagctgt acagggtgct    11160
cttggagatg tgcaacttct cgccgatggc gctgacgctc aggcggccct cgcggtacag    11220
ggtctccgcc gccatggcgg tggcctcggc cttggctggc aggcccttgg gacggcgacc    11280
gatccggcct cgagtccgtg ccgccgacag gcccgcctga gtccgctcgc ggatcagctc    11340
gcgctcgaac tgaacaggtt gaacaccagg cgatcttggg cgtgggtgct gtcaatgggg    11400
tcgttcaggc tctgcaagcc gactttgcgt gcagccagct agccgaccaa ctcaaccagg    11460
tgcttgagcg agcgaccgag gcgatccagc ttccagatca ccacggcatc gcccgctcga    11520
acatgggcta gcaacttgtc caactccggc cgcgcgcttt ttgcgccgct ggcgatgtct    11580
tgatagatgc gttcgcaccc ggcctgtttc agggcatcga cctggaggtc ggcgttctaa    11640
tcccgagtgc tcaccgcgt ataaccgatc ttcataaaaa gtaccgttta cttgactgca    11700
ttagtaatag ttgaactttg attaagctta ccagttattt gaaccctagc gcaggtgtaa    11760
gcgtccagcc gccccacctc tactcagctt gatgaaccga ggggcagtag ttcatcaatc    11820
cggctgttag ggaaactctg aagaagactt cctgattttg gcaaaatgcc cggatttcac    11880
ccgccgagtt ttccaatgaa gcagatgacc ttcctcgacg ccgagtatgc cggtaagcgc    11940
aaacagaccc gcaaagagct gttcctgatc gagatggatc gggtggtgcc gtggaagggt    12000
ttgattgcct tgatcgatcc gcattacccc aagggtgagg gtggcccgcc agcctatcca    12060
ctgacggcaa tgctgcgggt tcatctgatg cataagtggt tcggctacag cgacccggcg    12120
atggaggaag cgctgtacga gacgaccatc ctgcgccagt ttgccgggtt gagcctggag    12180
cgcattccgg actaaaccac catccccaac ttccgccggc tgctggagaa acacgaacta    12240
cctaccggca tcatgtttgc tgaattttcg ccttttggctt tgagtgcggc attcaaccga    12300
tacaggtgtg gcatgacacg ccaaagaaat caaccttggc ggctagaaca cttgtcgatg    12360
aagcgaacaa tccgcaaacg ttaaggctac caggaaaaac ccaggatgcg gtagccgata    12420
gcccgcgcgc gcattggtct ccttccgtcc aagagtgtca aaggatattg gactaatgca    12480
```

-continued

```
gcatgcctcg accacatggc cgtggtccgt tcatctgttg gccatacgtc tatcgaatcg  12540
gacgcgggcg gcgacgacct cgggttgttg gcgttcggcc cagtcgatga gctcagtcag  12600
ggacggcatc agcgaagtcc cgagcggggt gagcccgtag cgcacagatg gggtgtcga   12660 gggcgttacc tcgcgccaga tgagtccgtc gcgttcgagg tgacgcagcg tctcggtcag  12720
catccggcgc gaaatgtcgg gcacggcgcg ggccagcgca ttgaatcgtt gcggaccctg  12780
cgacaaggtg accaggatca gcgtcgac                                     12808
```

```

<210> SEQ ID NO 11
<211> LENGTH: 15024
<212> TYPE: DNA
<213> ORGANISM: Artificial Sequence
<220> FEATURE:
<223> OTHER INFORMATION: A modified DNA molecule encoding valine at the
      position corresponding to the F352 amino acid in
      NDO.

<400> SEQUENCE: 11

```

```
atcgtcctta agcgccgcac gcagccgttt aagtgaattg ctgacggcag gctgcgtcag     60
ccccagtttt tcgccggccg tcgatacgct ccggtcgagc agtagctggt tgaagaccac    120
cagcagattc aagtcgatgt cgcgcagatc catgatgcct caccattatt catgctggtg    180
attttaacta tcagacttga tctatagcgc tataccgatc gacgcgccag aatcgcagcc    240
attcggagac aactgaaaaa agagcttgca tggaactggt agtagaaccc ctcaatttgc    300
atctgaacgc ggagaccggc agcaccctgc ttgacgtgct caggtccaac gaggtcccca    360
tttcttatag ctgcatgtcg ggccgctgcg gcacttgccg ttgccgtgtg attgccggcc    420
atcttcgcga taacggcccc gagacagggc gcccgcaggc aggaaaggga acctacgttc    480
tggcctgtca ggcggttctg accgaagact gcacgatcga gattcctgaa tctgacgaga    540
tcgtggttca cccggcgcgc atcgtcaagg ggacggtcac agcgatagac gaagccaccc    600
atgacatccg gcgcctgcgc atcaaactgg ccaaaccgct tgagttcagc cctggccagt    660
acgcaacggt gcagttcacg cccgaatgcg tccgcccata ttcgatggcc gggctgccta    720
gcgatgcgga aatggagttt cagattcgcg cggttccggg cgggcatgtc agcaactacg    780
ttttcaatga actgtccgta ggcgcttcgg tgcggatcag cggcccccctc ggaacggctt   840 atctgcggcg cacgcacacc ggccccatgc tttgtgtggg gggtggaaca ggtctggcgc    900
ccgtcctttc gatcgttcga ggcgcactgg aaagcgggat gagcaacccc atccatctgt    960
acttcggtgt gcggagcgag caggacatct atgacgagga acgccttcac gcattggctg   1020
caaggtttcc gaatctcaag gtgaatgtcg ttgttgcaac aggccctgcc ggccctggtc   1080
gtcgatccgg cctggtcacc gatctgatcg gccgtgactt gcccaatttg gcgggatggc   1140
gcgcctacct gtgtggcgct ccggccatgg tcgaggccct gaacctgctc gttgctcgcc   1200
taggcatagt acccgggcac atccatgccg atgcgttcta tcccagcggc gtctgagcga   1260
aggcaccatg cgaacccaat tcaacccaag gataccaagc catgagtgaa ccccaacgat   1320
taaaacccgt gtttccccaa gatccgaaat ggccgggcga aggtagcagc cgcgttccct   1380
tctgggccta cacccgcgaa gacctgtaca agcgcgaatt ggagcgcctg ttctatgcaa   1440
accactggtg ctatgtaggc ctggaagccg agattccgaa tccaggcgac ttcaagcgaa   1500
cggtgatcgg tgagcgctcg gtcatcatgg tgcgtgatcc ggatggcggc atcaacgtgg   1560
tggagaacgt ctgcgcccac cgtggcatgc gcttttgccg cgagcgccac ggcaacgcca   1620
aggacttctt ctgcccctac caccagtgga actacagcct caagggtgac ctgcagggcg   1680
```

-continued

```
tgcccttccg ccgtggcgtc aagcaggacg gcaaggtcaa cggcggcatg cccaaggact    1740
tcaaactcga agaacacggc ctgaccaagc tcaaggtggc cgcccgaggc ggtgcagtgt    1800
ttgcctcttt tgaccacgat gtcgagccct cgaggagtt cctgggccca accatcctgc     1860
attacttcga ccgcgtcttc aacggccgca agctcaagat cctgggctac cgccgccagc    1920
gcatcccggg caactggaag ctgatgcagg agaacatcaa ggaccsctac cacccgggcc    1980
tgctgcacac ctggttctcg accttcgggc tctggcgcgc cgacaacaag tcggaactga    2040
agatggacgc caagttccgc cacgccgcaa tgatctccac gcgcggtcag ggcggcaaga    2100
acgaggaggt cgtgtccggc gtggacagct tcaaggaaca gatgaaggtg aacgacccgc    2160
gcctgctcga catcgtgccc gagccctggt ggggcggtcc gactgcggtg atgaccacga    2220
tcttccccag cgtgatcatc cagcagcagg tcaacagcgt atcgacccgc cacatccagc    2280
ccaacggtca cggctccttc gatttcgtct ggacccactt cggcttcgag gacgacaacg    2340
aggagtggac ccagcgccgc ctgatccagg ccaacctgtt cgggccggcg ggcttcgtgt    2400
cggccgatga cggcgaggtg atcgagtggt cgcaggaagg ctttgagcaa aaaccgacgc    2460
accgcaccgt gatcgagatg ggcggtcacg aaatcggcga cacggaccac atggtcaccg    2520
agacgctgat ccgcggcatg tacgactact ggcgcaaggt gatgggggaa taaacatggt    2580
cgacttcaaa acctatttcg aactgctgaa cctgtacagc gactacgcca tggtgtgcga    2640
ctccgccaat tgggagaagt ggcctgattt cttcatcgag accggcacct accgcctgca    2700
gccgcgcgag aactttgagc agggcctgcc gctgtgcctg ctggcgctgg agagcaaggc    2760
aatgatccgc gaccgggtgt acggcgtcaa ggaaaccatg taccacgacc cctactacca    2820
gcgccacatc gtgggcacgc cgcgcgtgct gtcagtggag cgtgacgcgg atggcgagcg    2880
catcaccgcc gaagccagct atgccgtgat tcgcaccaag tacgacggcg attccacgat    2940
tttcaacgcc ggctattacc gagacgtgat cgtgcgcacg cccgagggcc tcaagctgaa    3000
gtcgcgcctg tgcgtttacg acagcgaaat gatccccaac tctgtgatct atccaatctg    3060
aggcgacgca catgactcag aactggattg atgcagcttg tcttgacgac atccctgaag    3120
gcgatgtggt cggcgtcaaa gttaacggca aggaaattgc gctctacgag gtcgaggggg    3180
agatttatgc caccgataac ctgtgcacgc acggcgctgc gcgcatgagc gatggctttc    3240
tcgaaggccg ggaaattgaa tgccctctgc accaaggtcg atttgatgtc tgcacaggca    3300
aagccttgtg caccccctg acaaaggaca tcaaaaccta ccccgtcaaa attgaaaaca    3360
tgcgcgtgat gctcaaaatg gagtaagact gctttcaatc aggaggctga attcggacca    3420
atcaaccaaa ccatccaatc cacccattag ccaaaaaacg gagacattaa tcatgattta    3480
tgaaaatttg gtgagtgaag cagggctgac gcaaaagcac ctgattcatg gcgacaaaga    3540 actttttccag cacgaattga agaccatctt cgcgcgaaac tggctttttc tgacccatga    3600
cagcttgatt ccctcccccg cgactatgt cacagccaaa atgggtgtcg atgaagtcat    3660
cgtctcccgc cagaacgatg gctcggtgcg agccttttg aatgtttgcc gtcaccgggg    3720
caagacacta gttcacgctg aagccggaaa tgcgaaaggc tttgtgtgca gttaccacgg    3780
ctggggcttt ggctccaacg gcgaactgca aagcgttccc tttgaaaaag agttgtacgg    3840
cgatacgatc aaaaagaagt gcctgggctt gaaagaagtc ccccgcatcg aaagctttca    3900
tggcttcatt tacggttgtt ttgatgcaga ggccccacg cttgtcgatt atctgggtga    3960
tgcagcctgg tacttagaac ccatcttcaa gcactctggt ggcctggaac ttgtaggccc    4020
```

-continued

```
ccccggcaaa gtggtgatca aggccaactg gaaggctcct gcggaaaact ttgtgggtga   4080
cgcgtaccac gttggttgga cgcacgcatc gtctttgcgc tcaggtcagt cgatatttac   4140
ccctcttgcg ggcaacgcta tgcttccacc cgaaggcgcg ggcttacaaa tgaccagcaa   4200
gtatggcagt ggaatgggcg tattgtggga cggctactcc ggtgtccaca gtgctgacct   4260
ggttcccgaa atgatggcat tcggcggcgc aaaacaggaa aaactcgcca aggaaatcgg   4320
cgatgtccgg gcacggattt accgcagcca tctaaactgc acggttttcc cgaacaacag   4380
cattttgacc tgctccggtg tcttcaaggt ctggaacccg atcgatgaaa cacgaccga   4440 ggtttggacg tatgccatcg tagaaaaaga catgcctgag gacttaaagc gtcgcttggc   4500
tgacgcggtt cagcgcactg tcggaccagc aggattctgg gaaagcgacg acaacgacaa   4560
catggagacg gagtcgcaaa atgccaagaa ataccaatcc agcaacagtg atctgattgc   4620
caatttgggt ttcggcaagg acgtctacgg cgacgaatgc tatccgggcg tcgttgccaa   4680
atcggcaatc ggcgaaacca gctatcgcgg attctaccgt gcctaccagg ctcacatcag   4740
cagctccaat tgggccgagt tcgaaaacac ctcccgaaat tggcacaccg aactccacaa   4800
gacgactgat cgctaatcca ggagccaacc atgatgatca atacccagga agacaagctg   4860
gtctccgcgc acgacgccga agaatttcat cgtttcttcg tcgggcacga cagcgatctg   4920
cagcaagaag tcaccacact cctgacccga gaagcacatc tgttggacat tcaggcctac   4980
aacgcctggc ttgaacactg cgttgccccc gagatcaaat accaagtgat ctcgcgagaa   5040
tttcggtcca cttccgagcg tcgataccaa ctgaatgatg cggtgaacat ctacaacgag   5100
aactatcagc acctgaaagt tcgagttgag catcagatgg acccgcagaa ctgggccaac   5160
agcccgaaga tccgtttcac ccgcttcgtc accaatgtca cagcggccaa ggacaagatc   5220
gtaccggatc tgctgcatgt gcgttccaac ctcattctcc accgcgccag acgcggcaat   5280
caagttgacg tcttctatgc aacgcgggaa gacaaatgga aacgcatcga aggtggtggc   5340
atccaactgg tggaacgtct tgtggactac ccggagcgca ttctccagac ccacaatctg   5400
atgaccttcc tgtgaaccct ggggatgcct gccttgatgg cggtcatcct tgattgtttt   5460
aaacagaaat ttattgccat gaacatacag caagttattg ccattactgg cgccggttca   5520
ggcatcgggc tggaactggt tcgatccttc aaagcagctg gctattgcgt gtccgcactt   5580
gttcgcaacg aggaacaaga ggcgggcctt cgcagtgaat tcaaagatgc cattgagatc   5640
gtagcgggcg atgtttgtga tcacgccacc aatgaaaagc tggtcaacaa ggcggtcgcc   5700
aggttcggac acctcgactg cttcatcgga aatgccggga tatgggatta catgctgggc   5760
gtcgacgagc catgggagaa attatccggc agtttcgagg agatatttga tatcaacgtc   5820
aaaagctatt tcagcggcat cagcgcgcc ttgccggaac tcaaaaaaac gaacggatcg   5880
gtcgtagtga cggcttccgt ttcttcctat gcggccggcg gcggcggctc ttgctacatt   5940
gccagcaagc atgcagtgct gggtatggtc aaggcgttgg cctacgaatt ggccccgcac   6000
atccgggtca atggcgttgc gccaggtggt acggtcactt ctttggctgg gccggcaagc   6060
gccggtttcg acaaaaccaa aatgaaagac atgcccggca tcgatgacat gatcaagggc   6120 ctgacccct tggggttcgc agcaaggccc gaggacgtgg tggcaccgta tcttttgctg   6180
gcctcccggg aacaagggaa gttcatcact ggcaccgtaa tcggcattga tggcggcatg   6240
gcgctcggtc gaaagtgaat tttcaatcaa atcagatttt tcaaccccat tcccaggaga   6300
caacccatga gacgaaatt gttcatcaac aacacctgga gcgcttcgag tgacaaaaag   6360
tcattcgatc gcaagcaccc tgtcagtggc gaggtcgtga cccaatgcgc gaacgccacg   6420
```

```
gtggacgatg cggtcaatgc ggctcgagcc gctcaagagg cgttcaagtc ctggaaggcc   6480
gtcggaccct cggagcggcg gcgccttctt ttgaaggtgg cagacgtcat ggagagcaaa   6540
acgcccgagt tcatcgaagt gatggccaag gaagtgggag cctccgcgct gtgggcgggg   6600
ttcaacgtgc acctgtcggc caatgtattc cgggaagccg cctcactggc cacccaaatt   6660
caaggcgaaa ccattccgac ggacaagcct gacaccctgt caatgacgct gcgtcacgct   6720
gtcggcccca tcttgagcat cgttccctgg aacggcaccg ccgtgctcgc ggcgcgggcc   6780
atcgcttatc cgctggtctg cggcaatacc gttgtgttca aggctccga gttcagcccc   6840
ggtacgcacg ctttgatcac caagtgcctg caggaggccg acctgcctgc tggcgtgctc   6900
aactatctga actcctcccc ggaccggtcg cccgatattg cagatgcgct gatttcgtct   6960
aaagagattc gtcgcatcaa cttcacaggc tccactcgcg tggggcgcat catcgcccag   7020
aaatcggccc agcatctcaa cgctgcttg ctggagttgg gtggaaagtc cccgctgatc   7080
gttctggacg acgctgacat cgacgcggca gtcaaggccg cggtgttcgg cagcttcctg   7140
ttccaaggcc agatctgcat gtccaccgaa cgcctggtgg tcgacgaaaa gatcgcggac   7200
gaatttgtcg cgaagttcgt cgagaaaacc aagcagttga gcgcaggcga tccatgcgtc   7260
acagggact gcatcatcgg cccgatggtg tcgcccaact cgggtgaccg aatcaatggt   7320
ctgttcaaag atgccatcag caagggcgcc aaggtcgtgt gcgcggcat cgccgagggt   7380
gcggtcatgc ccgccacgat cttggaccac gtgacagccg acatgcagat ctacgatgag   7440
gaaaccttcg gtcccatcac tgtggttatc cggtgcaaga gcgaagcgga cgccatccgc   7500
attgccaatg acagcgccta cggcctgtca tcgggcgtgt ttggccggga cgtgaaccgg   7560
gctctgcgcg tgggcatggc gatcgaatac ggctcggtcc atatcaacgg ctccaccgta   7620
cagaacgagg ctcaggcgcc ttatggcgga acaaaggcca ccggttatgg ccgcttcgac   7680
ggacgcgcgg tgatcgacga gttcacggaa ctcaagtggc tgaccattga accattcgag   7740
cagcagtatc ccttctaagc tgaagcaaca aaggagttaa accatgaaca agccagcaac   7800
tgtcattgaa ttggggtaca tgggcatttc ggtcaaggat cccgcagcgt ggaaatcctt   7860
tgccgcaaac atgctgggac ttcaagtcct cgatgagggt gacaaggatc gcttctatct   7920
gcgaatggac aattggcacc atcggatcgt ggttcatcac aacggtcaag atgaccttga   7980
atacctgggc tggcgtgtcg ccggtcaacc ggaattcgag gcattgggtc aaaagctcgt   8040
ggacgcaggc tacaaagtcc gcgtgtgcga caaagccgaa gcacaagaac ggatggtgct   8100
gggcctgatg aagacagaag atccgggggg caacccgacc gagattttct ggggaccccg   8160
gattgacctg aacaacccct ccatcccgg tcgtcccttg cacgggaaat ttctaaccgg   8220
tgatcagggc ctgggccact gcatcgtgcg tcagaacgat gttgaagcgg cacgtaagtt   8280
ctatagcttg ctgggatttc gtggagatgt cgagtaccgc cttcctttgc caacggcat   8340
gacggctgag ttgacgttca tgcattgcaa tgctcgcgat cattccatcg ctttcggtgc   8400
aatgcctgcg gccaagcgcc tcaatcatct gatgattgaa tacactcata tcgaagattt   8460
gggttgcaca caccagcttt tcacgaagga aaagattgac attgccttgc aattgggcat   8520
ccattccaac gataaggcgc tgacgttcta cggggcaaca ccttccggct ggctgataga   8580
acctgggtgg cgaggcgccc ccgccattgc tgaatcggaa tattacgtcg gcgacatttt   8640
cggccacacc atcgaggcca ccggttatgg attggacgtc aaactgagct agccatgtaa   8700
cagatgcgaa atcgatcgca tctgttttcc ccattcagtt ccatataaaa aaaggagac   8760
```

```
aatgatgatc aaagaagcca tttccctcgc aggacttggg atgctgatgc tcagcaccgc    8820
atatgccgag gattcccgtt ggtcatatcg catcggcgcc accaacgtag ccttcgatgc    8880
gagcgccaaa gtttcgattg acggaacaag ggtgccgggt ggaagcgctg acgccagtga    8940
caacaacgct ttgacatttg acttcggtta catcattaac gataactgga acgcgcgatt    9000
aattgttggc attccaccca ccacaaaagt gacgggcgca ggcacgctgc ctccgatttt    9060
gctgggccgt gtccaatatg ctcctgcagt tttgtcggcg acctacaacc tgccacagat    9120
gggattggtt cgcccgtacg tggggcggg gatcaactac actcgaattc tgaaaagcaa     9180
agatgccaat ctgacctcat tcgatgcaga tcatgcgtgg gcacttgtgc tccacatcgg    9240
tgcagaagcg aacatcaacc gcgactggtt cgtcagcttt gatatccgaa aactttatct    9300
aaaaacagat gcatcggggt ttcttgggcc tcaagttgct acagcccgcg taacgttgaa    9360
tccgctgctg acgtcgattg cgattggccg gagattctga tcggtccaca ttgattccaa    9420
aattctgttt gcatcaccat tttcaaagga aatttgaatg acaagaaaga cgagcaaagc    9480
ggtgcgcctg accgccgcgg atattcaagg cgcatgggtc atcatgccga ccccgtccac    9540
gccggatgcc tcggactggc gcagcacgca cacggtcgat ctcgacgaga cggcccggat    9600
tgtcgaggag ttgattgcgg ccggcgtcaa tggcattctg agccacggca cctttggcga    9660
atgcgcgacg ctgacgtggg aggagaagcg ggattttgtt tcaacggtcg tggaaaccgc    9720
gcgcggtcga gtgccctact tctgcggcac aacggccttg aatacccgtg aagtcatacg    9780
ccagacccgc gaattgatcg acattggcgc ccaaggaaca atgctcggcg tgccgatgtg    9840
ggtgaagatg gatctgccta ctgccgtgca attttatcgc gatgtggcgg aagcagtgcc    9900
agatgcagcc atcgctgtct acgccaaccc ggaggctttc aaatttgatt ttcctcgccc    9960
gttttgggcc gaaatgtcca aaatcccgca ggttgtcaca gccaagtact tgggcatcgg   10020
gatgctggac ttggatctga aattggcccc aaatattcgc ttccttccgc atgaggatga   10080
ctactacgct gcggcccgga tcaatcccga gcgcatgact gctttctggt ctagcggttc   10140
catgtgcggc ccagcgaccg cccttgtgct gcgcgatgag gtggtaaagg ccaaaaatac   10200
aggtgattgg gccaaggcca aggctatttc agatgacatg cgcgcagccg atgccacact   10260
gtttccacgc ggcgatttct cggaattctc aaaatacaac attggcctcg aaaaagcacg   10320
aatggacgag gccggctggc tcaaggcggg gccgtgccgg ccaccctata cgctggttcc   10380
cgacgaatac cttgcaggtg cccgaaaatc aggcaaggcc tgggccgcac tgcataccaa   10440
gtatgccaag gaattgagga aaaccaaaac ggcaaccaac tcgaaaaaga agtaagtcca   10500
ggccctgagt cagacatctc cgatcagcac aacctgctga tctggaggtt ttctggatta   10560
gtgcagtcgg cgagttaaaa atatgccagt acagagtgga agcgccacaa gcgcagggtg   10620
caccgatcgc cctgaagcaa tctcacacta ttgccatctt ctctttgttg ggagtgcatg   10680
atcgtgatgg tcgatttta tttcgatttt ttgagcccat tttcgtatct ggccaaccac   10740
cgtttgtcgg tgctcgccgg gcgttatgga ttctccatcc agtatcacgc cattgatttg   10800
gcgcgagcaa aaacgccat tggcaacatc gggccatcca atcgggacct caaggtcaag   10860
cttgactact taaaggtgga tttgcagcga tgggccgatc tctataggat tccgttggtt   10920
ttccccccta acttcaacag ccgccgggtg aatgccggac tgtattaccc ggcagccagg   10980
gagcgagccg ctgaatatgt tcgccttgtt ttcgattcgg cttgggggaa agggtgggca   11040
ctggatgctg atagcttgct ggctgaggta tgcgacaagc taaactggga tctcggtgaa   11100
tttgaagatt ttttgaacag cgaaaatgcc gccaaggcat acgacgaaga gacgcaggcg   11160
```

```
gccattgacc gaaaggtttt cggggttccc accgtgtttt gggatgatca aatgtggtgg    11220
ggaaatgacc gccttttcat gcttgagagc aggttgcaaa aggaaacgca accataaatt    11280
ctcagtgcat cgattttcct gattttcaa ccacgccttg attttaagga gtctcatgaa    11340
gctttattac agccccggcg catgttcatc gtcgcctcac atcatccttc gtgaaggtgg    11400
atttgacttt cagctagaaa aggttgatct cggcaccaag gtgactgaga ctggtgttga    11460
ttacaagacc gtcaatcccg tgggcagtgt ccccgctttg caaatggatg atgggcaggt    11520
gctcaccgaa gggccggcca tcgttcaata cctcgctgac cgtgtgccag aaaaatgcct    11580
ggcaccggca gctggctcgc tggagcgtta ccgactgatg gaatggctga atttcatctc    11640
caccgaattg cataaaagct tcggagcgct gttcagcccg gtgtttccac aggatgccaa    11700
gccagtcatc aaggcccaat ggaaagccg tcttgcccat accgagcaga tgctcggtga    11760
caaggtttgg gccatgggga cgacttttc cgtggtggac gcctacttgt ttactgtgct    11820
tggctggggg gcttacgtga atgtggacct ttcgccttgg cccggcctgc aaggctacct    11880
caaccgcgtg gctgaacgtc cagcagtccg ggccacattg tcggctgaag gtttgatctg    11940
atttttttag agaaataaat aaagcatggc cagcctccat gagcggccag ccatgccgcg    12000
gggcagccgt gggcagcggc ctcgatcaaa tttcgatgca cacagattac gagccccttt    12060
ttccgactgc ggtcggattc agaaattgcc gatacttgct ttggtctgat cgaagcgtga    12120
gggatatcgg cttcccctat ccacatgctt gatgaagagg agcgtatcac catgagtcac    12180
gaacttggcc gactggaaga cctgccgcag gactaccgag acgaactcaa acaacttaac    12240
ctggtgccgc tatggcccag cctacgcgcg gtgctgccgc ccaatgtccc gacccgccag    12300
acgcagccga cttactggtc ctaccagacg ctcaagccgc tgctgctcaa ggccggtgag    12360
ctgaccccca ttgagaaggc cgagcgccgc gtgctggtgc tggccaaccc cggccacggc    12420
ctggagaaga tgcaagccag cgccgccata tacctgggca tgcagttgct gctgcccggc    12480
gagtgggcgc ccagccaccg ccacaccccc aacgcggtgc gcatgatcgt ggagggcgag    12540
ggcgcctaca ccaccgtgga tggcgagaag tgccccatga gccggggtga cctcatcctc    12600
acgcccaccg gcctgtggca cgagcacggc cacgacggca acgagcccgt ggtgtggctc    12660
gatgtgctgg acctgccgct ggtgtactac atggaggcca gctaccacat cgacggcgag    12720
cgccagcagg tcgaccccgg ccggggcgac tgcgcctgga cccgtgcggg cgtggtgcca    12780
acccccgtgt ccagcgcag cgacaagcgc tatcctctct gcgctaccc ttgggccgac    12840
acccgtgccg ccctgctgtc gctggcggcc gaccagcctg agcaggaatg cgtgcaggtc    12900
acctacgtca accccgaaac gggtgacgac gccgagaaca tcctgggctt ctacgccctg    12960
atgctcaagc ccggccagac cctgcgcctg cccgtgcgtt cgcccgccgt ggtgttccac    13020
cagatcgaag gccgcagcga ggcgcgcatc gccgagtcca ccttcgccct gagggaagcc    13080
gatacctgct gcgcccccgg ctacaccgag gtgacgctga aaaacctctc agccgaccag    13140
ccgtccttca tcttcatggc cgacgaatcg cccctgcacc gcaagctggg cgtctttgaa    13200
aaccgcggct gagccgccgc gaagcaccac acaacaggaa agcaagtgag caactacctc    13260
tggaacccgc ctcccgtcca gtctctgccc gttcgtggca agaccgagcg cttccccatc    13320
aaccgcatct tctgcgtcgg ccgcaactac cacgcccacg cggtggaaat gggccgtccg    13380
gtcgacaaaa gcgtcgaaca agcgttctac ttcaccaaat cgccacaaac cctggtggaa    13440
agtggtgcga ccgtggccta cccgccgcgc accagcaact accactacga gatggagctg    13500
```

```
gtgctggcga tcggcaagcc cggcttccgc gtcagcgaag accaggcgca cgagttgatt   13560
tacggctacg ccgccggcct ggacatgacc cggcgcgacc tgcaactggt ggcacgcgac   13620
aagggccgcc cctgggacac cggcaaggac atcgaggaag gctcggtctg ctccgagatc   13680
gtgccgatgc aaggcgtggt ggtggagcag ggcgcgatcg ccctggaagt caacggccag   13740
accaaacagt cgtccaacgt ggacaagctg atctggaacg tccgcgagat cattgccgac   13800
ctctccacct actaccactt gcaacccggc gacctgattt acaccggcac gcccgaaggc   13860
gtgggcgccg tggtggcggg tgacaagatc atcggccgtg tggaaggcat tgccgagatc   13920
agcctgaccg tcggcccggc cgagtgagcc tgcacgcgat gaagctgtac aacttctggc   13980
gcagcggcac gtcacaccgg ctgcgcatcg cgctcaacct caagggcgtg ccctacgagt   14040
acctggccgt gcacctgggc aaggaagagc acctaaagga cgccttcaag cgcctgaacc   14100
cacagcagtt ggtgcccgcg ctggacacgg gcgcgcaagt gctgatccag tcgccggcca   14160
tcatcgaatg gctggaggaa cagtacccca cgcccgcgct gctgccggcc gacgccgacg   14220
gccgccaacg ggtgcgcgcg ctggccgcca tcgtgggctg cgacatccac cccatcaaca   14280
accgccgcat tctggagtac ctgcgcaaga cgttcggcgc cgacgaggcc gccatcaacg   14340
cctggtgtgg cacctggatc agcgccggtt tcgatgccta cgaagcactg ctggcggtcg   14400
acccgaagcg cggccgctac agctttggcg acacacccac gctggccgac tgctacctgg   14460
tgccgcaggt ggaaagcgcc cgccgcttcc agtggacct gacgccctac cccctgatcc   14520
gcgcagtgga cgcggcctgc ggcgagttgg acgcatttcg gcgcgccgcg ccagctgctc   14580
aacctgattc ggcttgacga aaaatacgcc gccttcgccc taataaacag ttcgtagccc   14640
tgcccagtga caagtatcaa tgagcaatag tgaaaatgta aggggaaaga ttatgaaaca   14700
tattctgacc cgacgagcag ccctgagcac tttgggctcc cttggaatcg ggggccttcc   14760
gggcatgagc ttggcgcaat ccggccctgg cgtggccacg atcgtgattg gactcgccgc   14820
aggcggagcg accgatatgg ctgcccgccg gttgtctgag ggaatgcgcg gtgcctatgc   14880
ttccagtgtg ctcgtcgaca accgcacggg ggcgggtggt cgaattgcga tccagcatgt   14940
taaggccgcg gcaccaaacg gcgcgacact tctgctgacg cctgcatcca tgatgacgct   15000
ataccctcac acgtacaaag atct                                          15024
```

<210> SEQ ID NO 12
<211> LENGTH: 4912
<212> TYPE: DNA
<213> ORGANISM: Artificial Sequence
<220> FEATURE:
<223> OTHER INFORMATION: A modified DNA molecule encoding valine at the
      position corresponding to the F352 amino acid in
      NDO.

<400> SEQUENCE: 12

```
gagctcgttg cgcaagcgct tccatcagtg ggggcatgaa gtacatctcg ccgatgtcgg      60
tcattgccaa gttgaaggtg cgcgtgctgg caaatgggtc gaaagagtca cgggtcgtca     120
gtgccgtctg cagcgtgttg agcgcataga ccacgggctc cgcaagatgc agtgcatacg     180
gtgtcggctc catgccttt gaggtgcgca agaacaaatc gtcctttagc gccgcacgca     240
gccgtttaag tgaattgctg acggcaggct gcgtcagccc cagttttcg ccggccgtcg     300 atacgctccg gtcgagcagt agctggttga agaccaccag cagattcaag tcgatgtcgc     360
gcagatccat gatgcctcac cattattcat gctggtgatt ttaactatca gacttgatct     420
atagcgctat accgatcgac gcgccagtat cgcagccatt cggagacaac tgaaaaaaga     480
```

```
gcttgcatgg aactggtagt agaacccctc aatttgcatc tgaacgcgga gaccggcagc    540
accctgcttg acgtgctcag gtccaacgag gtccccattt cttatagctg catgtcgggc    600
cgctgcggca cttgccgttg ccgtgtgatt gccggccatc ttcgcgataa cggctccgag    660
acagggcgcc cgcaggcagg aaaggggggcc tatgtcctgg cctgtcaggc ggttctgacc   720
gaagactgca cgatcgagat tcctgaatct gacgagatcg tggttcaccc ggcgcgcatc    780
gtcaagggga cggtcacagc gatagacgaa gccacccatg acatccggcg cctgcgcatc    840
aaactggcca aaccgcttga gttcagccct ggccagtacg caacggtgca gttcacgccc    900
gaatgcgtcc gccctattc gatggccggg ctgcctagcg atgcggaaat ggagtttcag     960
attcgcgcgg ttccgggcgg gcatgtcagc aactacgttt tcaatgaact gtccgtaggc   1020
gcttcggtgc ggatcagcgg ccccctcgga acggcctatc tgcggcgcac gcacaccggc   1080
cccatgcttt gtgtgggggg tggaacaggt ctggcgcccg tcctttcgat cgttcgaggc   1140
gcactggaaa gcgggatgag caaccccatc catctgtact tcggtgtgcg gagcgagcag   1200
gacatctatg acgaggaacg ccttcacgca ttggctgcaa ggtttccgaa tctcaaggtg   1260
aatgtcgttg ttgcaacagg ccctgccggc cctggtcatc gatccggcct ggtcaccgat   1320
ctgatcggcc gtgacttgcc caatttggcg ggatggcgcg cctacctgtg tggcgctccg   1380
gccatggtcg aggccctgaa cctgctcgtt gctcgcctag gcatagtacc cgggcacatc   1440
catgccgatg cgttctatcc cagcggcgtc tgagcgaagg caccatgcga acccaattca   1500
acccaaggat accaagccat gagtgaaccc caacgattaa acccgtgtt tccccaagat    1560
ccgaaatggc cgggcgaagg tagcagccgc gttcccttct gggcctacac ccgcgaagac   1620
ctgtacaagc gcgaattgga gcgcctgttc tatgcaaacc actggtgcta tgtaggcctg   1680
gaagccgaga ttccgaatcc aggcgacttc aagcgaacgg tgatcggtga gcgctcggtc   1740
atcatggtgc gtgatccgga tggcggcatc aacgtggtgg agaacgtctg cgcccactgt   1800
ggcatgcgct tttgccgcga gcgccacggc aacgccaagg acttcttctg cccctaccac   1860
cagtggaact acagcctcaa gggtgacctg cagggcgtgc ccttccgccg aggcgtcaag   1920
caggacggca aggtcaacgg cggcatgccc aaggacttca aactcgaaga acacggcctg   1980
accaagctca agtggccgc cgaggcggt gcagtgtttg cctctttcga ccacgatgtc    2040
gagcctttcg aggactgtgc gtgtacgaca gcgagatgat ccccaactcc ctcatctacc   2100
ccatttgagg ttgcagaaca tgtccgagaa ctggattgat gccatcgcac gggacgctgt   2160
gcctgagggc gatgtggtcg gagtcatcgt ggcaggcaaa gacattgcct tctatgaggt   2220
ggaaggtgag gtcttcgcca ccgacaactt gtgtacccac ggggctgcgc gcttgagcga   2280
cggctttctc gaaggccggg aaattgaatg tcctttgcat caaggccgat tcgatgtttg   2340
cacgggtaaa gccttgtgca cacccctgac acaggacatc aaaacctacc ccgtaaaaat   2400
cgaaaacatg cgcgtgatgc tcaagctgga ctaaaactct ttgcaggagg aaagccaaat   2460
ccggaaatca ccccacccaa cccaatcact acccgttttc aaacaagagg agataagcaa   2520
ttatgagtta ccaaaactta gtgagtgaag cagggctgac gcaaaagctc ctgattcatg   2580
gcgacaaaga acttttccag cacgaattga agaccatctt cgcgcggaac tggcttttttc  2640
tgacccatga cagtctgatt ccctcccccg gcgactatgt cacagccaaa atgggcgtcg   2700
atgaagtcat cgtctcccgc cagaacgatg gctcggtgcg agccttttttg aatgtttgcc   2760
gtcaccgggg caagacacta gttcacactg aagccggaaa tgcgaaaggc tttgtgtgcg   2820
```

-continued

```
gctaccacgg ctggggctac ggttccaacg gcgaactgca aagcgttccc tttgaaaaag    2880
agttgtacgg agatgcgatc aaaaagaaat gcctgggctt gaaagaagtc ccccgcatcg    2940
aaagctttca tggctttatc tatggctgtt ttgatgcaga agctcccccg ctcatcgatt    3000
atctgggtga tgcagcctgg tacctggaac ccaccttcaa gcactctggt ggcctggaac    3060
ttgtaggccc ccccggcaaa gtggtggtta aggccaactg gaagcctttt gcggaaaact    3120
ttgtaggtga catctaccac gttggttgga cgcacgcagc ggctttgcgc gcagggcagt    3180
cggtatttag ttctcttgcg ggcaacgcta agcttccacc cgaaggcgcg ggcttgcaaa    3240
tgaccagcaa gtatggcagt ggaatgggct aacgtggga ctactactcc ggtaacttca    3300
gcgctgatat ggttcccgat ctgatggcat tcggcgccgc aaaacaggaa aaactcgcca    3360
aggaaatcgg cgatgtccgg gcacggattt accgcagcat tctgaacggc acggttttcc    3420
cgaacaacag cttttgacc ggctccgcta ccttcaaggt ctggaacccg atcgatgaaa    3480
acacgaccga ggtttggacg tatgccttcg tagaaaaaga catgcctgag gacttaaagc    3540
gtcgcttggc tgacgcggct cagcgcagtg tcggaccagc aggattctgg gaaagcgacg    3600
acaacgaaaa catggagacg ttgtcgcaaa atgccaagaa ataccaatcc agcaacagtg    3660
atcagattgc cagtttgggt ttcggcaagg acgtctacgg cgacgaatgc tatccgggcg    3720
tcgttggcaa atcggcaatc ggcgaaacca gctatcgcgg attctaccgt gcctaccagg    3780
ctcacatcag cagctccaat tgggccgagt tcgaaaatgc ctcccgaaat tggcacaccg    3840
aactcaccaa gacaactgat cgctaatcca ggagccaacc atgatgatca atacccagga    3900
agacaagctg gtctccgcgc acgacgccga agaatttcac cgtttcttca tcgtacaaga    3960
tgatgcacta ctgcaagaag tcaacacgct cctgacccgc gaagcgcacc tgctggacat    4020
tcaggcctac aaagcctggc ttgaacactg cgttgccccc gagatcaaat accaagtgat    4080
ctcgcgagaa cttcgctcca cttccgagcg tcgataccaa ctgaatgatg cggtgaatct    4140
ctacaacgag aactatcaac agctgaaagt tcgagttgaa caccagatgg atcctcagaa    4200
ctgggccaac aacccgaaga tccgcttcac ccgcttcgtc accaatgtca cggcggccaa    4260
ggacaagagc gcaccggaaa tgctgcatgt gcggtccaac ctcattctcc atcgcgccag    4320
acgagaaaac caagttgacg tcttctatgc aacgcgtgaa gacaaatgga aacgcatcga    4380
aggtggtggt atcaaattgg tcgaacgctt tgtggactac ccggagcgca ttccccagac    4440
ccacaacctg ttggtcttcc tgtgaaccct ggggatgcct gcctggatgg cgggcattcg    4500
tgattatttt taacagaaat ttattgccat gaacacacag caagttgttg ccatcactgg    4560
cgccggctcg ggcattggtt tcgagttggt tcgctctttt aaggcagccg gttatcgcgt    4620
atctgcactc gttcgcaacg aggagcaaga ggcgggtctt cgcagtgaat tcaaagacga    4680
cattgagatc gtggcgggcg atgtccgtga tcacgccacc aatgagaagc tggttaaaca    4740
gacggttgcc aagttcgggc gcctggattg cttcatcgga aatgccggga tatgggatta    4800
catgctgagc atcgatgatg cttgggagaa attctcgggc agtttcgacg agatatttga    4860
catcaacgtc aaaagctatt tcagcggcat cagcgcggcc ttgccggagc tc            4912
```

<210> SEQ ID NO 13
<211> LENGTH: 6779
<212> TYPE: DNA
<213> ORGANISM: Artificial Sequence
<220> FEATURE:
<223> OTHER INFORMATION: A modified DNA molecule encoding valine at the
    position corresponding to the F352 amino acid in
    NDO.

<400> SEQUENCE: 13

```
atgcatacgt agcggtggcg aaagaggcgc cgctggaaga atccggtctg tagctctggc      60
agaagaccca aggcgagatc aaccgcaccg gactccatat cctccttcag attgccagca     120
ttcgggcgca gcgtgctgat ctggatgtga ggagctcgtt gcgcaagcgc ttccatcagt     180
gggggcatga agtacatctc gccgatgtcg gtcattgcca agttgaaggt gcgcgtgctg     240
gcaaatgggt cgaaagagtc acgggtcgtc agtgccgtct gcagcgtgtt gagcgcatag     300
atcacgggct ccgcaagatg cagtgcatac ggtgtcggct ccatgccttt tgaggtgcgc     360
aagaacaaat cgtcgttcag cgctgtacgc agccgtttaa gtgaattact gacggcaggc     420
tgcgtcagcc ccagtttttc gccggccgtc gatacgctcc ggtcgagcag tagctggttg     480
aagaccacca gcagattcaa gtcgatgtcg cgcagatcca tgacctcacc ctcaccatta     540
ttcatgctgg tgattttaac tatcagactt gatctatagc gctataccga tcgacgcgct     600
agaatcgcag ccattcggag acaactgaaa aagagcttg catggaactg gtagtagaac      660
ccctcaattt gcatctgaac gcggagaccg gcagcaccct gcttgacgtg ctcaggtcca     720
acgaggtccc catttcttat agctgcatgt cgggccgctg cggcacttgc cgttgccgtg     780
tgattgccgg ccatcttcgc gataacggcc ccgagacagg gcgcccgcag gcaggaaagg     840
gggcctatgt cctggcctgt caggcggttc tgaccgaaga ctgcacgatc gagattcctg     900
aatctgacga gatcgtggtt cacccggcgc gcatcgtcaa ggggacggtc acagcgatag     960
acgaagccac ccatgacatc cggcgcctgc gcatcaaact ggccaaaccg cttgagttca    1020
gccctggcca gtacgcaacg gtgcagttca cgcccgaatg cgtccgcccc tattcgatgg    1080
ccgggctgcc tagcgatgcg gaaatggagt ttcagattcg cgcggttccg ggcgggcatg    1140
tcagcaacta cgttttcaat gaactgtccg taggcgcttc ggtgcggatc agcggccccc    1200
tcggaacggc ctatctgcgg cgcacgcaca ccggcccat gctttgtgtg ggggtggaa     1260
caggtctggc gcccgtcctt tcgatcgttc gaggcgcact ggaaagcggg atgagctacc    1320
ccatccatct gtacttcggt gtgcggagcg agcaggacta ctatgacgag gaacgccttc    1380
acgcattggc tgcaaggttt ccgaatctca aggtgaatgt cgttgttgca acaggccctg    1440
ccggccctgg tcatcgatcc ggcctggtca ccgatctgat cggccgtgac ttgcccaatt    1500
tggcgggatg gcgactgcat cctgtgtggc gctccggcca tggtcgaggc cctgaacctg    1560
ctcgttgctc gcctaggcat agtacccggg cacatccatg ccgatgcgtt ctatcccagc    1620
ggcgtctgag cgaaggcacc atgcgaaccc aattcaaccc aaggatacca agccatgagt    1680
gaacccccaac gattaaaacc cgtgtttccc caagatccga aatggccggg cgaaggtagc    1740
agccgcgttc ccttctgggc ctacacccgc gaagacctgt acaagcgcga attggagcgc    1800
ctgttctatg caaccactg gtgctatgta ggcctggaag ccgagattcc gaatccaggc    1860
gacttcaagc gaacggtgat cggtgagcgc tcggtcatca tggtgcgtga tccggatggc    1920
ggcatcaacg tggtggagaa cgtctgcgcc caccgtggca tgcgcttttg ccgcgagcgc    1980
cacggcaacg ccaaggactt cttctgcccc taccaccagt ggaactacag cctcaagggt    2040
gacctgcagg gcgtgccctt ccgccgtggc gtcaagcagg acggcaaggt caacggcggc    2100
atgcccaagg acttcaaact cgaagaacac ggcctgacca agctcaaggt ggccgccccg    2160
aggcggtgca gtgtttgcct cttccgacca cgatgtcgag cctttcgagg acttcctggg    2220
ccaaccatcc tgcactactt cgatcgcgtc ttcaatggcc gcaagctcaa gatcctgggc    2280
```

-continued

```
taccgccgcc agcgcatccc gggcaactgg aagctgatgc aggagaacat caaggacccc    2340
taccacccgg gcctgctgca cacctggttc tcgaccttcg ggctctggcg cgccgacaac    2400
aagtcggaac tgaagatgga cgccaagttc cgccacgccg caatgatctc cacgcgcggt    2460
cagggcggca agaacgagga ggtcgtgtcc ggcgtggaca gcttcaagga acagatgaag    2520
gtgaacgacc cgcgcctgct cgacatcgtg cccgagccct ggtggggcgg tccgactgcg    2580
gtgatgacca cgatcttccc cagcgtgatc atccagcagc aggtcaacag cgtatcgacc    2640
cgccacatcc agcccaacgg tcacggctcc ttcgatttcg tctggaccca cttcggcttc    2700
gaggacgaca acgaggagtg gacccagcgc cgcctgatcc aggccaacct gttcgggccg    2760
gcgggcttcg tgtcggccga tgacggcgag gtgatcgagt ggtcgcagga aggctttgag    2820
caaaaaccga cgcaccgcac cgtgatcgag atgggcggtc acgaaatcgg cgacacggac    2880
cacatggtca ccgagacgct gatccgcggc atgtacgact actggcgcaa ggtgatgggg    2940
gaataaacat ggtagacttc aaaacctatt tcgaactgct gaacctgtac agcgactacg    3000
ccatggtgtg cgactccgcc aattgggaga gtggcctga tttcttcatc gagaccggca    3060
cctaccgcct gcaaccgcgc gaaaacttcg agcaggactt gccgctgtgt ctgctggcgc    3120
tggagagcaa ggccatgatt cgtgaccgag tgtacggtgt caaggaaacc atgtaccacg    3180
atccctacta ccagcgccac atcgtaggca cgccgcgcgt gctgtcagtg gagcgtgatg    3240
cggacggcga gcgcatcacc gccgaagcca gctatgccgt gattcgcacc aagtacgacg    3300
gcgattccac gattttcaac gccggctatt accgagacgt gatcgtgcgc acgcccgagg    3360
gcctcaagct gaagtcgcgc ctgtgcgtgt acgacagcga aatgattccc aactccatca    3420
tctaccctat ctgagaagga atccaatgag cgagaactgg atcgacgccg ccgcccgcga    3480
cgaggtgcca cgagggcgac gtgatcggca tcaatatcgt cggcaaggag attgcctcta    3540
cgaggtggcg ggcgagatct acgccaccga caacacctgc actcacgcg ccgcccgcat    3600 gagcgatggc tttctcgaag gccgggaaat tgaatgtcct ttgcatcaag gccgattcga    3660
tgtttgcacg ggtaaagcct tgtgcacacc cctgacacag gacatcaaaa cctaccccgt    3720
aaaaatcgaa aacatgcgcg tgatgctcaa gctggactaa atgctcaagc tggactaaaa    3780
ctctttgcag gaggaaagcc aaatccggaa atcaccccac ccaacccaat cactacccgt    3840
tttcaaacaa gatgagacaa gcaattatga gttaccaaaa cttagtgagt gaagcagggc    3900
tgacgcaaaa gcacctgatt tatggcgaca agaactttt ccagcacgaa ttgaagacca    3960
tcttcgcgcg gaactggctt tttctgaccc atgacagtct gattccctcc ccggcgact    4020 atgtcaaagc caaaatgggc gtcgatgaag tcatcgtctc ccgccagaac gatggctcgg    4080
tgcgagcctt tttgaatgtt tgccgtcacc ggggcaagac aatagttgac gctgaagccg    4140
gaaatgcgaa aggctttgtg tgcggttacc acggctgggg ctatggctcc aacggcgaac    4200
tgcaaagcgt tcccttgaa aaagagttgt acggagatgc gatcaaaaag aaatgcctgg    4260
gcttgaaaga agtccccgc atcgaaagct tcatggctt tatctatggc tgttttgatg    4320
cagaagctcc cccgctcatc gattatctgg gtgatgtagc ctggtacctg aacccacct    4380 tcaagcactc tggtggcctg aacttgtag gccccccgc caaagtggtg gttaagggca    4440
actggaaggt ttttgcggaa aactttgtag gtgcatcta ccacattggt tggacgcacg    4500
catctatttt gcgcgcaggg caggcgatat ttgctcctct tgcgggcaac gctatgcttc    4560
cacccgaagg cacgggcttg caagcgacca ccaagtatgg cagtggaatt ggcgtatcgt    4620
tggacgccta ctccggtgtc cagagcgctg atctggttcc cgaaatgatg gcattcggcg    4680
```

-continued

```
gcgcaaaaca ggaaaagctc gccaaagaaa tcggcgatgt ccgggcgcgg atttaccgca    4740
gccaagtgaa cggcacggtt ttcccgaaca actgcttttt gaccggcgcc ggtgtcttca    4800
aggtctttaa cccgatcgat gaaaacacga ccgaggcttg gacgtatgcc atcgtagaaa    4860
aagacatgcc tgaggactta aagcgtcgct tggctgacgc ggctcagcgc tctgtcggac    4920
cagcaggata ctgggaaagc gacgacaacg acaacatggt gttgtcgcaa aatgccaaga    4980
aataccaatc cagcaacagt gatctgattg ccgatttggg tttcggcaag gacgtctacg    5040
gcgacgaatg ctatccgggc gtcgttagca aatcggcatt cagcgaaacc aaccatcgcg    5100
gattctaccg tgcctaccag gctcacatca gcagctccaa ttgggccgag ttcgaaaaca    5160
cctcccgaaa ttggcacacc gaactcacca agacgactga tcgctaatcc aggagccaat    5220
catgatgatc aatacccagg aagacaagct ggtctccgcg cacgacgccg aagaatttca    5280
ccgtttcttc gtcgggcacg acagcgatct gcagcaagaa gtcaccacac tcctgacccg    5340
cgaagccgac ctgctggaca ttcaggccta caaagcctgg cttgaacact gcgttgcccc    5400
cgagatcaaa taccaagtga tctcgcgaga acttcgctcc acttccgagc gtcgatacca    5460
actgaatgat gcggtgaata tctacaacga gaactatcaa cagctgaaag ttcgagttga    5520
acaccagatg gatcctcaga actggtacaa cagcccgaag atccgcttca cccgcttcgt    5580
caccaatgtc acggcggcca aggacaagag cgcaccggaa atgctgcatg tgcggtccaa    5640
cctcattctc catcgcgcca gacgaggaaa ccaagttgac gtcttctatg caacgcgaga    5700
agacaaatgg aaacgcatcg aaggtggtgg catcaaattg gtcgaacgct tgtggacta    5760 cccggagcgc agtccccaaa cccacaacct gatgatcttc ctgtgagccc tggggatgcc    5820
tgcctggatg gcgggcattc gtgattattt ttaacagggc ggattcaaaa gtgaagtgca    5880
acaccctgga tttcagtgaa tgagagtgga gtgctgcggg ctattcacaa gcagttcgcg    5940
gtagaccgcc agcggtgatc gtactcccag ccctttcctt ggccggttgt tgatttcatc    6000
ggcaatcgca tcgagctgct cctggctgta gatgctcaga tccgtcccct tgggcaggta    6060
ctggcgcacc aggccattca tgttctcgtt ggagcctctt tgccaagggc tgtgcgggtc    6120
gcagaagtac acggctatgc cggtttgctc actgagcttc ttgtgcatgg acatctcccg    6180
gccctggtcg tacgtcatgc tcaaccgcat cggctgcgca atgcccagca gcttgtccgt    6240
gaaggcctgc aagacgttgg cagcactggc cggcttgaac tcaggcagct tgaccagcat    6300
caccagccgg ctggtgcgtt ccaccaaggt cccgactgcg ctggcattgc cttctccctt    6360
gatgagatca ccttcccagt gcccgggaaa ctggcggtct tcgatctcgg gcgggcgtac    6420
atggatgctc agcatgtcgg gaatctggcc tctgcggtcc ttgcccttgc tgcgcggcag    6480
ccgcttgttg tgggcgtgac gcagggtggc gatcagctct ttgcgcagct ctcccacggg    6540
catggcatag atgcagttgt agatggtttc gtgtgacacg cggtattcat ggcccagggg    6600
atacaaacgt gccagtgtca ggcaatctg ctcgggcgac cagcgcagcc gcagcagatg    6660
gatcaccagg caggacaaga tcgactcggg atgcagcttg atagctggtc tgccacagcg    6720
tctgcgctgc agggactggc actgggcatg tgcgctgcca tagccagatg aagatgcat     6779
```

<210> SEQ ID NO 14
<211> LENGTH: 449
<212> TYPE: PRT
<213> ORGANISM: Artificial Sequence
<220> FEATURE:
<223> OTHER INFORMATION: A polypeptide encoded by SEQ ID NO:3.

-continued

<400> SEQUENCE: 14

```
Met Asn Tyr Asn Asn Lys Ile Leu Val Ser Glu Ser Gly Leu Ser Gln
 1               5                  10                  15

Lys His Leu Ile His Gly Asp Glu Glu Leu Phe Gln His Glu Leu Lys
             20                  25                  30

Thr Ile Phe Ala Arg Asn Trp Leu Phe Leu Thr His Asp Ser Leu Ile
         35                  40                  45

Pro Ala Pro Gly Asp Tyr Val Thr Ala Lys Met Gly Ile Asp Glu Val
     50                  55                  60

Ile Val Ser Arg Gln Asn Asp Gly Ser Ile Arg Ala Phe Leu Asn Val
 65                  70                  75                  80

Cys Arg His Arg Gly Lys Thr Leu Val Ser Val Glu Ala Gly Asn Ala
                 85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
    290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Val
            340                 345                 350

Gly Pro Ala Gly Phe Trp Glu Ser Asp Asn Asp Asn Met Glu Thr
        355                 360                 365

Ala Ser Gln Asn Gly Lys Lys Tyr Gln Ser Arg Asp Ser Asp Leu Leu
    370                 375                 380

Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415
```

```
Tyr Arg Ala Tyr Gln Ala His Val Ser Ser Ser Asn Trp Ala Glu Phe
            420                 425                 430

Glu His Ala Ser Ser Thr Trp His Thr Glu Leu Thr Lys Thr Thr Asp
        435                 440                 445

Arg

<210> SEQ ID NO 15
<211> LENGTH: 449
<212> TYPE: PRT
<213> ORGANISM: Artificial Sequence
<220> FEATURE:
<223> OTHER INFORMATION: A polypeptide encoded by SEQ ID NO:4.

<400> SEQUENCE: 15

Met Asn Tyr Asn Asn Lys Ile Leu Val Ser Glu Ser Gly Leu Ser Gln
 1               5                  10                  15

Lys His Leu Ile His Gly Asp Glu Glu Leu Phe Gln His Glu Leu Lys
            20                  25                  30

Thr Ile Phe Ala Arg Asn Trp Leu Phe Leu Thr His Asp Ser Leu Ile
        35                  40                  45

Pro Ala Pro Gly Asp Tyr Val Thr Ala Lys Met Gly Ile Asp Glu Val
    50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
                85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
    290                 295                 300

Ser Met Leu Thr Cys Ser Gly Val Phe Lys Val Trp Asn Pro Ile Asp
305                 310                 315                 320
```

-continued

```
Ala Asn Thr Thr Glu Val Trp Thr Tyr Ala Ile Val Glu Lys Asp Met
            325                 330                 335

Pro Glu Asp Leu Lys Arg Arg Leu Ala Asp Ser Val Gln Arg Thr Val
            340                 345                 350

Gly Pro Ala Gly Phe Trp Glu Ser Asp Asn Asp Asn Met Glu Thr
            355                 360                 365

Ala Ser Gln Asn Gly Lys Lys Tyr Gln Ser Arg Asp Ser Asp Leu Leu
            370                 375                 380

Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
            405                 410                 415

Tyr Arg Ala Tyr Gln Ala His Val Ser Ser Ser Asn Trp Ala Glu Phe
            420                 425                 430

Glu His Ala Ser Ser Thr Trp His Thr Glu Leu Thr Lys Thr Thr Asp
            435                 440                 445

Arg

<210> SEQ ID NO 16
<211> LENGTH: 449
<212> TYPE: PRT
<213> ORGANISM: Artificial Sequence
<220> FEATURE:
<223> OTHER INFORMATION: A polypeptide encoded by SEQ ID NO:5.

<400> SEQUENCE: 16

Met Asn Tyr Asn Asn Lys Ile Leu Val Ser Glu Ser Gly Leu Ser Gln
1               5                   10                  15

Lys His Leu Ile His Gly Asp Glu Glu Leu Phe Gln His Glu Leu Lys
            20                  25                  30

Thr Ile Phe Ala Arg Asn Trp Leu Phe Leu Thr His Asp Ser Leu Ile
            35                  40                  45

Pro Ala Pro Gly Asp Tyr Val Thr Ala Lys Met Gly Ile Asp Glu Val
    50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
            85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
            115                 120                 125

Asn Lys Lys Cys Leu Gly Leu Lys Glu Val Ala Arg Val Glu Ser Phe
    130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
            165                 170                 175

Ser Gly Gly Leu Glu Leu Val Gly Pro Gly Lys Val Val Ile Lys
            180                 185                 190

Ala Asn Trp Lys Ala Pro Ala Glu Asn Phe Val Gly Asp Ala Tyr His
            195                 200                 205

Val Gly Trp Thr His Ala Ser Ser Leu Arg Ser Gly Glu Ser Ile Phe
    210                 215                 220

Cys Ser Leu Ala Gly Asn Ala Ala Leu Pro Pro Glu Gly Ala Gly Leu
```

-continued

```
                225                 230                 235                 240
Gln Met Thr Ser Lys Tyr Gly Ser Gly Met Gly Val Leu Trp Asp Gly
                    245                 250                 255
Tyr Ser Gly Val His Ser Ala Asp Leu Val Pro Glu Leu Met Ala Phe
                260                 265                 270
Gly Gly Ala Lys Gln Glu Arg Leu Asn Lys Glu Ile Gly Asp Val Arg
                275                 280                 285
Ala Arg Ile Tyr Arg Ser His Leu Asn Cys Thr Val Phe Pro Asn Asn
            290                 295                 300
Ser Met Leu Thr Cys Ser Gly Val Phe Lys Val Trp Asn Pro Ile Asp
305                 310                 315                 320
Ala Asn Thr Thr Glu Val Trp Thr Tyr Ala Ile Val Glu Lys Asp Met
                    325                 330                 335
Pro Glu Asp Leu Lys Arg Arg Leu Ala Asp Ser Val Gln Arg Thr Val
                340                 345                 350
Gly Pro Ala Gly Phe Trp Glu Ser Asp Asp Asn Asp Asn Met Glu Thr
                355                 360                 365
Ala Ser Gln Asn Gly Lys Lys Tyr Gln Ser Arg Asp Ser Asp Leu Leu
            370                 375                 380
Ser Asn Leu Gly Phe Gly Glu Asp Val Tyr Gly Asp Ala Val Tyr Pro
385                 390                 395                 400
Gly Val Val Gly Lys Ser Ala Ile Gly Glu Thr Ser Tyr Arg Gly Phe
                    405                 410                 415
Tyr Arg Ala Tyr Gln Ala His Val Ser Ser Ser Asn Trp Ala Glu Phe
                420                 425                 430
Glu His Ala Ser Ser Thr Trp His Thr Glu Leu Thr Lys Thr Thr Asp
                435                 440                 445
Arg
```

<210> SEQ ID NO 17
<211> LENGTH: 449
<212> TYPE: PRT
<213> ORGANISM: Artificial Sequence
<220> FEATURE:
<223> OTHER INFORMATION: A polypeptide encoded by SEQ ID NO:6.

<400> SEQUENCE: 17

```
Met Asn Tyr Asn Lys Ile Leu Val Ser Glu Phe Gly Leu Ser Gln
  1               5                  10                  15
Lys His Leu Ile His Gly Asp Glu Glu Leu Phe Gln His Glu Leu Lys
                20                  25                  30
Thr Ile Phe Ala Arg Asn Trp Leu Phe Leu Thr His Asp Ser Leu Ile
            35                  40                  45
Pro Ala Pro Gly Asp Tyr Val Thr Ala Lys Met Gly Ile Asp Glu Val
        50                  55                  60
Ile Val Ser Arg Gln Asn Asp Gly Ser Ile Arg Ala Phe Leu Asn Val
65                  70                  75                  80
Cys Arg His Arg Gly Lys Thr Leu Val Ser Val Glu Ala Gly Asn Ala
                85                  90                  95
Lys Gly Phe Val Cys Ser Tyr His Gly Trp Gly Phe Gly Ser Asn Gly
                100                 105                 110
Glu Leu Gln Ser Val Pro Phe Glu Lys Asp Leu Tyr Gly Glu Ser Leu
            115                 120                 125
Asn Lys Lys Cys Leu Gly Leu Lys Glu Val Ala Arg Val Glu Ser Phe
        130                 135                 140
```

```
His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
            165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
            195                 200                 205

Val Gly Trp Thr His Ala Ser Ser Leu Arg Ser Gly Glu Ser Ile Phe
210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
            245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
            275                 280                 285

Ala Arg Ile Tyr Arg Ser His Leu Asn Cys Thr Val Phe Pro Asn Asn
            290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Val
            340                 345                 350

Gly Pro Ala Gly Phe Trp Glu Ser Asp Asn Asp Asn Met Glu Thr
            355                 360                 365

Ala Ser Gln Asn Gly Lys Lys Tyr Gln Ser Arg Asp Ser Asp Leu Leu
            370                 375                 380

Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Arg Ala His Val Ser Ser Ser Asn Trp Ala Glu Phe
            420                 425                 430

Glu His Ala Ser Ser Thr Trp His Thr Glu Leu Thr Lys Thr Thr Asp
            435                 440                 445

Arg
```

<210> SEQ ID NO 18
<211> LENGTH: 449
<212> TYPE: PRT
<213> ORGANISM: Artificial Sequence
<220> FEATURE:
<223> OTHER INFORMATION: A polypeptide encoded by SEQ ID NO:7.

<400> SEQUENCE: 18

```
Met Asn Tyr Lys Asn Lys Ile Leu Val Ser Glu Ser Gly Leu Thr Gln
1               5                   10                  15

Lys His Leu Ile His Gly Asp Glu Glu Leu Phe Gln His Glu Leu Arg
            20                  25                  30

Thr Ile Phe Ala Arg Asn Trp Leu Phe Leu Thr His Asp Ser Leu Ile
            35                  40                  45
```

```
Pro Ser Pro Gly Asp Tyr Val Thr Ala Lys Met Gly Ile Asp Glu Val
50                  55                  60

Ile Val Ser Arg Gln Ser Asp Gly Ser Ile Arg Ala Phe Leu Asn Val
65                      70                  75                  80

Cys Arg His Arg Gly Lys Thr Leu Val Asn Ala Glu Ala Gly Asn Ala
                    85                  90                  95

Lys Gly Phe Val Cys Ser Tyr His Gly Trp Gly Phe Gly Ser Asn Gly
                100                 105                 110

Glu Leu Gln Ser Val Pro Phe Glu Lys Glu Leu Tyr Gly Glu Ser Leu
            115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Ile Phe Lys His
                165                 170                 175

Ser Gly Gly Leu Glu Leu Val Gly Pro Pro Gly Lys Val Val Ile Lys
                180                 185                 190

Ala Asn Trp Lys Ala Pro Ala Glu Asn Phe Val Gly Asp Ala Tyr His
                195                 200                 205

Val Gly Trp Thr His Ala Ser Ser Leu Arg Ser Gly Glu Ser Ile Phe
210                 215                 220

Ala Ser Leu Ala Gly Asn Ala Val Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
                260                 265                 270

Gly Gly Ser Lys Gln Glu Arg Leu Asn Lys Glu Ile Gly Asp Val Arg
                275                 280                 285

Ala Arg Ile Tyr Arg Ser His Leu Asn Cys Thr Val Phe Pro Asn Asn
290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Val
                340                 345                 350

Gly Pro Ala Gly Phe Trp Glu Ser Asp Asp Asn Asp Asn Met Glu Thr
                355                 360                 365

Ala Ser Gln Asn Gly Lys Lys Tyr Gln Ser Arg Asp Ser Asp Leu Leu
370                 375                 380

Ser Asn Leu Gly Phe Gly Lys Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Gln Ala His Val Ser Ser Asn Trp Ala Glu Phe
                420                 425                 430

Glu Asp Ala Ser Ser Thr Trp His Thr Glu Leu Thr Lys Thr Thr Asp
                435                 440                 445

Arg

<210> SEQ ID NO 19
```

-continued

```
<211> LENGTH: 449
<212> TYPE: PRT
<213> ORGANISM: Artificial Sequence
<220> FEATURE:
<223> OTHER INFORMATION: A polypeptide encoded by SEQ ID NO:8.
<221> NAME/KEY: SITE
<222> LOCATION: (35)...(35)
<223> OTHER INFORMATION: Xaa = any amino acid.

<400> SEQUENCE: 19

Met Asn Tyr Lys Asn Lys Ile Leu Val Ser Glu Ser Gly Leu Thr Gln
 1               5                  10                  15

Lys His Leu Ile His Gly Asp Glu Glu Leu Phe Gln His Glu Leu Arg
             20                  25                  30

Thr Ile Xaa Ala Arg Asn Trp Leu Phe Leu Thr His Asp Ser Leu Ile
         35                  40                  45

Pro Ser Pro Gly Asp Tyr Val Thr Ala Lys Met Gly Ile Asp Glu Val
     50                  55                  60

Ile Val Ser Arg Gln Ser Asp Gly Ser Ile Arg Ala Phe Leu Asn Val
65                  70                  75                  80

Cys Arg His Arg Gly Lys Thr Leu Val Asn Ala Glu Ala Gly Asn Ala
                 85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Glu Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Ser Leu Met
145                 150                 155                 160

Asp Tyr Leu Gly Asp Ala Ala Trp Tyr Leu Glu Pro Ile Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Thr Gly Glu Ser Ile Phe
    210                 215                 220

Ser Ser Leu Ala Gly Asn Ala Val Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Pro
        275                 280                 285

Ala Arg Ile Tyr Arg Ser His Leu Asn Cys Thr Val Phe Pro Asn Asn
    290                 295                 300

Ser Val Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ala Val Gln Arg Thr Val
            340                 345                 350

Gly Pro Ala Gly Phe Trp Glu Ser Asp Asp Asn Asp Met Glu Thr
        355                 360                 365
```

```
Ala Ser Gln Asn Gly Lys Lys Tyr Gln Ser Arg Asp Ser Asp Leu Ile
        370                 375                 380

Ser Asn Leu Gly Phe Gly Lys Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Gln Ala His Val Ser Ser Asn Trp Ala Glu Phe
                420                 425                 430

Glu Asp Ala Ser Ser Thr Trp His Thr Glu Leu Thr Lys Thr Thr Asp
                435                 440                 445

Arg
```

<210> SEQ ID NO 20
<211> LENGTH: 449
<212> TYPE: PRT
<213> ORGANISM: Artificial Sequence
<220> FEATURE:
<223> OTHER INFORMATION: A polypeptide encoded by SEQ ID NO:9.

<400> SEQUENCE: 20

```
Met Asn Tyr Lys Asn Lys Ile Leu Val Ser Glu Ser Gly Leu Thr Gln
  1               5                  10                  15

Lys His Leu Ile His Gly Gly Glu Gly Leu Phe Gln His Glu Leu Arg
                 20                  25                  30

Ala Val Phe Ala Arg Asn Trp Leu Phe Leu Thr His Asp Ser Leu Ile
                 35                  40                  45

Pro Ser Pro Gly Asp Tyr Val Thr Ala Lys Met Gly Ile Asp Glu Val
 50                  55                  60

Ile Val Ser Arg Gln Ser Asp Gly Ser Ile Arg Ala Phe Leu Asn Val
 65                  70                  75                  80

Cys Arg His Arg Gly Lys Thr Leu Val Asn Ala Glu Ala Gly Asn Ala
                 85                  90                  95

Lys Gly Phe Val Cys Ser Tyr His Gly Trp Gly Phe Gly Ser Asn Gly
                100                 105                 110

Glu Leu Gln Ser Val Pro Phe Glu Lys Glu Leu Tyr Gly Glu Ser Leu
            115                 120                 125

Asn Lys Lys Cys Leu Gly Leu Lys Glu Val Ala Arg Val Glu Ser Phe
        130                 135                 140

His Gly Phe Ile Tyr Ala Cys Ile Asp Gln Glu Ala Pro Ser Leu Met
145                 150                 155                 160

Asp Tyr Leu Gly Asp Ala Ala Trp Tyr Leu Glu Pro Ile Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Cys Thr Gly Glu Ser Ile Phe
    210                 215                 220

Ser Ser Leu Ala Gly Asn Ala Val Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
                260                 265                 270
```

```
Gly Gly Ala Lys Gln Glu Arg Leu Asn Lys Glu Ile Gly Asp Val Arg
            275                 280                 285

Ala Arg Ile Tyr Arg Ser His Leu Asn Cys Thr Val Phe Pro Asn Asn
        290                 295                 300

Ser Val Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ala Val Gln Arg Thr Val
            340                 345                 350

Gly Pro Ala Gly Phe Trp Glu Ser Asp Asp Asn Asp Asn Met Glu Thr
            355                 360                 365

Ala Ser Gln Asn Gly Lys Lys Tyr Gln Ser Arg Asp Ser Asp Leu Ile
        370                 375                 380

Ser Asn Leu Gly Phe Gly Lys Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Gln Ala His Val Ser Ser Ser Asn Trp Ala Glu Phe
            420                 425                 430

Glu Asp Ala Ser Ser Thr Trp His Thr Glu Leu Thr Lys Thr Thr Asp
            435                 440                 445

Arg
```

<210> SEQ ID NO 21
<211> LENGTH: 449
<212> TYPE: PRT
<213> ORGANISM: Artificial Sequence
<220> FEATURE:
<223> OTHER INFORMATION: A polypeptide encoded by SEQ ID NO:10.

<400> SEQUENCE: 21

```
Met Asn Tyr Lys Asn Lys Asn Leu Val Ser Glu Ser Gly Leu Thr Gln
  1               5                  10                  15

Lys His Leu Ile His Gly Asp Glu Glu Leu Phe Gln Arg Glu Leu Glu
            20                  25                  30

Thr Ile Phe Ala Arg Asn Trp Leu Phe Leu Thr His Asp Ser Leu Ile
        35                  40                  45

Pro Ser Pro Gly Asp Tyr Val Thr Ala Lys Met Gly Val Asp Glu Val
 50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val His Ala Glu Ala Gly Asn Ala
                85                  90                  95

Lys Gly Phe Val Cys Ser Tyr His Gly Trp Gly Phe Gly Ala Asn Gly
            100                 105                 110

Glu Leu Gln Ser Val Pro Phe Glu Lys Glu Leu Tyr Gly Glu Ala Leu
        115                 120                 125

Asp Lys Lys Cys Met Gly Leu Lys Glu Val Ala Arg Val Glu Ser Phe
    130                 135                 140

His Gly Phe Ile Tyr Gly Cys Phe Asp Glu Glu Ala Pro Ser Leu Lys
145                 150                 155                 160

Asp Tyr Met Gly Asp Ala Gly Trp Tyr Leu Glu Pro Met Phe Lys His
                165                 170                 175

Ser Gly Gly Leu Glu Leu Ile Gly Pro Pro Gly Lys Val Ile Ile Lys
```

```
                        180                 185                 190
Ala Asn Trp Lys Ala Pro Ala Glu Asn Phe Thr Gly Asp Ala Tyr His
            195                 200                 205

Val Gly Trp Thr His Ala Ser Ser Leu Arg Ser Gly Gln Ser Val Phe
        210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Glu Val Arg
        275                 280                 285

Ala Arg Ile Tyr Arg Ser His Leu Asn Cys Thr Val Phe Pro Asn Asn
    290                 295                 300

Ser Phe Leu Thr Cys Ser Gly Val Phe Lys Val Trp His Pro Ile Asp
305                 310                 315                 320

Ala Asn Thr Thr Glu Val Trp Thr Tyr Ala Met Val Glu Lys Asp Met
                325                 330                 335

Pro Glu Asp Leu Lys Arg Arg Leu Val Asp Ala Val Gln Arg Thr Val
            340                 345                 350

Gly Pro Ala Gly Phe Trp Glu Ser Asp Asp Asn Asp Asn Met Glu Thr
        355                 360                 365

Val Ser Gln Asn Ala Lys Lys Tyr Gln Ser Arg Asp Gly Asp Leu Val
    370                 375                 380

Ser Asn Leu Gly Phe Gly Gly Asp Val Tyr Gly Asp Glu Val Tyr Pro
385                 390                 395                 400

Gly Ile Val Gly Lys Ser Ala Ile Gly Glu Thr Ser Tyr Arg Gly Phe
                405                 410                 415

Tyr Arg Ala Tyr Gly Ala His Ile Ser Ser Ser Trp Ala Glu Phe
            420                 425                 430

Glu Asp Val Ser Lys Asn Trp His Thr Glu Leu Ala Lys Thr Thr Asp
        435                 440                 445

Arg
```

<210> SEQ ID NO 22
<211> LENGTH: 447
<212> TYPE: PRT
<213> ORGANISM: Artificial Sequence
<220> FEATURE:
<223> OTHER INFORMATION: A polypeptide encoded by SEQ ID NO:11.

<400> SEQUENCE: 22

```
Met Ile Tyr Glu Asn Leu Val Ser Glu Ala Gly Leu Thr Gln Lys His
  1               5                  10                  15

Leu Ile His Gly Asp Lys Glu Leu Phe Gln His Glu Leu Lys Thr Ile
             20                  25                  30

Phe Ala Arg Asn Trp Leu Phe Leu Thr His Asp Ser Leu Ile Pro Ser
         35                  40                  45

Pro Gly Asp Tyr Val Thr Ala Lys Met Gly Val Asp Glu Val Ile Val
     50                  55                  60

Ser Arg Gln Asn Asp Gly Ser Val Arg Ala Phe Leu Asn Val Cys Arg
 65                  70                  75                  80

His Arg Gly Lys Thr Leu Val His Ala Glu Ala Gly Asn Ala Lys Gly
                 85                  90                  95
```

-continued

```
Phe Val Cys Ser Tyr His Gly Trp Gly Phe Gly Ser Asn Gly Glu Leu
                100                 105                 110

Gln Ser Val Pro Phe Glu Lys Glu Leu Tyr Gly Asp Thr Ile Lys Lys
            115                 120                 125

Lys Cys Leu Gly Leu Lys Glu Val Pro Arg Ile Glu Ser Phe His Gly
        130                 135                 140

Phe Ile Tyr Gly Cys Phe Asp Ala Glu Ala Pro Thr Leu Val Asp Tyr
145                 150                 155                 160

Leu Gly Asp Ala Ala Trp Tyr Leu Glu Pro Ile Phe Lys His Ser Gly
                165                 170                 175

Gly Leu Glu Leu Val Gly Pro Pro Gly Lys Val Ile Lys Ala Asn
            180                 185                 190

Trp Lys Ala Pro Ala Glu Asn Phe Val Gly Asp Ala Tyr His Val Gly
        195                 200                 205

Trp Thr His Ala Ser Ser Leu Arg Ser Gly Gln Ser Ile Phe Thr Pro
    210                 215                 220

Leu Ala Gly Asn Ala Met Leu Pro Pro Glu Gly Ala Gly Leu Gln Met
225                 230                 235                 240

Thr Ser Lys Tyr Gly Ser Gly Met Gly Val Leu Trp Asp Gly Tyr Ser
                245                 250                 255

Gly Val His Ser Ala Asp Leu Val Pro Glu Met Met Ala Phe Gly Gly
            260                 265                 270

Ala Lys Gln Glu Lys Leu Ala Lys Glu Ile Gly Asp Val Arg Ala Arg
        275                 280                 285

Ile Tyr Arg Ser His Leu Asn Cys Thr Val Phe Pro Asn Asn Ser Ile
    290                 295                 300

Leu Thr Cys Ser Gly Val Phe Lys Val Trp Asn Pro Ile Asp Glu Asn
305                 310                 315                 320

Thr Thr Glu Val Trp Thr Tyr Ala Ile Val Glu Lys Asp Met Pro Glu
                325                 330                 335

Asp Leu Lys Arg Arg Leu Ala Asp Ala Val Gln Arg Thr Val Gly Pro
            340                 345                 350

Ala Gly Phe Trp Glu Ser Asp Asp Asn Met Glu Thr Glu Ser
        355                 360                 365

Gln Asn Ala Lys Lys Tyr Gln Ser Ser Asn Ser Asp Leu Ile Ala Asn
    370                 375                 380

Leu Gly Phe Gly Lys Asp Val Tyr Gly Asp Glu Cys Tyr Pro Gly Val
385                 390                 395                 400

Val Ala Lys Ser Ala Ile Gly Glu Thr Ser Tyr Arg Gly Phe Tyr Arg
                405                 410                 415

Ala Tyr Gln Ala His Ile Ser Ser Ser Asn Trp Ala Glu Phe Glu Asn
            420                 425                 430

Thr Ser Arg Asn Trp His Thr Glu Leu Thr Lys Thr Thr Asp Arg
        435                 440                 445
```

<210> SEQ ID NO 23
<211> LENGTH: 447
<212> TYPE: PRT
<213> ORGANISM: Artificial Sequence
<220> FEATURE:
<223> OTHER INFORMATION: A polypeptide encoded by SEQ ID NO:12.

<400> SEQUENCE: 23

```
Met Ser Tyr Gln Asn Leu Val Ser Glu Ala Gly Leu Thr Gln Lys Leu
1               5                   10                  15
```

-continued

```
Leu Ile His Gly Asp Lys Glu Leu Phe Gln His Glu Leu Lys Thr Ile
             20                  25                  30

Phe Ala Arg Asn Trp Leu Phe Leu Thr His Asp Ser Leu Ile Pro Ser
         35                  40                  45

Pro Gly Asp Tyr Val Thr Ala Lys Met Gly Val Asp Glu Val Ile Val
     50                  55                  60

Ser Arg Gln Asn Asp Gly Ser Val Arg Ala Phe Leu Asn Val Cys Arg
 65                  70                  75                  80

His Arg Gly Lys Thr Leu Val His Thr Glu Ala Gly Asn Ala Lys Gly
                 85                  90                  95

Phe Val Cys Gly Tyr His Gly Trp Gly Tyr Gly Ser Asn Gly Glu Leu
            100                 105                 110

Gln Ser Val Pro Phe Glu Lys Glu Leu Tyr Gly Asp Ala Ile Lys Lys
        115                 120                 125

Lys Cys Leu Gly Leu Lys Glu Val Pro Arg Ile Glu Ser Phe His Gly
130                 135                 140

Phe Ile Tyr Gly Cys Phe Asp Ala Glu Ala Pro Pro Leu Ile Asp Tyr
145                 150                 155                 160

Leu Gly Asp Ala Ala Trp Tyr Leu Glu Pro Thr Phe Lys His Ser Gly
                165                 170                 175

Gly Leu Glu Leu Val Gly Pro Pro Gly Lys Val Val Lys Ala Asn
            180                 185                 190

Trp Lys Pro Phe Ala Glu Asn Phe Val Gly Asp Ile Tyr His Val Gly
        195                 200                 205

Trp Thr His Ala Ala Ala Leu Arg Ala Gly Gln Ser Val Phe Ser Ser
    210                 215                 220

Leu Ala Gly Asn Ala Lys Leu Pro Pro Glu Gly Ala Gly Leu Gln Met
225                 230                 235                 240

Thr Ser Lys Tyr Gly Ser Gly Met Gly Leu Thr Trp Asp Tyr Tyr Ser
                245                 250                 255

Gly Asn Phe Ser Ala Asp Met Val Pro Asp Leu Met Ala Phe Gly Ala
            260                 265                 270

Ala Lys Gln Glu Lys Leu Ala Lys Glu Ile Gly Asp Val Arg Ala Arg
        275                 280                 285

Ile Tyr Arg Ser Ile Leu Asn Gly Thr Val Phe Pro Asn Asn Ser Phe
    290                 295                 300

Leu Thr Gly Ser Ala Thr Phe Lys Val Trp Asn Pro Ile Asp Glu Asn
305                 310                 315                 320

Thr Thr Glu Val Trp Thr Tyr Ala Phe Val Glu Lys Asp Met Pro Glu
                325                 330                 335

Asp Leu Lys Arg Arg Leu Ala Asp Ala Gln Arg Ser Val Gly Pro
            340                 345                 350

Ala Gly Phe Trp Glu Ser Asp Asp Asn Glu Asn Met Glu Thr Leu Ser
        355                 360                 365

Gln Asn Ala Lys Lys Tyr Gln Ser Ser Asn Ser Asp Gln Ile Ala Ser
    370                 375                 380

Leu Gly Phe Gly Lys Asp Val Tyr Gly Asp Glu Cys Tyr Pro Gly Val
385                 390                 395                 400

Val Gly Lys Ser Ala Ile Gly Glu Thr Ser Tyr Arg Gly Phe Tyr Arg
                405                 410                 415

Ala Tyr Gln Ala His Ile Ser Ser Ser Asn Trp Ala Glu Phe Glu Asn
            420                 425                 430
```

```
Ala Ser Arg Asn Trp His Thr Glu Leu Thr Lys Thr Thr Asp Arg
        435                 440                 445
```

<210> SEQ ID NO 24
<211> LENGTH: 451
<212> TYPE: PRT
<213> ORGANISM: Artificial Sequence
<220> FEATURE:
<223> OTHER INFORMATION: A polypeptide encoded by SEQ ID NO:13.

<400> SEQUENCE: 24

```
Met Arg Gln Ala Ile Met Ser Tyr Gln Asn Leu Val Ser Glu Ala Gly
 1               5                  10                  15

Leu Thr Gln Lys His Leu Ile Tyr Gly Asp Lys Glu Leu Phe Gln His
                20                  25                  30

Glu Leu Lys Thr Ile Phe Ala Arg Asn Trp Leu Phe Leu Thr His Asp
            35                  40                  45

Ser Leu Ile Pro Ser Pro Gly Asp Tyr Val Lys Ala Lys Met Gly Val
        50                  55                  60

Asp Glu Val Ile Val Ser Arg Gln Asn Asp Gly Ser Val Arg Ala Phe
 65                 70                  75                  80

Leu Asn Val Cys Arg His Arg Gly Lys Thr Ile Val Asp Ala Glu Ala
                85                  90                  95

Gly Asn Ala Lys Gly Phe Val Cys Gly Tyr His Gly Trp Gly Tyr Gly
            100                 105                 110

Ser Asn Gly Glu Leu Gln Ser Val Pro Phe Glu Lys Glu Leu Tyr Gly
        115                 120                 125

Asp Ala Ile Lys Lys Lys Cys Leu Gly Leu Lys Glu Val Pro Arg Ile
    130                 135                 140

Glu Ser Phe His Gly Phe Ile Tyr Gly Cys Phe Asp Ala Glu Ala Pro
145                 150                 155                 160

Pro Leu Ile Asp Tyr Leu Gly Asp Val Ala Trp Tyr Leu Glu Pro Thr
                165                 170                 175

Phe Lys His Ser Gly Gly Leu Glu Leu Val Gly Pro Pro Ala Lys Val
            180                 185                 190

Val Val Lys Gly Asn Trp Lys Val Phe Ala Glu Asn Phe Val Gly Asp
        195                 200                 205

Ile Tyr His Ile Gly Trp Thr His Ala Ser Ile Leu Arg Ala Gly Gln
    210                 215                 220

Ala Ile Phe Ala Pro Leu Ala Gly Asn Ala Met Leu Pro Pro Glu Gly
225                 230                 235                 240

Thr Gly Leu Gln Ala Thr Thr Lys Tyr Gly Ser Gly Ile Gly Val Ser
                245                 250                 255

Leu Asp Ala Tyr Ser Gly Val Gln Ser Ala Asp Leu Val Pro Glu Met
            260                 265                 270

Met Ala Phe Gly Gly Ala Lys Gln Glu Lys Leu Ala Lys Glu Ile Gly
        275                 280                 285

Asp Val Arg Ala Arg Ile Tyr Arg Ser Gln Val Asn Gly Thr Val Phe
    290                 295                 300

Pro Asn Asn Cys Phe Leu Thr Gly Ala Gly Val Phe Lys Val Phe Asn
305                 310                 315                 320

Pro Ile Asp Glu Asn Thr Thr Glu Ala Trp Thr Tyr Ala Ile Val Glu
                325                 330                 335

Lys Asp Met Pro Glu Asp Leu Lys Arg Arg Leu Ala Asp Ala Ala Gln
            340                 345                 350
```

-continued

Arg Ser Val Gly Pro Ala Gly Tyr Trp Glu Ser Asp Asp Asn Asp Asn
            355                 360                 365

Met Val Leu Ser Gln Asn Ala Lys Lys Tyr Gln Ser Ser Asn Ser Asp
    370                 375                 380

Leu Ile Ala Asp Leu Gly Phe Gly Lys Asp Val Tyr Gly Asp Glu Cys
385                 390                 395                 400

Tyr Pro Gly Val Val Ser Lys Ser Ala Phe Ser Glu Thr Asn His Arg
                405                 410                 415

Gly Phe Tyr Arg Ala Tyr Gln Ala His Ile Ser Ser Asn Trp Ala
                420                 425                 430

Glu Phe Glu Asn Thr Ser Arg Asn Trp His Thr Glu Leu Thr Lys Thr
    435                 440                 445

Thr Asp Arg
        450

<210> SEQ ID NO 25
<211> LENGTH: 2265
<212> TYPE: DNA
<213> ORGANISM: Pseudomonas sp.

<400> SEQUENCE: 25

| | | | | | |
|---|---|---|---|---|---|
| gagggtagag | aaatcgaatg | ccccttgcat | caaggtcggt | ttgacgtttg | cacaggcaaa | 60 |
| gccctgtgcg | cacccgtgac | acagaacatc | aaaacatatc | cagtcaagat | tgagaacctg | 120 |
| cgcgtaatga | ttgatttgag | ctaagaattt | taacaggagg | caccccgggc | cctagagcgt | 180 |
| aatcaccccc | attccatctt | ttttaggtga | aacatgaat | acaataata | aaatcttggt | 240 |
| aagtgaatct | ggtctgagcc | aaaagcacct | gattcatggc | gatgaagaac | ttttccaaca | 300 |
| tgaactgaaa | accatttttg | cgcggaactg | gcttttctc | actcatgata | gcctgattcc | 360 |
| tgccccggc | gactatgtta | ccgcaaaaat | ggggattgac | gaggtcatcg | tctcccggca | 420 |
| gaacgacggt | tcgattcgtg | cttttctgaa | cgtttgccgg | catcgtggca | agacgctggt | 480 |
| gagcgtggaa | gccggcaatg | ccaaaggttt | tgtttgcagc | tatcacggct | ggggcttcgg | 540 |
| ctccaacggt | gaactgcaga | gcgttccatt | tgaaaaagat | ctgtacgcg | agtcgctcaa | 600 |
| taaaaaatgt | ctggggttga | agaagtcgc | tcgcgtggag | agcttccatg | gcttcatcta | 660 |
| cggttgcttc | gaccaggagg | cccctcctct | tatggactat | ctgggtgacg | ctgcttggta | 720 |
| cctggaacct | atgttcaagc | attccggcgg | tttagaactg | gtcggtcctc | caggcaaggt | 780 |
| tgtgatcaag | gccaactgga | aggcacccgc | ggaaaacttt | gtgggagatg | cataccacgt | 840 |
| gggttggacg | cacgcgtctt | cgcttcgctc | ggggggagtct | atcttctcgt | cgctcgctgg | 900 |
| caatgcggcg | ctaccacctg | aaggcgcagg | cttgcaaatg | acctccaaat | acggcagcgg | 960 |
| catggtgtg | ttgtgggacg | gatattcagg | tgtgcatagc | gcagacttgg | ttccggaatt | 1020 |
| gatggcattc | ggaggcgcaa | agcaggaaag | gctgaacaaa | gaaattggcg | atgttcgcgc | 1080 |
| tcggatttat | cgcagccacc | tcaactgcac | cgttttcccg | aacaacagca | tgctgacctg | 1140 |
| ctcgggtgtt | ttcaaagtat | ggaacccgat | cgacgcaaac | accaccgagg | tctggaccta | 1200 |
| cgccattgtc | gaaaaagaca | tgcctgagga | tctcaagcgc | cgcttggccg | actctgttca | 1260 |
| gcgaacgttc | gggcctgctg | gcttctggga | aagcgacgac | aatgacaata | tggaaacagc | 1320 |
| ttcgcaaaac | ggcaagaaat | atcaatcaag | agatagtgat | ctgctttcaa | accttggttt | 1380 |
| cggtgaggac | gtatacggcg | acgcggtcta | tccaggcgtc | gtcggcaaat | cggcgatcgg | 1440 |
| cgagaccagt | tatcgtggtt | tctaccgggc | ttaccaggca | cacgtcagca | gctccaactg | 1500 |

```
ggctgagttc gagcatgcct ctagtacttg gcatactgaa cttacgaaga ctactgatcg   1560
ctaacagacg agtcgaccat gatgatcaat attcaagaag acaagctggt ttccgcccac   1620
gacgccgaag agattcttcg tttcttcaat tgccacgact ctgctttgca acaagaagcc   1680
actacgctgc tgacccagga agcgcatttg ttggacattc aggcttaccg tgcttggtta   1740
gagcactgcg tggggtcaga ggtgcaatat caggtcattt cacgcgaact gcgcgcagct   1800
tcagagcgtc gttataagct caatgaagcc atgaacgttt acaacgaaaa ttttcagcaa   1860
ctgaaagttc gagttgagca tcaactggat ccgcaaaact ggggcaacag cccgaagctg   1920
cgctttactc gctttatcac caacgtccag gccgcaatgg acgtaaatga caaagagcta   1980
cttcacatcc gctccaacgt cattctgcac cgggcacgac gtggcaatca ggtcgatgtc   2040
ttctacgccg cccgggaaga taatggaaa cgtggcgaag gtggagtacg aaaattggtc   2100
cagcgattcg tcgattaccc agagcgcata cttcagacgc acaatctgat ggtctttctg   2160
tgattcagtg accatttta caaatggtca ctgcaaccgc ggtcaccatt aatcaaaggg   2220
aatgtacgtg tatgggcaat caacaagtcg tttcgataac cggtg                   2265
```

<210> SEQ ID NO 26
<211> LENGTH: 449
<212> TYPE: PRT
<213> ORGANISM: Pseudomonas sp.

<400> SEQUENCE: 26

```
Met Asn Tyr Asn Asn Lys Ile Leu Val Ser Glu Ser Gly Leu Ser Gln
  1               5                  10                  15

Lys His Leu Ile His Gly Asp Glu Glu Leu Phe Gln His Glu Leu Lys
             20                  25                  30

Thr Ile Phe Ala Arg Asn Trp Leu Phe Leu Thr His Asp Ser Leu Ile
         35                  40                  45

Pro Ala Pro Gly Asp Tyr Val Thr Ala Lys Met Gly Ile Asp Glu Val
     50                  55                  60

Ile Val Ser Arg Gln Asn Asp Gly Ser Ile Arg Ala Phe Leu Asn Val
 65                  70                  75                  80

Cys Arg His Arg Gly Lys Thr Leu Val Ser Val Glu Ala Gly Asn Ala
                 85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240
```

-continued

```
Gln Met Thr Ser Lys Tyr Gly Ser Gly Met Gly Val Leu Trp Asp Gly
            245                 250                 255
Tyr Ser Gly Val His Ser Ala Asp Leu Val Pro Glu Leu Met Ala Phe
        260                 265                 270
Gly Gly Ala Lys Gln Glu Arg Leu Asn Lys Glu Ile Gly Asp Val Arg
    275                 280                 285
Ala Arg Ile Tyr Arg Ser His Leu Asn Cys Thr Val Phe Pro Asn Asn
290                 295                 300
Ser Met Leu Thr Cys Ser Gly Val Phe Lys Val Trp Asn Pro Ile Asp
305                 310                 315                 320
Ala Asn Thr Thr Glu Val Trp Thr Tyr Ala Ile Val Glu Lys Asp Met
                325                 330                 335
Pro Glu Asp Leu Lys Arg Arg Leu Ala Asp Ser Val Gln Arg Thr Phe
            340                 345                 350
Gly Pro Ala Gly Phe Trp Glu Ser Asp Asp Asn Asp Asn Met Glu Thr
        355                 360                 365
Ala Ser Gln Asn Gly Lys Lys Tyr Gln Ser Arg Asp Ser Asp Leu Leu
    370                 375                 380
Ser Asn Leu Gly Phe Gly Glu Asp Val Tyr Gly Asp Ala Val Tyr Pro
385                 390                 395                 400
Gly Val Val Gly Lys Ser Ala Ile Gly Glu Thr Ser Tyr Arg Gly Phe
                405                 410                 415
Tyr Arg Ala Tyr Gln Ala His Val Ser Ser Ser Asn Trp Ala Glu Phe
            420                 425                 430
Glu His Ala Ser Ser Thr Trp His Thr Glu Leu Thr Lys Thr Thr Asp
        435                 440                 445
Arg
```

<210> SEQ ID NO 27
<211> LENGTH: 2265
<212> TYPE: DNA
<213> ORGANISM: Artificial Sequence
<220> FEATURE:
<223> OTHER INFORMATION: A sequence encoding an NDO mutant.

<400> SEQUENCE: 27

```
gagggtagag aaatcgaatg ccccttgcat caaggtcggt ttgacgtttg cacaggcaaa      60
gccctgtgcg cacccgtgac acagaacatc aaaacatatc cagtcaagat tgagaacctg     120
cgcgtaatga ttgatttgag ctaagaattt taacaggagg caccccgggc cctagagcgt     180
aatcaccccc attccatctt ttttaggtga aacatgaat tacaataata aaatcttggt       240
aagtgaatct ggtctgagcc aaaagcacct gattcatggc gatgaagaac ttttccaaca     300
tgaactgaaa accatttttg cgcggaactg gcttttctc actcatgata gcctgattcc      360
tgcccccggc gactatgtta ccgcaaaaat gggattgac gaggtcatcg tctcccggca      420
gaacgacggt tcgattcgtg cttttctgaa cgtttgccgg catcgtggca agacgctggt     480
gagcgtggaa gccggcaatg ccaaaggttt tgtttgcagc tatcacgct ggggcttcgg      540
ctccaacggt gaactgcaga gcgttccatt tgaaaaagat ctgtacggcg agtcgctcaa     600
taaaaaatgt ctggggttga agaagtcgc tcgcgtggag agcttccatg gcttcatcta      660
cggttgcttc gaccaggagg cccctcctct tatggactat ctgggtgacg ctgcttggta    720
cctggaacct atgttcaagc attccggcgg tttagaactg gtcggtcctc caggcaaggt    780
tgtgatcaag gccaactgga aggcaccccgc ggaaaacttt gtgggagatg cataccacgt    840
```

```
gggttggacg cacgcgtctt cgcttcgctc gggggagtct atcttctcgt cgctcgctgg        900
caatgcggcg ctaccacctg aaggcgcagg cttgcaaatg acctccaaat acggcagcgg        960
catgggtgtg ttgtgggacg atattcagg tgtgcatagc gcagacttgg ttccggaatt        1020
gatggcattc ggaggcgcaa agcaggaaag gctgaacaaa gaaattggcg atgttcgcgc        1080
tcggatttat cgcagccacc tcaactgcac cgttttcccg aacaacagca tgctgacctg        1140 ctcggtgtt ttcaaagtat ggaacccgat cgacgcaaac accaccgagg tctggaccta        1200
cgccattgtc gaaaaagaca tgcctgagga tctcaagcgc cgcttggccg actctgttca        1260
gcgaacgggc gggcctgctg gcttctggga aagcgacgca aatgacaata tggaaacagc        1320
ttcgcaaaac ggcaagaaat atcaatcaag agatagtgat ctgctttcaa accttggttt        1380
cggtgaggac gtatacggcg acgcggtcta tccaggcgtc gtcggcaaat cggcgatcgg        1440
cgagaccagt tatcgtggtt tctaccgggc ttaccaggca cacgtcagca gctccaactg        1500
ggctgagttc gagcatgcct ctagtacttg gcatactgaa cttacgaaga ctactgatcg        1560
ctaacagacg agtcgaccat gatgatcaat attcaagaag acaagctggt ttccgcccac        1620
gacgccgaag agattcttcg tttcttcaat tgccacgact ctgctttgca acaagaagcc        1680
actacgctgc tgacccagga agcgcatttg ttggacattc aggcttaccg tgcttggtta        1740
gagcactgcg tggggtcaga ggtgcaatat caggtcattt cacgcgaact gcgcgcagct        1800
tcagagcgtc gttataagct caatgaagcc atgaacgttt acaacgaaaa ttttcagcaa        1860
ctgaaagttc gagttgagca tcaactggat ccgcaaaact ggggcaacag cccgaagctg        1920
cgctttactc gctttatcac caacgtccag gccgcaatgg acgtaaatga caagagcta        1980 cttcacatcc gctccaacgt cattctgcac cgggcacgac gtggcaatca ggtcgatgtc        2040
ttctacgccg cccgggaaga taatggaaa cgtggcgaag gtggagtacg aaaattggtc        2100
cagcgattcg tcgattaccc agagcgcata cttcagacgc acaatctgat ggtctttctg        2160
tgattcagtg accatttta caaatggtca ctgcaaccgc ggtcaccatt aatcaaaggg        2220
aatgtacgtg tatgggcaat caacaagtcg tttcgataac cggtg                       2265
```

<210> SEQ ID NO 28
<211> LENGTH: 2265
<212> TYPE: DNA
<213> ORGANISM: Artificial Sequence
<220> FEATURE:
<223> OTHER INFORMATION: A sequence encoding an NDO mutant.

<400> SEQUENCE: 28

```
gagggtagag aaatcgaatg ccccttgcat caaggtcggt ttgacgtttg cacaggcaaa        60
gccctgtgcg cacccgtgac acagaacatc aaaacatatc cagtcaagat tgagaacctg       120
cgcgtaatga ttgatttgag ctaagaattt taacaggagg caccccgggc cctagagcgt       180
aatcaccccc attccatctt ttttaggtga aacatgaat tacaataata aaatcttggt        240
aagtgaatct ggtctgagcc aaaagcacct gattcatggc gatgaagaac ttttccaaca       300
tgaactgaaa accattttttg cgcggaactg gcttttttctc actcatgata gcctgattcc     360
tgcccccggc gactatgtta ccgcaaaaat ggggattgac gaggtcatcg tctcccggca       420
gaacgacggt tcgattcgtg cttttctgaa cgtttgccgg catcgtggca agacgctggt       480
gagcgtggaa gccggcaatg ccaaggtttt tgtttgcagc tatcacggct ggggcttcgg       540
ctccaacggt gaactgcaga gcgttccatt tgaaaaagat ctgtacgcg agtcgctcaa        600 taaaaaatgt ctggggttga agaagtcgc tcgcgtggag agcttccatg gcttcatcta       660
```

-continued

```
cggttgcttc gaccaggagg cccctcctct tatggactat ctgggtgacg ctgcttggta      720
cctggaacct atgttcaagc attccggcgg tttagaactg gtcggtcctc caggcaaggt      780
tgtgatcaag gccaactgga aggcacccgc ggaaaacttt gtgggagatg cataccacgt      840
gggttggacg cacgcgtctt cgcttcgctc ggggagtct atcttctcgt cgctcgctgg       900
caatgcggcg ctaccacctg aaggcgcagg cttgcaaatg acctccaaat acggcagcgg      960
catgggtgtg ttgtgggacg atattcagg tgtgcatagc gcagacttgg ttccggaatt     1020
gatggcattc ggaggcgcaa agcaggaaag gctgaacaaa gaaattggcg atgttcgcgc     1080
tcggatttat cgcagccacc tcaactgcac cgttttcccg aacaacagca tgctgacctg     1140 ctcggtgtt ttcaaagtat ggaacccgat cgacgcaaac accaccgagg tctggaccta     1200
cgccattgtc gaaaaagaca tgcctgagga tctcaagcgc cgcttggccg actctgttca     1260
gcgaacggcc gggcctgctg gcttctggga aagcgacgac aatgacaata tggaaacagc     1320
ttcgcaaaac ggcaagaaat atcaatcaag agatagtgat ctgctttcaa accttggttt     1380
cggtgaggac gtatacggcg acgcggtcta tccaggcgtc gtcggcaaat cggcgatcgg     1440
cgagaccagt tatcgtggtt tctaccgggc ttaccaggca cacgtcagca gctccaactg     1500
ggctgagttc gagcatgcct ctagtacttg gcatactgaa cttacgaaga ctactgatcg     1560
ctaacagacg agtcgaccat gatgatcaat attcaagaag acaagctggt ttccgcccac     1620
gacgccgaag agattcttcg tttcttcaat tgccacgact ctgctttgca acaagaagcc     1680
actacgctgc tgacccagga agcgcatttg ttggacattc aggcttaccg tgcttggtta     1740
gagcactgcg tggggtcaga ggtgcaatat caggtcattt cacgcgaact gcgcgcagct     1800
tcagagcgtc gttataagct caatgaagcc atgaacgttt acaacgaaaa ttttcagcaa     1860
ctgaaagttc gagttgagca tcaactggat ccgcaaaact ggggcaacag cccgaagctg     1920
cgctttactc gctttatcac caacgtccag gccgcaatgg acgtaaatga caaagagcta     1980
cttcacatcc gctccaacgt cattctgcac cgggcacgac gtggcaatca ggtcgatgtc     2040
ttctacgccg cccgggaaga taatggaaa cgtggcgaag gtggagtacg aaaattggtc      2100
cagcgattcg tcgattaccc agagcgcata cttcagacgc acaatctgat ggtctttctg     2160
tgattcagtg accatttta caaatggtca ctgcaaccgc ggtcaccatt aatcaaaggg      2220
aatgtacgtg tatgggcaat caacaagtcg tttcgataac cggtg                     2265
```

<210> SEQ ID NO 29
<211> LENGTH: 2265
<212> TYPE: DNA
<213> ORGANISM: Artificial Sequence
<220> FEATURE:
<223> OTHER INFORMATION: A sequence encoding an NDO mutant.

<400> SEQUENCE: 29

```
gagggtagag aaatcgaatg cccttgcat caaggtcggt ttgacgtttg cacaggcaaa       60
gccctgtgcg cacccgtgac acagaacatc aaaacatatc cagtcaagat tgagaacctg     120
cgcgtaatga ttgatttgag ctaagaattt taacaggagg caccccgggc cctagagcgt     180 aatcacccc attccatctt ttttaggtga aacatgaat tacaataata aaatcttggt       240
aagtgaatct ggtctgagcc aaaagcacct gattcatggc gatgaagaac ttttccaaca     300
tgaactgaaa accattttttg cgcggaactg gcttttttctc actcatgata gcctgattcc     360 tgccccccggc gactatgtta ccgcaaaaat ggggattgac gaggtcatcg tctcccggca     420
```

```
gaacgacggt tcgattcgtg cttttctgaa cgtttgccgg catcgtggca agacgctggt    480
gagcgtggaa gccggcaatg ccaaaggttt tgtttgcagc tatcacggct ggggcttcgg    540
ctccaacggt gaactgcaga gcgttccatt tgaaaaagat ctgtacggcg agtcgctcaa    600
taaaaaatgt ctggggttga agaagtcgc tcgcgtggag agcttccatg gcttcatcta    660
cggttgcttc gaccaggagg cccctcctct tatggactat ctgggtacgc tgcttggta    720 cctggaacct atgttcaagc attccggcgg tttagaactg gtcggtcctc caggcaaggt    780
tgtgatcaag gccaactgga aggcacccgc ggaaaacttt gtgggagatg cataccacgt    840
gggttggacg cacgcgtctt cgcttcgctc gggggagtct atcttctcgt cgctcgctgg    900
caatgcggcg ctaccacctg aaggcgcagg cttgcaaatg acctccaaat acggcagcgg    960
catgggtgtg ttgtgggacg atattcagg tgtgcatagc gcagacttgg ttccggaatt   1020
gatggcattc ggaggcgcaa agcaggaaag gctgaacaaa gaaattggcg atgttcgcgc   1080
tcggatttat cgcagccacc tcaactgcac cgttttcccg aacaacagca tgctgacctg   1140
ctcgggtgtt ttcaaagtat ggaacccgat cgacgcaaac accaccgagg tctggaccta   1200
cgccattgtc gaaaaagaca tgcctgagga tctcaagcgc cgcttggccg actctgttca   1260
gcgaacgacc gggcctgctg gcttctggga aagcgacgac aatgacaata tggaaacagc   1320
ttcgcaaaac ggcaagaaat atcaatcaag agatagtgat ctgctttcaa accttggttt   1380
cggtgaggac gtatacggcg acgcggtcta tccaggcgtc gtcggcaaat cggcgatcgg   1440
cgagaccagt tatcgtggtt tctaccgggc ttaccaggca cacgtcagca gctccaactg   1500
ggctgagttc gagcatgcct ctagtacttg gcatactgaa cttacgaaga ctactgatcg   1560
ctaacagacg agtcgaccat gatgatcaat attcaagaag acaagctggt ttccgcccac   1620
gacgccgaag agattcttcg tttcttcaat tgccacgact ctgctttgca acaagaagcc   1680
actacgctgc tgacccagga gcgcattttg ttggacattc aggcttaccg tgcttggtta   1740
gagcactgcg tggggtcaga ggtgcaatat caggtcattt cacgcgaact gcgcgcagct   1800
tcagagcgtc gttataagct caatgaagcc atgaacgttt acacgaaaaa ttttcagcaa   1860
ctgaaagttc gagttgagca tcaactggat ccgcaaaact ggggcaacag cccgaagctg   1920
cgctttactc gctttatcac caacgtccag gccgcaatgg acgtaaatga caaagagcta   1980
cttcacatcc gctccaacgt cattctgcac cgggcacgac gtggcaatca ggtcgatgtc   2040
ttctacgccg cccgggaaga taatggaaa cgtggcgaag gtggagtacg aaaattggtc   2100
cagcgattcg tcgattaccc agagcgcata cttcagacgc acaatctgat ggtctttctg   2160
tgattcagtg accatttta caaatggtca ctgcaaccgc ggtcaccatt aatcaagggg   2220
aatgtacgtg tatgggcaat caacaagtcg tttcgataac cggtg            2265
```

<210> SEQ ID NO 30
<211> LENGTH: 2265
<212> TYPE: DNA
<213> ORGANISM: Artificial Sequence
<220> FEATURE:
<223> OTHER INFORMATION: A sequence encoding an NDO mutant.

<400> SEQUENCE: 30

```
gagggtagag aaatcgaatg ccccttgcat caaggtcggt ttgacgtttg cacaggcaaa     60
gccctgtgcg cacccgtgac acagaacatc aaaacatatc cagtcaagat tgagaacctg    120
cgcgtaatga ttgatttgag ctaagaattt taacaggagg caccccgggc cctagagcgt    180
aatcaccccc attccatctt ttttaggtga aaacatgaat tacaataata aaatcttggt    240
```

-continued

```
aagtgaatct ggtctgagcc aaaagcacct gattcatggc gatgaagaac ttttccaaca      300
tgaactgaaa accattttg cgcggaactg gcttttctc actcatgata gcctgattcc       360
tgccccggc gactatgtta ccgcaaaaat ggggattgac gaggtcatcg tctcccggca       420
gaacgacggt tcgattcgtg cttttctgaa cgtttgccgg catcgtggca agacgctggt      480
gagcgtggaa gccggcaatg ccaaggtttt tgtttgcagc tatcacggct ggggcttcgg      540
ctccaacggt gaactgcaga gcgttccatt tgaaaaagat ctgtacggcg agtcgctcaa      600
taaaaaatgt ctggggttga agaagtcgc tcgcgtggag agcttccatg gcttcatcta       660
cggttgcttc gaccaggagg cccctcctct tatggactat ctgggtgacg ctgcttggta      720
cctggaacct atgttcaagc attccggcgg tttagaactg gtcggtcctc caggcaaggt      780
tgtgatcaag gccaactgga aggcacccgc ggaaaacttt gtgggagatg cataccacgt     840
gggttggacg cacgcgtctt cgcttcgctc ggggagtct atcttctcgt cgctcgctgg       900
caatgcggcg ctaccacctg aaggcgcagg cttgcaaatg acctccaaat acggcagcgg      960
catgggtgtg ttgtgggacg gatattcagg tgtgcatagc gcagacttgg ttccggaatt     1020
gatggcattc ggaggcgcaa agcaggaaag gctgaacaaa gaaattggcg atgttcgcgc     1080
tcggatttat cgcagccacc tcaactgcac cgtttttcccg aacaacagca tgctgacctg    1140
ctcgggtgtt ttcaaagtat ggaacccgat cgacgcaaac accaccgagg tctggaccta    1200
cgccattgtc gaaaaagaca tgcctgagga tctcaagcgc cgcttggccg actctgttca    1260
gcgaacgctc gggcctgctg gcttctggga aagcgacgca aatgacaata tggaaacagc    1320
ttcgcaaaac ggcaagaaat atcaatcaag agatagtgat ctgctttcaa accttggttt    1380
cggtgaggac gtatacggcg acgcggtcta tccaggcgtc gtcggcaaat cggcgatcgg    1440
cgagaccagt tatcgtggtt tctaccgggc ttaccaggca cacgtcagca gctccaactg    1500
ggctgagttc gagcatgcct ctagtacttg gcatactgaa cttacgaaga ctactgatcg    1560
ctaacagacg agtcgaccat gatgatcaat attcaagaag acaagctggt ttccgcccac    1620
gacgccgaag agattcttcg tttcttcaat tgccacgact ctgctttgca acaagaagcc    1680
actacgctgc tgacccagga agcgcatttg ttggacattc aggcttaccg tgcttggtta    1740
gagcactgcg tggggtcaga ggtgcaatat caggtcattt cacgcgaact gcgcgcagct    1800
tcagagcgtc gttataagct caatgaagcc atgaacgttt acaacgaaaa ttttcagcaa    1860
ctgaaagttc gagttgagca tcaactggat ccgcaaaact ggggcaacag cccgaagctg    1920
cgctttactc gctttatcac caacgtccag gccgcaatgg acgtaaatga caagagcta     1980
cttcacatcc gctccaacgt cattctgcac cgggcacgac gtggcaatca ggtcgatgtc    2040
ttctacgccg cccgggaaga taaatggaaa cgtggcgaag gtggagtacg aaaattggtc    2100
cagcgattcg tcgattaccc agagcgcata cttcagacgc acaatctgat ggtctttctg    2160
tgattcagtg accattttta caaatggtca ctgcaaccgc ggtcaccatt aatcaaaggg    2220
aatgtacgtg tatgggcaat caacaagtcg tttcgataac cggtg                     2265
```

<210> SEQ ID NO 31
<211> LENGTH: 2265
<212> TYPE: DNA
<213> ORGANISM: Artificial Sequence
<220> FEATURE:
<223> OTHER INFORMATION: A sequence encoding an NDO mutant.

<400> SEQUENCE: 31

-continued

```
gagggtagag aaatcgaatg cccctggcat caaggtcggt ttgacgtttg cacaggcaaa      60
gccctgtgcg cacccgtgac acagaacatc aaaacatatc cagtcaagat tgagaacctg    120
cgcgtaatga ttgatttgag ctaagaattt taacaggagg cacccggggc cctagagcgt    180
aatcacccccc attccatctt ttttaggtga aacatgaat tacaataata aaatcttggt    240
aagtgaatct ggtctgagcc aaaagcacct gattcatggc gatgaagaac ttttccaaca    300
tgaactgaaa accattttg cgcggaactg gcttttctc actcatgata gcctgattcc      360
tgccccccggc gactatgtta ccgcaaaaat ggggattgac gaggtcatcg tctcccggca    420
gaacgacggt tcgattcgtg cttttctgaa cgtttgccgg catcgtggca agacgctggt    480
gagcgtggaa gccggcaatg ccaaggtttt tgtttgcagc tatcacggct ggggcttcgg    540
ctccaacggt gaactgcaga gcgttccatt tgaaaaagat ctgtacggcg agtcgctcaa    600
taaaaatgt ctggggttga agaagtcgc tcgcgtggag agcttccatg gcttcatcta     660
cggttgcttc gaccaggagg cccctcctct tatggactat ctgggtgacg ctgcttggta    720
cctggaacct atgttcaagc attccggcgg tttagaactg gtcggtcctc caggcaaggt    780
tgtgatcaag gccaactgga aggcacccgc ggaaaacttt gtgggagatg cataccacgt    840
gggttggacg cacgcgtctt cgcttcgctc gggggagtct atcttctcgt cgctcgctgg    900
caatgcggcg ctaccacctg aaggcgcagg cttgcaaatg acctccaaat acggcagcgg    960
catgggtgtg ttgtgggacg atattcagg tgtgcatagc gcagacttgg ttccggaatt   1020
gatggcattc ggaggcgcaa agcaggaaag gctgaacaaa gaaattggcg atgttcgcgc   1080
tcggatttat cgcagccacc tcaactgcac cgttttcccg aacaacagca tgctgacctg   1140
ctcgggtgtt ttcaaagtat ggaacccgat cgacgcaaac accaccgagg tctggaccta   1200
cgccattgtc gaaaaagaca tgcctgagga tctcaagcgc cgcttggccg actctgttca   1260
gcgaacgatc gggcctgctg gcttctggga aagcgacgac aatgacaata tggaaacagc   1320
ttcgcaaaac ggcaagaaat atcaatcaag agatagtgat ctgcttcaa accttggttt    1380
cggtgaggac gtatacggcg acgcggtcta tccaggcgtc gtcggcaaat cggcgatcgg   1440
cgagaccagt tatcgtggtt tctaccgggc ttaccaggca cacgtcagca gctccaactg   1500
ggctgagttc gagcatgcct ctagtacttg gcatactgaa cttacgaaga ctactgatcg   1560
ctaacagacg agtcgaccat gatgatcaat attcaagaag acaagctggt ttccgcccac   1620
gacgccgaag agattcttcg tttcttcaat tgccacgact ctgctttgca acaagaagcc   1680
actacgctgc tgacccagga agcgcatttg ttggacattc aggcttaccg tgcttggtta   1740
gagcactgcg tggggtcaga ggtgcaatat caggtcattt cacgcgaact gcgcgcagct   1800
tcagagcgtc gttataagct caatgaagcc atgaacgttt acaacgaaaa ttttcagcaa   1860
ctgaaagttc gagttgagca tcaactggat ccgcaaaact ggggcaacag cccgaagctg   1920
cgctttactc gctttatcac caacgtccag gccgcaatgg acgtaaatga caagagcta    1980
cttcacatcc gctccaacgt cattctgcac cgggcacgac gtggcaatca ggtcgatgtc   2040
ttctacgccg cccgggaaga taatggaaa cgtggcgaag tggagtacg aaaattggtc     2100
cagcgattcg tcgattaccc agagcgcata cttcagacgc acaatctgat ggtctttctg   2160
tgattcagtg accatttta caaatggtca ctgcaaccgc ggtcaccatt aatcaaaggg    2220
aatgtacgtg tatgggcaat caacaagtcg tttcgataac cggtg                   2265
```

<210> SEQ ID NO 32
<211> LENGTH: 449

```
<212> TYPE: PRT
<213> ORGANISM: Artificial Sequence
<220> FEATURE:
<223> OTHER INFORMATION: A polypeptide encoded by SEQ ID NO:27.

<400> SEQUENCE: 32

Met Asn Tyr Asn Asn Lys Ile Leu Val Ser Glu Gly Leu Ser Gln
 1               5                  10                  15

Lys His Leu Ile His Gly Asp Glu Glu Leu Phe Gln His Glu Leu Lys
             20                  25                  30

Thr Ile Phe Ala Arg Asn Trp Leu Phe Leu Thr His Asp Ser Leu Ile
         35                  40                  45

Pro Ala Pro Gly Asp Tyr Val Thr Ala Lys Met Gly Ile Asp Glu Val
     50                  55                  60

Ile Val Ser Arg Gln Asn Asp Gly Ser Ile Arg Ala Phe Leu Asn Val
 65                  70                  75                  80

Cys Arg His Arg Gly Lys Thr Leu Val Ser Val Glu Ala Gly Asn Ala
                 85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
    290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Gly
            340                 345                 350

Gly Pro Ala Gly Phe Trp Glu Ser Asp Asn Asp Asn Met Glu Thr
        355                 360                 365

Ala Ser Gln Asn Gly Lys Lys Tyr Gln Ser Arg Asp Ser Asp Leu Leu
    370                 375                 380
```

```
Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
            405                 410                 415

Tyr Arg Ala Tyr Gln Ala His Val Ser Ser Asn Trp Ala Glu Phe
            420                 425                 430

Glu His Ala Ser Ser Thr Trp His Thr Glu Leu Thr Lys Thr Thr Asp
        435                 440                 445

Arg

<210> SEQ ID NO 33
<211> LENGTH: 449
<212> TYPE: PRT
<213> ORGANISM: Artificial Sequence
<220> FEATURE:
<223> OTHER INFORMATION: A polypeptide encoded by SEQ ID NO:28.

<400> SEQUENCE: 33

Met Asn Tyr Asn Lys Ile Leu Val Ser Glu Ser Gly Leu Ser Gln
1               5                   10                  15

Lys His Leu Ile His Gly Asp Glu Glu Leu Phe Gln His Glu Leu Lys
            20                  25                  30

Thr Ile Phe Ala Arg Asn Trp Leu Phe Leu Thr His Asp Ser Leu Ile
        35                  40                  45

Pro Ala Pro Gly Asp Tyr Val Thr Ala Lys Met Gly Ile Asp Glu Val
    50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
                85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
```

-continued

```
            290                 295                 300
Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Ala
            340                 345                 350

Gly Pro Ala Gly Phe Trp Glu Ser Asp Asn Asp Asn Met Glu Thr
            355                 360                 365

Ala Ser Gln Asn Gly Lys Lys Tyr Gln Ser Arg Asp Ser Asp Leu Leu
        370                 375                 380

Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Gln Ala His Val Ser Ser Asn Trp Ala Glu Phe
                420                 425                 430

Glu His Ala Ser Ser Thr Trp His Thr Glu Leu Thr Lys Thr Thr Asp
            435                 440                 445

Arg
```

<210> SEQ ID NO 34
<211> LENGTH: 449
<212> TYPE: PRT
<213> ORGANISM: Artificial Sequence
<220> FEATURE:
<223> OTHER INFORMATION: A polypeptide encoded by SEQ ID NO:29.

<400> SEQUENCE: 34

```
Met Asn Tyr Asn Lys Ile Leu Val Ser Glu Ser Gly Leu Ser Gln
1               5                   10                  15

Lys His Leu Ile His Gly Asp Glu Glu Leu Phe Gln His Glu Leu Lys
                20                  25                  30

Thr Ile Phe Ala Arg Asn Trp Leu Phe Leu Thr His Asp Ser Leu Ile
            35                  40                  45

Pro Ala Pro Gly Asp Tyr Val Thr Ala Lys Met Gly Ile Asp Glu Val
50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
                85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
    130                 135                 140

His Gly Phe Ile Tyr Gly Cys Phe Asp Gln Glu Ala Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205
```

```
Val Gly Trp Thr His Ala Ser Ser Leu Arg Ser Gly Glu Ser Ile Phe
    210                 215                 220
Ser Ser Leu Ala Gly Asn Ala Ala Leu Pro Pro Glu Gly Ala Gly Leu
225                 230                 235                 240
Gln Met Thr Ser Lys Tyr Gly Ser Gly Met Gly Val Leu Trp Asp Gly
                245                 250                 255
Tyr Ser Gly Val His Ser Ala Asp Leu Val Pro Glu Leu Met Ala Phe
            260                 265                 270
Gly Gly Ala Lys Gln Glu Arg Leu Asn Lys Glu Ile Gly Asp Val Arg
        275                 280                 285
Ala Arg Ile Tyr Arg Ser His Leu Asn Cys Thr Val Phe Pro Asn Asn
    290                 295                 300
Ser Met Leu Thr Cys Ser Gly Val Phe Lys Val Trp Asn Pro Ile Asp
305                 310                 315                 320
Ala Asn Thr Thr Glu Val Trp Thr Tyr Ala Ile Val Glu Lys Asp Met
                325                 330                 335
Pro Glu Asp Leu Lys Arg Arg Leu Ala Asp Ser Val Gln Arg Thr Thr
            340                 345                 350
Gly Pro Ala Gly Phe Trp Glu Ser Asp Asp Asn Asp Asn Met Glu Thr
        355                 360                 365
Ala Ser Gln Asn Gly Lys Lys Tyr Gln Ser Arg Asp Ser Asp Leu Leu
    370                 375                 380
Ser Asn Leu Gly Phe Gly Glu Asp Val Tyr Gly Asp Ala Val Tyr Pro
385                 390                 395                 400
Gly Val Val Gly Lys Ser Ala Ile Gly Glu Thr Ser Tyr Arg Gly Phe
                405                 410                 415
Tyr Arg Ala Tyr Gln Ala His Val Ser Ser Asn Trp Ala Glu Phe
            420                 425                 430
Glu His Ala Ser Ser Thr Trp His Thr Glu Leu Thr Lys Thr Thr Asp
        435                 440                 445
Arg
```

<210> SEQ ID NO 35
<211> LENGTH: 449
<212> TYPE: PRT
<213> ORGANISM: Artificial Sequence
<220> FEATURE:
<223> OTHER INFORMATION: A polypeptide encoded by SEQ ID NO:30.

<400> SEQUENCE: 35

```
Met Asn Tyr Asn Asn Lys Ile Leu Val Ser Glu Ser Gly Leu Ser Gln
  1               5                  10                  15
Lys His Leu Ile His Gly Asp Glu Glu Leu Phe Gln His Glu Leu Lys
                 20                  25                  30
Thr Ile Phe Ala Arg Asn Trp Leu Phe Leu Thr His Asp Ser Leu Ile
             35                  40                  45
Pro Ala Pro Gly Asp Tyr Val Thr Ala Lys Met Gly Ile Asp Glu Val
         50                  55                  60
Ile Val Ser Arg Gln Asn Asp Gly Ser Ile Arg Ala Phe Leu Asn Val
65                  70                  75                  80
Cys Arg His Arg Gly Lys Thr Leu Val Ser Val Glu Ala Gly Asn Ala
                 85                  90                  95
Lys Gly Phe Val Cys Ser Tyr His Gly Trp Gly Phe Gly Ser Asn Gly
                100                 105                 110
```

-continued

```
Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
    130                 135                 140

His Gly Phe Ile Tyr Gly Cys Phe Asp Gln Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
                180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
    290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
                325                 330                 335

Pro Glu Asp Leu Lys Arg Arg Leu Ala Asp Ser Val Gln Arg Thr Leu
            340                 345                 350

Gly Pro Ala Gly Phe Trp Glu Ser Asp Asp Asn Asp Asn Met Glu Thr
        355                 360                 365

Ala Ser Gln Asn Gly Lys Lys Tyr Gln Ser Arg Asp Ser Asp Leu Leu
    370                 375                 380

Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Gln Ala His Val Ser Ser Asn Trp Ala Glu Phe
            420                 425                 430

Glu His Ala Ser Ser Thr Trp His Thr Glu Leu Thr Lys Thr Thr Asp
        435                 440                 445

Arg
```

<210> SEQ ID NO 36
<211> LENGTH: 449
<212> TYPE: PRT
<213> ORGANISM: Artificial Sequence
<220> FEATURE:
<223> OTHER INFORMATION: A polypeptide encoded by SEQ ID NO:31.

<400> SEQUENCE: 36

```
Met Asn Tyr Asn Asn Lys Ile Leu Val Ser Glu Ser Gly Leu Ser Gln
1               5                   10                  15

Lys His Leu Ile His Gly Asp Glu Glu Leu Phe Gln His Glu Leu Lys
```

-continued

```
                20                  25                  30
Thr Ile Phe Ala Arg Asn Trp Leu Phe Leu Thr His Asp Ser Leu Ile
             35                  40                  45
Pro Ala Pro Gly Asp Tyr Val Thr Ala Lys Met Gly Ile Asp Glu Val
 50                  55                  60
Ile Val Ser Arg Gln Asn Asp Gly Ser Ile Arg Ala Phe Leu Asn Val
 65                  70                  75                  80
Cys Arg His Arg Gly Lys Thr Leu Val Ser Val Glu Ala Gly Asn Ala
                 85                  90                  95
Lys Gly Phe Val Cys Ser Tyr His Gly Trp Gly Phe Gly Ser Asn Gly
            100                 105                 110
Glu Leu Gln Ser Val Pro Phe Glu Lys Asp Leu Tyr Gly Glu Ser Leu
            115                 120                 125
Asn Lys Lys Cys Leu Gly Leu Lys Glu Val Ala Arg Val Glu Ser Phe
            130                 135                 140
His Gly Phe Ile Tyr Gly Cys Phe Asp Gln Glu Ala Pro Pro Leu Met
145                 150                 155                 160
Asp Tyr Leu Gly Asp Ala Ala Trp Tyr Leu Glu Pro Met Phe Lys His
                165                 170                 175
Ser Gly Gly Leu Glu Leu Val Gly Pro Pro Gly Lys Val Val Ile Lys
            180                 185                 190
Ala Asn Trp Lys Ala Pro Ala Glu Asn Phe Val Gly Asp Ala Tyr His
            195                 200                 205
Val Gly Trp Thr His Ala Ser Ser Leu Arg Ser Gly Glu Ser Ile Phe
            210                 215                 220
Ser Ser Leu Ala Gly Asn Ala Ala Leu Pro Pro Glu Gly Ala Gly Leu
225                 230                 235                 240
Gln Met Thr Ser Lys Tyr Gly Ser Gly Met Gly Val Leu Trp Asp Gly
                245                 250                 255
Tyr Ser Gly Val His Ser Ala Asp Leu Val Pro Glu Leu Met Ala Phe
                260                 265                 270
Gly Gly Ala Lys Gln Glu Arg Leu Asn Lys Glu Ile Gly Asp Val Arg
            275                 280                 285
Ala Arg Ile Tyr Arg Ser His Leu Asn Cys Thr Val Phe Pro Asn Asn
            290                 295                 300
Ser Met Leu Thr Cys Ser Gly Val Phe Lys Val Trp Asn Pro Ile Asp
305                 310                 315                 320
Ala Asn Thr Thr Glu Val Trp Thr Tyr Ala Ile Val Glu Lys Asp Met
                325                 330                 335
Pro Glu Asp Leu Lys Arg Arg Leu Ala Asp Ser Val Gln Arg Thr Ile
            340                 345                 350
Gly Pro Ala Gly Phe Trp Glu Ser Asp Asp Asn Asp Asn Met Glu Thr
            355                 360                 365
Ala Ser Gln Asn Gly Lys Lys Tyr Gln Ser Arg Asp Ser Asp Leu Leu
            370                 375                 380
Ser Asn Leu Gly Phe Gly Glu Asp Val Tyr Gly Asp Ala Val Tyr Pro
385                 390                 395                 400
Gly Val Val Gly Lys Ser Ala Ile Gly Glu Thr Ser Tyr Arg Gly Phe
            405                 410                 415
Tyr Arg Ala Tyr Gln Ala His Val Ser Ser Asn Trp Ala Glu Phe
            420                 425                 430
Glu His Ala Ser Ser Thr Trp His Thr Glu Leu Thr Lys Thr Thr Asp
            435                 440                 445
```

Arg

<210> SEQ ID NO 37
<211> LENGTH: 22
<212> TYPE: DNA
<213> ORGANISM: Artificial Sequence
<220> FEATURE:
<223> OTHER INFORMATION: A mutagenic oligonucleotide.

<400> SEQUENCE: 37
ttcagcgaac ggtcgggcct gc                                    22

<210> SEQ ID NO 38
<211> LENGTH: 27
<212> TYPE: DNA
<213> ORGANISM: Artificial Sequence
<220> FEATURE:
<223> OTHER INFORMATION: A tetracycline repair oligonucleotide.

<400> SEQUENCE: 38
gccgggcctc ttgcgggata tcgtcca                               27

<210> SEQ ID NO 39
<211> LENGTH: 27
<212> TYPE: DNA
<213> ORGANISM: Artificial Sequence
<220> FEATURE:
<223> OTHER INFORMATION: An ampicillin knockout oligonucleotide.

<400> SEQUENCE: 39
gttgccattg ctgcaggcat cgtggtg                               27

<210> SEQ ID NO 40
<211> LENGTH: 33
<212> TYPE: DNA
<213> ORGANISM: Artificial Sequence
<220> FEATURE:
<223> OTHER INFORMATION: A mutagenic oligonucleotide.

<400> SEQUENCE: 40
gaggcacccg cggaagcttt tgtgggagat gca                        33

<210> SEQ ID NO 41
<211> LENGTH: 30
<212> TYPE: DNA
<213> ORGANISM: Artificial Sequence
<220> FEATURE:
<223> OTHER INFORMATION: A mutagenic oligonucleotide.

<400> SEQUENCE: 41
gcacccgcgg aacaatttgt gggagatgca                            30

<210> SEQ ID NO 42
<211> LENGTH: 21
<212> TYPE: DNA
<213> ORGANISM: Artificial Sequence
<220> FEATURE:
<223> OTHER INFORMATION: A mutagenic oligonucleotide.

<400> SEQUENCE: 42
ccgcggaaag ctttgtggga g                                     21

<210> SEQ ID NO 43
<211> LENGTH: 24
<212> TYPE: DNA

```
<213> ORGANISM: Artificial Sequence
<220> FEATURE:
<223> OTHER INFORMATION: A mutagenic oligonucleotide.

<400> SEQUENCE: 43
ccgcggaaaa gcttgtggga gatg                                             24

<210> SEQ ID NO 44
<211> LENGTH: 23
<212> TYPE: DNA
<213> ORGANISM: Artificial Sequence
<220> FEATURE:
<223> OTHER INFORMATION: A mutagenic oligonucleotide.

<400> SEQUENCE: 44
cgcggaaaac gttgtgggag atg                                              23

<210> SEQ ID NO 45
<211> LENGTH: 23
<212> TYPE: DNA
<213> ORGANISM: Artificial Sequence
<220> FEATURE:
<223> OTHER INFORMATION: A mutagenic oligonucleotide.

<400> SEQUENCE: 45
atattcaggt gcgcatagcg cag                                              23

<210> SEQ ID NO 46
<211> LENGTH: 34
<212> TYPE: DNA
<213> ORGANISM: Artificial Sequence
<220> FEATURE:
<223> OTHER INFORMATION: A mutagenic oligonucleotide.

<400> SEQUENCE: 46
ggacggatat tcagggctcc atagcgcaga cttg                                  34

<210> SEQ ID NO 47
<211> LENGTH: 33
<212> TYPE: DNA
<213> ORGANISM: Artificial Sequence
<220> FEATURE:
<223> OTHER INFORMATION: A mutagenic oligonucleotide.

<400> SEQUENCE: 47
gacggatatt caggtaacca tagcgcagac ttg                                   33

<210> SEQ ID NO 48
<211> LENGTH: 30
<212> TYPE: DNA
<213> ORGANISM: Artificial Sequence
<220> FEATURE:
<223> OTHER INFORMATION: A mutagenic oligonucleotide.

<400> SEQUENCE: 48
ggtgttttca aagtcgcgaa cccgatcgac                                       30

<210> SEQ ID NO 49
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 49
ctgttcagcg aaacttcggg cctgct                                           26
```

<210> SEQ ID NO 50
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 50
ctgttcagcg aaggttcggg cctgct                                26

<210> SEQ ID NO 51
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 51
ctgttcagcg aagcttcggg cctgct                                26

<210> SEQ ID NO 52
<211> LENGTH: 22
<212> TYPE: DNA
<213> ORGANISM: Artificial Sequence
<220> FEATURE:
<223> OTHER INFORMATION: A mutagenic oligonucleotide.

<400> SEQUENCE: 52
ttcagcgaac gctcgggcct gc                                    22

<210> SEQ ID NO 53
<211> LENGTH: 30
<212> TYPE: DNA
<213> ORGANISM: Artificial Sequence
<220> FEATURE:
<223> OTHER INFORMATION: A mutagenic oligonucleotide.

<400> SEQUENCE: 53
ggcctgctgg cttcgcggaa agcgacgaca                            30

<210> SEQ ID NO 54
<211> LENGTH: 21
<212> TYPE: DNA
<213> ORGANISM: Artificial Sequence
<220> FEATURE:
<223> OTHER INFORMATION: A mutagenic oligonucleotide.

<400> SEQUENCE: 54
gaaagcgacg ccaatgacaa t                                     21

<210> SEQ ID NO 55
<211> LENGTH: 30
<212> TYPE: DNA
<213> ORGANISM: Artificial Sequence
<220> FEATURE:
<223> OTHER INFORMATION: A mutagenic oligonucleotide.

<400> SEQUENCE: 55
acgacaatga caattgggaa acagcttcgc                            30

<210> SEQ ID NO 56
<211> LENGTH: 2265
<212> TYPE: DNA
<213> ORGANISM: Artificial Sequence
<220> FEATURE:

<223> OTHER INFORMATION: A sequence encoding an NDO mutant.

<400> SEQUENCE: 56

```
gagggtagag aaatcgaatg cccattgcat caaggtcggt ttgacgtttg cacaggcaaa      60
gccctgtgcg cacccgtgac acagaacatc aaaacatatc cagtcaagat tgagaacctg     120
cgcgtaatga ttgatttgag ctaagaattt taacaggagg caccccgggc cctagagcgt     180
aatcaccccc attccatctt ttttaggtga aacatgaat tacaataata aaatcttggt      240
aagtgaatct ggtctgagcc aaaagcacct gattcatggc gatgaagaac ttttccaaca     300
tgaactgaaa accattttg cgcgaactg gcttttctc actcatgata gcctgattcc        360
tgcccccggc gactatgtta ccgcaaaaat ggggattgac gaggtcatcg tctcccggca     420
gaacgacggt tcgattcgtg cttttctgaa cgtttgccgg catcgtggca agacgctggt     480
gagcgtggaa gccggcaatg ccaaggtttt tgtttgcagc tatcacggct ggggcttcgg     540
ctccaacggt gaactgcaga gcgttccatt tgaaaaagat ctgtacgcg agtcgctcaa      600
taaaaatgt ctggggttga agaagtcgc tcgcgtggag agcttccatg gcttcatcta      660
cggttgcttc gaccaggagg cccctcctct tatggactat ctgggtgacg ctgcttggta     720
cctggaacct atgttcaagc attccggcgg tttagaactg gtcggtcctc caggcaaggt     780
tgtgatcaag gccaactgga aggcacccgc ggaaaacttt gtgggagatg cataccacgt     840
gggttggacg cacgcgtctt cgcttcgctc gggggagtct atcttctcgt cgctcgctgg     900
caatgcggcg ctaccacctg aaggcgcagg cttgcaaatg acctccaaat acggcagcgg     960
catgggtgtg ttgtgggacg atattcagg tgtgcatagc gcagacttgg ttccggaatt    1020
gatggcattc ggaggcgcaa agcaggaaag gctgaacaaa gaaattggcg atgttcgcgc    1080
tcggatttat cgcagccacc tcaactgcac cgttttcccg aacaacagca tgctgacctg    1140
ctcgggtgtt ttcaaagtat ggaacccgat cgacgcaaac accaccgagg tctggaccta    1200
cgccattgtc gaaaaagaca tgcctgagga tctcaagcgc cgcttggccg actctgttca    1260
gcgaacgtgg gggcctgctg gcttctggga aagcgacgac aatgacaata tggaaacagc    1320
ttcgcaaaac ggcaagaaat atcaatcaag agatagtgat ctgctttcaa accttggttt    1380
cggtgaggac gtatacggcg acgcggtcta tccaggcgtc gtcggcaaat cggcgatcgg    1440
cgagaccagt tatcgtggtt tctaccgggc ttaccaggca cacgtcagca gctccaactg    1500
ggctgagttc gagcatgcct ctagtacttg gcatactgaa cttacgaaga ctactgatcg    1560
ctaacagacg agtcgaccat gatgatcaat attcaagaag acaagctggt ttccgcccac    1620
gacgccgaag agattcttcg tttcttcaat tgccacgact ctgctttgca acaagaagcc    1680
actacgctgc tgacccagga agcgcatttg ttggacattc aggcttaccg tgcttggtta    1740
gagcactgcg tggggtcaga ggtgcaatat caggtcattt cacgcgaact gcgcgcagct    1800
tcagagcgtc gttataagct caatgaagcc atgaacgttt acaacgaaaa ttttcagcaa    1860
ctgaaagttc gagttgagca tcaactggat ccgcaaaact ggggcaacag cccgaagctg    1920
cgctttactc gctttatcac caacgtccag gccgcaatgg acgtaaatga caagagcta    1980
cttcacatcc gctccaacgt cattctgcac cgggcacgac gtggcaatca ggtcgatgtc    2040
ttctacgccg cccgggaaga taatggaaa cgtggcgaag gtggagtacg aaaattggtc    2100
cagcgattcg tcgattaccc agagcgcata cttcagacgc acaatctgat ggtctttctg    2160
tgattcagtg accattttta caaatggtca ctgcaaccgc ggtcaccatt aatcaaaggg    2220
aatgtacgtg tatgggcaat caacaagtcg tttcgataac cggtg                    2265
```

<210> SEQ ID NO 57
<211> LENGTH: 2265
<212> TYPE: DNA
<213> ORGANISM: Artificial Sequence
<220> FEATURE:
<223> OTHER INFORMATION: A sequence encoding an NDO mutant.

<400> SEQUENCE: 57

| | | | | | |
|---|---|---|---|---|---|
| gagggtagag | aaatcgaatg | ccccttgcat | caaggtcggt | ttgacgtttg | cacaggcaaa | 60 |
| gccctgtgcg | cacccgtgac | acagaacatc | aaaacatatc | cagtcaagat | tgagaacctg | 120 |
| cgcgtaatga | ttgatttgag | ctaagaattt | taacaggagg | caccccgggc | cctagagcgt | 180 |
| aatcacccccc | attccatctt | ttttaggtga | aacatgaat | tacaataata | aaatcttggt | 240 |
| aagtgaatct | ggtctgagcc | aaaagcacct | gattcatggc | gatgaagaac | ttttccaaca | 300 |
| tgaactgaaa | accattttg | cgcggaactg | gcttttctc | actcatgata | gcctgattcc | 360 |
| tgcccccggc | gactatgtta | ccgcaaaaat | ggggattgac | gaggtcatcg | tctcccggca | 420 |
| gaacgacggt | tcgattcgtg | cttttctgaa | cgtttgccgg | catcgtggca | agacgctggt | 480 |
| gagcgtggaa | gccggcaatg | ccaaaggttt | tgtttgcagc | tatcacggct | ggggcttcgg | 540 |
| ctccaacggt | gaactgcaga | gcgttccatt | tgaaaaagat | ctgtacgcg | agtcgctcaa | 600 |
| taaaaatgt | ctggggttga | agaagtcgc | tcgcgtggag | agcttccatg | gcttcatcta | 660 |
| cggttgcttc | gaccaggagg | ccctcctct | tatggactat | ctgggtgacg | ctgcttggta | 720 |
| cctggaacct | atgttcaagc | attccggcgg | tttagaactg | gtcggtcctc | caggcaaggt | 780 |
| tgtgatcaag | gccaactgga | aggcacccgc | ggaaaacttt | gtgggagatg | cataccacgt | 840 |
| gggttggacac | acgcgtctt | cgcttcgctc | ggggagtct | atcttctcgt | cgctcgctgg | 900 |
| caatgcggcg | ctaccacctg | aaggcgcagg | cttgcaaatg | acctccaaat | acggcagcgg | 960 |
| catgggtgtg | ttgtgggacg | gatattcagg | tgtgcatagc | gcagacttgg | ttccggaatt | 1020 |
| gatggcattc | ggaggcgcaa | agcaggaaag | gctgaacaaa | gaaattggcg | atgttcgcgc | 1080 |
| tcggatttat | cgcagccacc | tcaactgcac | cgttttcccg | aacaacagca | tgctgacctg | 1140 |
| ctcgggtgtt | ttcaaagtat | ggaacccgat | cgacgcaaac | accaccgagg | tctggaccta | 1200 |
| cgccattgtc | gaaaaagaca | tgcctgagga | tctcaagcgc | cgcttggccg | actctgttca | 1260 |
| gcgaacggtc | gggcctgctg | gcttctggga | aagcgacgac | aatgacaata | tggaaacagc | 1320 |
| ttcgcaaaac | ggcaagaaat | atcaatcaag | agatagtgat | ctgctttcaa | accttggttt | 1380 |
| cggtgaggac | gtatacggcg | acgcggtcta | tccaggcgtc | gtcggcaaat | cggcgatcgg | 1440 |
| cgagaccagt | tatcgtggtt | tctaccgggc | ttaccaggca | cacgtcagca | gctccaactg | 1500 |
| ggctgagttc | gagcatgcct | ctagtacttg | gcatactgaa | cttacgaaga | ctactgatcg | 1560 |
| ctaacagacg | agtcgaccat | gatgatcaat | attcaagaag | acaagctggt | ttccgcccac | 1620 |
| gacgccgaag | agattcttcg | tttcttcaat | tgccacgact | ctgctttgca | acaagaagcc | 1680 |
| actacgctgc | tgacccagga | agcgcattg | ttggacattc | aggcttaccg | tgcttggtta | 1740 |
| gagcactgcg | tggggtcaga | ggtgcaatat | caggtcatt | cacgcgaact | gcgcgcagct | 1800 |
| tcagagcgtc | gttataagct | caatgaagcc | atgaacgttt | acaacgaaaa | ttttcagcaa | 1860 |
| ctgaaagttc | gagttgagca | tcaactggat | ccgcaaaact | ggggcaacag | cccgaagctg | 1920 |
| cgctttactc | gctttatcac | caacgtccag | gccgcaatgg | acgtaaatga | caaagagcta | 1980 |
| cttcacatcc | gctccaacgt | cattctgcac | cgggcacgac | gtggcaatca | ggtcgatgtc | 2040 |

```
ttctacgccg cccgggaaga taaatggaaa cgtggcgaag gtggagtacg aaaattggtc      2100
cagcgattcg tcgattaccc agagcgcata cttcagacgc acaatctgat ggtctttctg      2160
tgattcagtg accatttta caaatggtca ctgcaaccgc ggtcaccatt aatcaaaggg       2220
aatgtacgtg tatgggcaat caacaagtcg tttcgataac cggtg                     2265
```

<210> SEQ ID NO 58
<211> LENGTH: 449
<212> TYPE: PRT
<213> ORGANISM: Artificial Sequence
<220> FEATURE:
<223> OTHER INFORMATION: A polypeptide encoded by SEQ ID NO:56.

<400> SEQUENCE: 58

```
Met Asn Tyr Asn Asn Lys Ile Leu Val Ser Glu Ser Gly Leu Ser Gln
 1               5                  10                  15

Lys His Leu Ile His Gly Asp Glu Glu Leu Phe Gln His Glu Leu Lys
            20                  25                  30

Thr Ile Phe Ala Arg Asn Trp Leu Phe Leu Thr His Asp Ser Leu Ile
        35                  40                  45

Pro Ala Pro Gly Asp Tyr Val Thr Ala Lys Met Gly Ile Asp Glu Val
    50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
                85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
    130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Leu Pro Pro Glu Gly Ala Gly Leu
225                 230                 235                 240

Gln Met Thr Ser Lys Tyr Gly Ser Gly Met Gly Val Leu Trp Asp Gly
                245                 250                 255

Tyr Ser Gly Val His Ser Ala Asp Leu Val Pro Glu Leu Met Ala Phe
            260                 265                 270

Gly Gly Ala Lys Gln Glu Arg Leu Asn Lys Glu Ile Gly Asp Val Arg
        275                 280                 285

Ala Arg Ile Tyr Arg Ser His Leu Asn Cys Thr Val Phe Pro Asn Asn
    290                 295                 300

Ser Met Leu Thr Cys Ser Gly Val Phe Lys Val Trp Asn Pro Ile Asp
305                 310                 315                 320

Ala Asn Thr Thr Glu Val Trp Thr Tyr Ala Ile Val Glu Lys Asp Met
```

```
                 325                 330                 335
Pro Glu Asp Leu Lys Arg Arg Leu Ala Asp Ser Val Gln Arg Thr Trp
            340                 345                 350

Gly Pro Ala Gly Phe Trp Glu Ser Asp Asn Asp Asn Met Glu Thr
            355                 360                 365

Ala Ser Gln Asn Gly Lys Lys Tyr Gln Ser Arg Asp Ser Asp Leu Leu
        370                 375                 380

Ser Asn Leu Gly Phe Gly Glu Asp Val Tyr Gly Asp Ala Val Tyr Pro
385                 390                 395                 400

Gly Val Val Gly Lys Ser Ala Ile Gly Glu Thr Ser Tyr Arg Gly Phe
                405                 410                 415

Tyr Arg Ala Tyr Gln Ala His Val Ser Ser Ser Asn Trp Ala Glu Phe
            420                 425                 430

Glu His Ala Ser Ser Thr Trp His Thr Glu Leu Thr Lys Thr Thr Asp
        435                 440                 445

Arg
```

<210> SEQ ID NO 59
<211> LENGTH: 449
<212> TYPE: PRT
<213> ORGANISM: Artificial Sequence
<220> FEATURE:
<223> OTHER INFORMATION: A polypeptide encoded by SEQ ID NO:57.

<400> SEQUENCE: 59

```
Met Asn Tyr Asn Asn Lys Ile Leu Val Ser Glu Ser Gly Leu Ser Gln
1               5                   10                  15

Lys His Leu Ile His Gly Asp Glu Glu Leu Phe Gln His Glu Leu Lys
            20                  25                  30

Thr Ile Phe Ala Arg Asn Trp Leu Phe Leu Thr His Asp Ser Leu Ile
        35                  40                  45

Pro Ala Pro Gly Asp Tyr Val Thr Ala Lys Met Gly Ile Asp Glu Val
    50                  55                  60

Ile Val Ser Arg Gln Asn Asp Gly Ser Ile Arg Ala Phe Leu Asn Val
65                  70                  75                  80

Cys Arg His Arg Gly Lys Thr Leu Val Ser Val Glu Ala Gly Asn Ala
                85                  90                  95

Lys Gly Phe Val Cys Ser Tyr His Gly Trp Gly Phe Gly Ser Asn Gly
            100                 105                 110

Glu Leu Gln Ser Val Pro Phe Glu Lys Asp Leu Tyr Gly Glu Ser Leu
        115                 120                 125

Asn Lys Lys Cys Leu Gly Leu Lys Glu Val Ala Arg Val Glu Ser Phe
    130                 135                 140

His Gly Phe Ile Tyr Gly Cys Phe Asp Gln Glu Ala Pro Pro Leu Met
145                 150                 155                 160

Asp Tyr Leu Gly Asp Ala Ala Trp Tyr Leu Glu Pro Met Phe Lys His
                165                 170                 175

Ser Gly Gly Leu Glu Leu Val Gly Pro Pro Gly Lys Val Val Ile Lys
            180                 185                 190

Ala Asn Trp Lys Ala Pro Ala Glu Asn Phe Val Gly Asp Ala Tyr His
        195                 200                 205

Val Gly Trp Thr His Ala Ser Ser Leu Arg Ser Gly Glu Ser Ile Phe
    210                 215                 220

Ser Ser Leu Ala Gly Asn Ala Ala Leu Pro Pro Glu Gly Ala Gly Leu
225                 230                 235                 240
```

-continued

```
Gln Met Thr Ser Lys Tyr Gly Ser Gly Met Gly Val Leu Trp Asp Gly
            245                 250                 255
Tyr Ser Gly Val His Ser Ala Asp Leu Val Pro Glu Leu Met Ala Phe
        260                 265                 270
Gly Gly Ala Lys Gln Glu Arg Leu Asn Lys Glu Ile Gly Asp Val Arg
    275                 280                 285
Ala Arg Ile Tyr Arg Ser His Leu Asn Cys Thr Val Phe Pro Asn Asn
290                 295                 300
Ser Met Leu Thr Cys Ser Gly Val Phe Lys Val Trp Asn Pro Ile Asp
305                 310                 315                 320
Ala Asn Thr Thr Glu Val Trp Thr Tyr Ala Ile Val Glu Lys Asp Met
            325                 330                 335
Pro Glu Asp Leu Lys Arg Arg Leu Ala Asp Ser Val Gln Arg Thr Tyr
            340                 345                 350
Gly Pro Ala Gly Phe Trp Glu Ser Asp Asp Asn Asp Asn Met Glu Thr
        355                 360                 365
Ala Ser Gln Asn Gly Lys Lys Tyr Gln Ser Arg Asp Ser Asp Leu Leu
    370                 375                 380
Ser Asn Leu Gly Phe Gly Glu Asp Val Tyr Gly Asp Ala Val Tyr Pro
385                 390                 395                 400
Gly Val Val Gly Lys Ser Ala Ile Gly Glu Thr Ser Tyr Arg Gly Phe
            405                 410                 415
Tyr Arg Ala Tyr Gln Ala His Val Ser Ser Ser Asn Trp Ala Glu Phe
            420                 425                 430
Glu His Ala Ser Ser Thr Trp His Thr Glu Leu Thr Lys Thr Thr Asp
        435                 440                 445
Arg
```

<210> SEQ ID NO 60
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 60
gttcagcgaa cgggcgggcc tgctgg                                    26

<210> SEQ ID NO 61
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 61
gttcagcgaa cggccgggcc tgctgg                                    26

<210> SEQ ID NO 62
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 62
gttcagcgaa cgaccgggcc tgctgg                                    26

-continued

```
<210> SEQ ID NO 63
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 63
gttcagcgaa cgatcgggcc tgctgg                                    26

<210> SEQ ID NO 64
<211> LENGTH: 26
<212> TYPE: DNA
<213> ORGANISM: Artificial Sequence
<220> FEATURE:
<223> OTHER INFORMATION: A mutagenic oligonucleotide.

<400> SEQUENCE: 64
gttcagcgaa cgtgggggcc tgctgg                                    26

<210> SEQ ID NO 65
<211> LENGTH: 25
<212> TYPE: DNA
<213> ORGANISM: Artificial Sequence
<220> FEATURE:
<223> OTHER INFORMATION: A mutagenic oligonucleotide.

<400> SEQUENCE: 65
ttcagcgaac gtacgggcct gctgg                                     25
```

MODIFIED NAPHTHALENE DIOXYGENASES AND METHODS OF USE

CROSS-REFERENCE TO RELATED APPLICATIONS

This application is a continuation of International Patent Application No. PCT/US99/25079, filed Oct. 26, 1999 which in turn claims priority to U.S. Provisional Application No. 60/105,575, filed Oct. 26, 1998.

GOVERNMENT FUNDING

The invention described herein was made with U.S. Government support under United States Public Health Service grant number R01 GM29909 awarded by the National Institute of General Medical Sciences. The United States Government has certain rights in the invention.

BACKGROUND OF THE INVENTION

Interest in the substrate specificity of bacterial dioxygenases stems from initial studies on the degradation of benzene and toluene more than 25 years ago. A mutant strain of *Pseudomonas putida* (strain F39/D) was shown to oxidize benzene and toluene to cis-1,2-dihydroxycyclohexa-3,5-diene (cis-benzene dihydrodiol) and cis-(1S, 2R)-dihydroxy-3-methylcyclohexa-3,5-diene (cis-toluene dihydrodiol), respectively (D. T. Gibson, et al., *Biochemistry*, 1970, 9, 1631–1635; D. T. Gibson, et al., *Biochemistry*, 1970, 9, 1626–1630; and V. M. Kobal et al., *J. Am. Chem. Soc.*, 1973, 95, 4420–4421).

The enzyme catalyzing these reactions, toluene dioxygenase (TDO), is capable of producing enantiomerically pure cyclohexadiene cis-diols from a wide range of aromatic substrates. D. T. Gibson, et al., *Microbial Degradation of Organic Compounds* (Gibson, D. T., ed.), pp. 181–251, Marcel Dekker, New York, N.Y. (1984); D. T. Gibson, et al., *Pseudomonas: biotransformations, pathogenesis, and evolving biotechnology*, (Silver, S. et al., ed.), pp. 121–132, American Society for Microbiology, Washington D.C. (1990); G. N. Sheldrake, *Chirality in Industry: the Commercial Manufacture and Application of Optically Active Compounds* (Collins, A. N. et al., eds.), pp. 127–166, John Wiley & Sons, Chichester, UK (1992); Stabile, M. R., Ph.D. thesis. Virginia Polytechnic Institute and State University, Blacksburg, Va. (1995); and D. R. Boyde and G. N. Sheldrake, *Nat. Prod. Rep.* 1988, 15, 309–324.

In contrast to the body of work relating to TDO, relatively little attention has been paid to the related enzyme naphthalene dioxygenase. Cells of Pseudomonas sp NCIB 9816-4 contain an inducible multi-component enzyme system designated NDO, which initiates naphthalene catabolism by catalyzing the addition of both atoms of molecular oxygen and two hydrogen atoms to the substrate to yield enantiomerically pure (+)-cis-(1R,2S)-dihydroxy-1,2-dihydronaphthalene (D. M. Jerina et al. *Arch. Biochem. Biophys.* 1971, 142, 394–396). NDO has a relaxed substrate specificity and catalyzes the deoxygenation of many related 2- and 3-ring aromatic and hydroaromatic (benzocyclic) compounds to their respective cis-diols.

The potential of NDO to form products of opposite chirality to those formed by TDO was first noted in 1988 during studies on the oxidation of indan. The major product formed by TDO was (−)-(1R)-indanol (84% enantiomeric excess [ee]) whereas NDO produced (+)-(1S)-indanol (>92% ee) (L. P. Wackett et al., *Biochemistry*, 1988, 27, 1360–1367. Subsequent studies with NDO revealed further differences in substrate specificity and suggested that this enzyme is an additional source of chiral intermediates and synthons for the enantiospecific synthesis of biologically active products. S. M. Resnick et al. *Journal of Industrial Microbiology*, 1996, 17, 438–457.

NDO belongs to a family of bacterial enzymes that have an essential role in the recycling of carbon in nature. These enzymes are especially important in the degradation of aromatic hydrocarbons and related environmental pollutants. Knowledge of the NDO reaction mechanism is thus important in the development of bioremediation strategies for cleaning up environments contaminated with hazardous aromatic compounds. An attractive alternative to bioremediation is the application of 'green chemistry,' which refers to the production of industrial chemicals by processes that do not generate hazardous waste. For example, a recombinant strain of *Escherichia coli* expressing NDO, has been used to synthesize indigo dye from glucose. cis-Arene diols produced by NDO and toluene dioxygenase have been used in the synthesis of many products of biological and economic importance.

Knowledge of the types of reactions catalyzed by NDO and the range of substrates oxidized by NDO is based largely on biotransformation studies with cis-naphthalene dihydrodiol dehydrogenase (DDH) mutants, recombinant strains expressing NDO and purified NDO components. Pseudomonas sp 9816/11 is a DDH mutant of strain 9816-4 (G. M. Klecka and G. T. Gibson, *Biochem J.*, 1979, 180, 639–645) which accumulates cis-naphthalene-1,2-dihydrodiol when induced cells are incubated with naphthalene and a suitable carbon source (D. S. Torok, *J. Bacteriol.* 1995, 177, 5799–5805. Studies with purified dioxygenase components have been crucial in the identification of reactions catalyzed by NDO in the absence of other host-associated enzyme activities which, through subsequent catalysis, have the potential to affect product distribution and/or stereochemistry.

In addition to cis-dihydroxylation, NDO also catalyzes a variety of other oxidations which include monohydroxylation, desaturation (dehydrogenation), O- and N-dealkylation and sulfoxidation reactions. S. M. Resnick et al. *Journal of Industrial Microbiology*, 1996, 17, 438–457. Many of the reactions catalyzed by NDO and other microbial dioxygenases yield hydroxylated compounds that can serve as chiral intermediates or chiral synthons for a variety of compounds of interest to pharmaceutical and specialty chemical industries.

Despite the wide range of useful oxygenated materials that can be prepared with TDO and NDO, there is currently a need for additional oxygenated chiral synthons that can be used to prepare therapeutically useful compounds, or useful intermediates. In particular, there is a need for additional chiral synthons that differ from the TDO and NDO products by absolute configuration or by the site of oxygenation. There is also a need for new methods to prepare hydroxylated aryl compounds for use in the polymer, resin, pharmaceutical or rubber industry, which generate less industrial waste than currently available methods. Further, there is a need for novel enzymes possessing structures, stabilities, or reactivities that differ from the native enzymes.

SUMMARY OF THE INVENTION

The crystal structure of NDO has recently been published by B. Kauppi et al. *Structure*, 1998, 6, no. 5, 571–586. Based on this structure, the amino acid at position 352 is located at the active site of NDO. As described hereinbelow, site-directed mutagenesis was used to construct DNA molecules that encode NDO mutants having amino acid substitutions at position 352. Changing the amino acid at position 352 from phenylalanine to valine provided an enzyme (SEQ ID NO:2, encoded by SEQ ID NO:1) that gives a change in the preferred absolute configuration of the 1,2-dihydroxy-1,2-dihydronaphthalene formed from naphthalene. This enzyme also gave a change in the regioselectivity of the products obtained from oxidation of biphenyl and phenanthrene.

Accordingly, the invention provides an NDO or NDO related complex comprising a plurality of polypeptides, wherein the complex comprises at least one alpha-subunit polypeptide that comprises: 1) a substituted amino acid (e.g. valine or leucine) at the position corresponding to position 352 in NDO, 2) a substituted amino acid at the position corresponding to position 201, 202, 260, 316, 351, 358, 362, or 366 in NDO, or 3) a substituted amino acid at the position corresponding to position 352 in NDO, and a substituted amino acid at the position corresponding to position 201, 202, 260, 316, 351, 358, 362, or 366 in NDO; or a catalytically active fragment thereof. The complexs of the invention can preferably be isolated and purified.

The invention also provides an isolated and purified polypeptide having Swiss-prot data base Accession Number P23094 that comprises an amino acid other than phenylalanine at position 352, or a catalytically active variant, or a catalytically active fragment thereof. Preferably, the amino acid at position 352 is a naturally occurring amino acid. More preferably, the polypeptide is SEQ ID NO:2, 32, 33, 34, 35, or 36.

The invention also provides an isolated and purified NDO related polypeptide wherein the amino acid at the position corresponding to position 352 in NDO has been replaced with another amino acid, or a catalytically active fragment or catalytically active variant thereof. Preferably, the amino acid at the position corresponding to position 352 in NDO is a naturally occurring amino acid. More preferably, the amino acid at the position corresponding to position 352 in NDO is valine.

Site-directed mutagenesis was also used to construct DNA molecules that encode NDO mutants having an amino acid substitution at position 201, 202, 260, 316,351, 352, 358, 362, or 366. Accordingly, the invention provides an isolated and purified NDO wherein the amino acid at position 201, 202, 260, 316, 351, 352, 358, 362, or 366 has been replaced with another amino acid, or a catalytically active variant, or a catalytically active fragment thereof.

Changing the amino acid at position 352 in NDO from phenylalanine to valine provided an enzyme (SEQ ID NO:2, encoded by SEQ ID NO:1) that gives a change in the preferred absolute configuration of the 1,2-dihydroxy-1,2-dihydronaphthalene formed from naphthalene. This enzyme also gave a change in the regioselectivity of the products obtained from oxidation of biphenyl and phenanthrene The invention also provides an isolated and purified DNA segment encoding a polypeptide of the invention, or a variant or fragment thereof.

The invention also provides a primer or probe having about 80% nucleic acid sequence identity with a DNA segment encoding a polypeptide of the invention, or a variant or fragment thereof.

The invention also provides an expression cassette comprising a promotor operably linked to a DNA segment encoding a polypeptide of the invention or a variant or fragment thereof.

The invention also provides a host cell, the genome of which is augmented by a DNA segment encoding a polypeptide of the invention, or a catalytically active variant or fragment thereof.

The invention also provides a method to produce a catalytically active polypeptide comprising culturing a host cell transformed with a DNA segment encoding a polypeptide of the invention, or a catalytically active variant or fragment thereof, so that the host cell expresses the polypeptide, variant or fragment.

The invention also provides a method for preparing cis-naphthalene dihydrodiol (e.g. (−)-(1S,2R)-cis-naphthalene dihydrodiol) comprising contacting naphthalene with a polypeptide of the invention, or a catalytically active variant or fragment thereof.

The invention also provides a method for preparing cis-naphthalene dihydrodiol (e.g. (−)-(1S,2R)-cis-naphthalene dihydrodiol) comprising contacting a host cell of the invention with naphthalene.

The invention also provides a method for preparing cis-biphenyl-3,4-dihydrodiol (e.g. (−) or (+) cis-biphenyl-3, 4-dihydrodiol) comprising contacting biphenyl with a polypeptide of the invention, or a catalytically active variant or fragment thereof. The method may optionally further comprise dehydrating the cis-biphenyl-3,4-dihydrodiol to give 4-hydroxybiphenyl.

The invention also provides a method for preparing cis-biphenyl-3,4-dihydrodiol (e.g. (−)-cis-biphenyl-3,4-dihydrodiol) comprising contacting a host cell of the invention with biphenyl. The method may optionally further comprise dehydrating the (−)-cis-biphenyl-3,4-dihydrodiol to give 4-hydroxybiphenyl.

The invention also provides a method for preparing cis-phenanthrene-1,2-dihydrodiol (e.g. cis-(1S,2R)-phenanthrene-1,2-dihydrodiol) comprising contacting phenanthrene with a polypeptide of the invention, or a catalytically active variant or fragment thereof.

The invention also provides a method for preparing cis-phenanthrene-1,2-dihydrodiol (e.g. cis-(1S,2R)-phenanthrene-1,2-dihydrodiol) comprising contacting a host cell of the invention with phenanthrene.

The invention also provides a method to oxidize an aromatic compound to a corresponding dihydrodihydroxy compound comprising contacting the aromatic compound with a polypeptide of the invention, or a catalytically active variant or fragment thereof.

The invention also provides a method to oxidize an aromatic compound to a corresponding dihydrodihydroxy compound comprising contacting the aromatic compound with a host cell of the invention.

The invention also provides a method to prepare an optically active cis-cyclohexadiene of formula (I):

(I)

wherein one of $R_1$ and $R_2$ is hydrogen and the other is phenyl, 2-phenylvinyl, 2-phenylethynyl, or vinyl, wherein any phenyl ring may optionally be substituted with 1, 2, or 3 substituents independently selected from the group consisting of hydroxy, halo, carboxy, cyano, nitro, trifluoromethyl, amino, $(C_1-C_6)$alkyl, $(C_1-C_6)$ alkoxycarbonyl, and $(C_1-C_6)$alkoxy, comprising contacting a corresponding compound of formula (II):

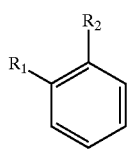

(II)

with a polypeptide of the invention, or a catalytically active variant or fragment thereof, or with a host cell of the invention. Preferably, $R_1$ is phenyl or 4-hydroxyphenyl. The method may optionally comprise dehydrating the resulting compound of formula I.

The invention also provides a method to prepare cis-1,2-dihydroxyindan comprising contacting indene with a polypeptide of the invention, or a catalytically active variant or fragment thereof, or with a host cell of the invention.

The invention also provides a method to prepare 1,2-dihydroxy-1,2,3,4-tetrahydronaphthalene comprising contacting 1,2-dihydronaphthalene with a polypeptide of the invention, or a catalytically active variant or fragment thereof, or with a host cell of the invention.

The invention also provides a method to prepare 1,2-dihydroxy-1,2-dihydrophenanthrene or 3,4-dihydroxy-3,4-dihydrophenanthrene comprising contacting phenanthrene with a polypeptide of the invention, or a catalytically active variant or fragment thereof, or with a host cell of the invention.

The invention also provides novel compounds and intermediates disclosed herein, as well as crystallized forms of the polypeptides disclosed herein. Preferably, the invention provides a crystallized form of SEQ ID NO:26.

Polypeptides of the invention provide a biosynthetic route to the either enantiomer of cis-naphthalene dihydrodiol, to either enantiomer of cis-biphenyl-3,4-dihydrodiol, and to either enantiomer of cis-phenanthrene-1,2-dihydrodiol. These products can be used in the synthesis of new polymers and pharmaceutical products. For example, arene cis-diols are useful starting materials for stereospecific organic synthesis (S. M. Brown, et al., *Organic Synthesis: Theory and Applications* (Hudlicky, T., ed.), pp. 113–176, JAI Press, Greenwich, Conn. (1993); and T. Hudlicky and J. W. Reed, *Adv. Asymm. Synth.* 1995, 1, 271–312). They can undergo a variety of reactions including asymmetric Diels-Alder reactions, epoxidation, photochemical oxygenation, metallation, diol cleavage, diene cleavage, carbene additions and ozonolysis. They have been used to prepare a variety of synthetic products that are not readily obtainable by conventional chemical synthesis. Examples include conduritols, inositol phosphates, pinitol enantiomers, prostanoid and terpene synthons, and complex natural products such as (–)-zeylena and (+)-lycoricidine.

DETAILED DESCRIPTION

Figure 1:
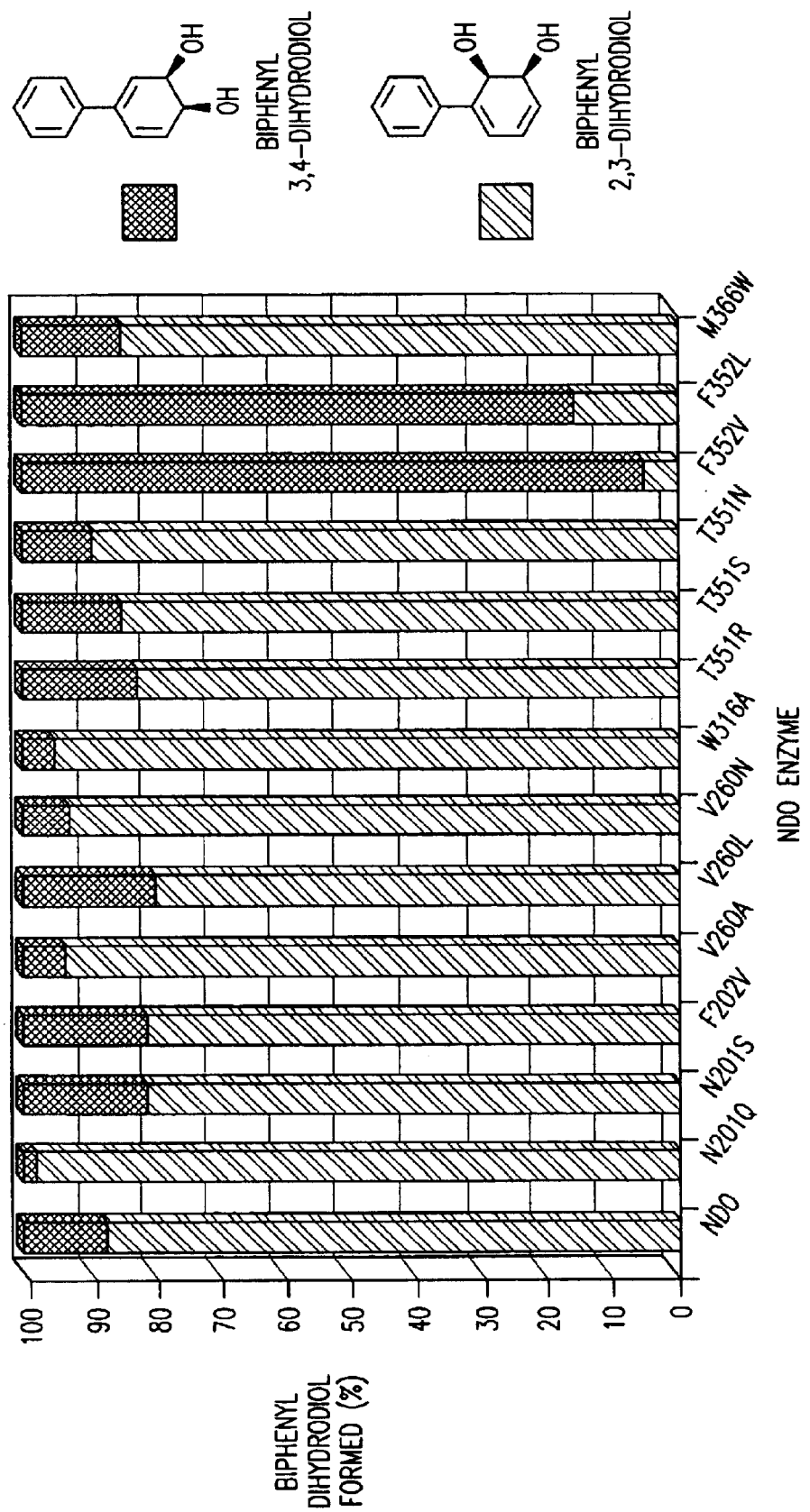
FIG. 1 illustrates the effect of specific amino acid substitutions in an alpha-subunit having SEQ ID NO: 26 on the regiospecificity of a naphthalene dioxygenase during the oxidation of biphenyl.

The following definitions are used, unless otherwise described: halo is fluoro, chloro, bromo, or iodo. Alkyl, alkoxy, denote both straight and branched groups; but reference to an individual radical such as "propyl" embraces only the straight chain radical, a branched chain isomer such as "isopropyl" being specifically referred to.

The term "amino acid," comprises the residues of the natural occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine).

As used herein, the terms "isolated and/or purified" refer to in vitro preparation, isolation and/or purification of a nucleic acid molecule, sequence or segment of the invention, so that it is not associated with in vivo substances. Thus, with respect to an "isolated nucleic acid molecule sequence or segment", which includes a polynucleotide of DNA or RNA or of synthetic origin or some combination thereof, the "isolated nucleic acid molecule sequence or segment" (1) is not associated with all or a portion of a polynucleotide in which the "isolated nucleic acid molecule" is found in nature, (2) can be operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes or primers; although oligonucleotides may be double stranded, e.g., for use in the construction of a variant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phophoroselenoate, phosphorodiselenoate, phosphoroanilothioate, phosphoraniladate, phosphoroamidate, and the like. An oligonucleotide can include a label for detection, if desired.

The term "isolated polypeptide" means a polypeptide encoded by DNA or RNA, including polypeptides that are synthetic in origin, or some combination thereof, which isolated polypeptide (1) is not associated with proteins found in nature, (2) is free of other proteins from the same source, (3) is expressed by a cell from a different species, or (4) does not occur in nature.

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence identity between the polynucleotides, oligonucleotides, variants, and fragments of the invention and a nucleic acid sequence of interest is at least about 65%, and more typically with preferably increasing identities of at least about 70%, about 90%, about 95%, about 98%, and 100%. See Sambrook et al. Molecular Cloning: A Laboratory Manual, Cold Spring Harbor (1989).

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "NDO related polypeptide (or complex)" means a polypeptide (or complex) that belongs to the same family of bacterial enzymes as NDO or TDO. Preferably, an NDO related polypeptide has substantial identity with NDO. More preferably, an NDO related polypeptide is encoded by the DNA sequence having Genbank Accession number M60405, M23914, AF010471, AF004284, M83949, AF004283, AB004059, D84146, AF036940, U49504, or U62430.

The term "catalytically active," when applied to a polypeptide or a polypeptide variant or fragment of the invention, means that the variant or fragment catalyzes one or more of the reactions catalyzed by NDO or an NDO related polypeptide (see for example S. M. Resnick, et al., *Journal of Industrial Microbiology*, 1996, 17, 438–457). Preferably, a catalytically active polypeptide, or a catalytically active variant, or fragment catalyzes one or more of the reactions catalyzed by NDO. More preferably, a catalytically active polypeptide, or a catalytically active variant, or fragment catalyzes the oxidation of an aromatic substrate to give the corresponding dihydrodihydroxy compound (e.g. the oxidation of biphenyl or phenanthrene to 3,4-dihydroxy-3, 4dihydrobiphenyl or 1,2-dihydroxy-1,2-dihydrophenanthrene, respectively).

The term "biologically active" with respect to a fragment or variant of a polypeptide means that the fragment or variant has at least about 10%, preferably at least about 50%, and most preferably at least about 90%, the activity of the reference polypeptide. The activity of a polypeptide of the invention can be measured by methods well known to the art including, but not limited to, the ability of the peptide to elicit a sequence-specific immunologic response when the peptide is administered to an organism, e.g., chicken, goat, sheep or mice. The invention also provides polypeptides, as well as fragments and variants thereof, that are useful to elicit a sequence-specific immunologic response when the peptide is administered to an organism (e.g. a mammal).

When applied to a polypeptide the term "fragment" means a portion of the reference polypeptide that comprises the amino acid that corresponds to amino acid 352 in SEQ ID NO:26. Preferably the portion of the reference polypeptide also comprises at least about 10, 50, or 500 additional amino acids of the reference peptide. More preferably, the portion of the reference polypeptide comprises at least about 1000 or 1500 additional amino acids or the reference peptide.

When applied to a nucleotide sequence the term "fragment" means a portion of the reference nucleotide sequence that 1) encodes the amino acid corresponding to amino acid 352 in SEQ ID NO:26, and 2) encodes a catalytically active polypeptide. Preferably the portion of the reference nucleotide sequence also comprises at least about 30, 60, 150, or 300, nucleoside bases of the reference nucleotide sequence. More preferably, the portion of the reference nucleotide sequence also comprises at least about 600, 900, or 1200 nucleoside bases of the reference nucleotide sequence.

The following terms are used to describe the sequence relationships between two or more polynucleotides: "reference sequence", "comparison window", "sequence identity", "percentage of sequence identity", and "substantial identity".

A "reference sequence" is a defined sequence used as a basis for a sequence comparison; a reference sequence may be a subset of a larger sequence, for example, as a segment of a full-length DNA or gene sequence given in a sequence listing, or may comprise a complete DNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. "Percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least about 85 percent sequence identity, preferably at least about 90 to about 95 percent sequence identity, more usually at least about 99 percent sequence identity as compared to a reference sequence over a comparison window of at least 20 nucleotide positions, frequently over a window of at least 20–50 or 50–200 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80 percent sequence identity, preferably at least about 80 percent sequence identity, more preferably at least about 90 percent sequence identity, and most preferably at least about 99 percent sequence identity. Alternatively two polypeptide sequences have substantial identity if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. Preferably, the two sequences-have substantial identity if their amino acids are greater than or equal to 50% identical when optimally aligned using the ALIGN program. When a percent sequence identity is given, it means that the stated percentage of the amino acids are identical when the two sequences are aligned for maximum matching. Gaps (in either of the two sequences being matched) are allowed in maximizing matching; gap lengths of 5 or less are preferred with 2 or less being more preferred.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

When applied to a polypeptide the term "variant," means a polypeptide that 1) has substantial identity with but is not identical to the reference polypeptide; and 2) is identical to the reference polypeptide at the position corresponding to amino acid 352 in SEQ ID NO:26.

When applied to a nucleotide sequence, the term "variant" means a nucleotide sequence that 1) has substantial identity with but is not identical to the reference sequence; and 2) encodes the same amino acid as the reference sequence at the position encoded by the reference sequence that corresponds to amino acid 352 in SEQ ID NO:26.

The variant DNA molecules of the invention may include DNA molecules with "silent" substitutions. For example, a preferred embodiment of the invention is an isolated and purified DNA molecule comprising a preselected DNA segment encoding SEQ ID NO:2, wherein the DNA segment comprises SEQ ID NO:1, or variants of SEQ ID NO:1, having nucleotide substitutions which are "silent" (see Table 1). That is, when silent nucleotide substitutions are present in a codon, the same amino acid is encoded by the codon with the nucleotide substitution as is encoded by the codon without the substitution. "Silent" nucleotide substitutions in SEQ ID NO:1 which can encode a peptide having SEQ ID NO:2 can be ascertained by reference to Table 1 and page D1 in Appendix D in Sambrook et al., *Molecular Cloning: A Laboratory Manual* (1989). Nucleotide substitutions can be introduced into DNA segments by methods well known to the art. See, for example, Sambrook et al., supra.

TABLE 1

| Amino Acid | Codon |
| --- | --- |
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; and $(C_1-C_6)$alkoxy can be methoxy, ethoxy, propoxy, isopropoxy, butoxy, iso-butoxy, sec-butoxy, pentoxy, 3-pentoxy, or hexyloxy.

Pseudomonas sp NCIB 9816-4 contain an inducible multicomponent enzyme system designated naphthalene dioxygenase (NDO) which catalyzes the formation of cis-naphthalene dihydrodiol. The system consists of an iron-sulfur flavoprotein (reductase$_{NAP}$), a Rieske [2Fe-2S] protein (ferredoxin$_{NAP}$), and an iron-sulfur protein (ISP$_{NAP}$), which serves as the terminal oxygenase component. ISP$_{NAP}$ has an $\alpha_3\beta_3$ subunit component and each α subunit contains a Rieske [2Fe-2S] cluster and mononuclear iron. The Rieske cluster is believed to be an electron storage center that transfers electrons to mononuclear iron which is responsible for dioxygen activation and ultimately the catalytic reaction.

The genes encoding the NDO complex in Pseudomonas sp NCIB 9816-4 have been cloned and expressed in *Escherichia coli* (W-C Suen and D. T. Gibson, *Gene*, 1994, 143, 67–71; and W-C Suen Ph.D. Thesis The University of Iowa, Iowa City, Iowa, 1993). The nucleotide sequences of the genes encoding reductase$_{NAP}$ (nahAa), ferredoxin$_{NAP}$ (nahAb), and ISP$_{NAP}$ (nahAcAd) have been determined and show 93.3%, 93.3%, 96.9%, and 94.8% identity, respectively, at the predicted amino acid level with the isofunctional genes carried by the well-studied NAH7 plasmid in *P. putida* G7 (S. Kurkele, *Gene*, 1988, 73, 355–362; M. J. Simon, *Gene*, 1993, 127, 31–37).

A number of dioxygenases with a structure similar to NDO have been identified. For example, the dioxygenases shown in Table 2 have α subunits with greater than 80% amino acid identity to naphthalene dioxygenase from Pseudomonas sp. strain NCIB 9816-4 (calculated using GAP Wisconsin Genetics Software Package, Genetics Computer Group, 575 Science Dr., Madison, Wis.). Because of their similarity to NDO in structure and function, it is reasonable to believe that modifying these polypeptides by replacing the amino acid corresponding to F352 in NDO with valine, will provide novel polypeptides that have similar advantageous properties compared to the native polypeptides. Accordingly, the invention also provides the following DNA molecules (SEQ ID No.'s 3–13) that have been modified to encode valine at the position corresponding to the F352 amino acid in NDO, as shown in Table 2.

TABLE 2

| Genbank Accession Number | Amino Acid Corresponding to F352 in NDO | SEQ ID NO. For Modified DNA Sequence | SEQ ID NO. For Corresponding Polypeptide |
| --- | --- | --- | --- |
| M60405 | F352 | SEQ ID NO:3 | SEQ ID NO:14 |
| M23914 | F352 | SEQ ID NO:4 | SEQ ID NO:15 |
| AF010471 | F352 | SEQ ID NO:5 | SEQ ID NO:16 |
| AF004284 | F352 | SEQ ID NO:6 | SEQ ID NO:17 |
| M83949 | F352 | SEQ ID NO:7 | SEQ ID NO:18 |
| AF004283 | F352 | SEQ ID NO:8 | SEQ ID NO:19 |
| AB004059 | F352 | SEQ ID NO:9 | SEQ ID NO:20 |
| D84146 | F352 | SEQ ID NO:10 | SEQ ID NO:21 |
| AF036940 | F350 | SEQ ID NO:11 | SEQ ID NO:22 |
| U49504 | I350 | SEQ ID NO:12 | SEQ ID NO:23 |
| U62430 | T355 | SEQ ID NO:13 | SEQ ID NO:24 |

The invention also provides the polypeptides (SEQ ID No.'s 14–24) that are encoded by the DNA molecules of SEQ ID No.'s 3–13. The invention also provides a host cell, the genome of which is augmented by a DNA molecule having SEQ ID NO:3–13.

In addition to the enantiospecific cis-dihydroxylation of naphthalene, NDO catalyzes dioxygenation of a variety of multicyclic and heterocyclic aromatic compounds to produce, in many cases, chiral cis-dihydrodiols. The mutant and-recombinant strains expressing polypeptides of the invention allow the synthesis of cis-diols in high yields and/or high enantiomeric purity. For example, substrates which are oxidized to cis-dihydrodiols by NDO include indene, 1,2-dihydronaphthalene, benzocyclohept-1-ene, anthracene, phenanthrene, dibenzo[1,4]dioxan, acenaphthylene, 1- and 2-substituted naphthalenes, biphenyl, fluorene, dibenzofuran, dibenzothiophene, 9,10-dihydroanthracene, and 9,10-dihydrophenanthrene.

The DNA segment having Genbank Accession Number U49496 is SEQ ID NO:25. The polypeptide having Swissprot data base Accession Number P23094 is SEQ ID NO:26.

The invention will now be illustrated by the following non-limiting Examples.

EXAMPLES

Example 1

Construction of Site-Directed Mutations

*Escherichia coli* strains DH5α (Life Technologies, Gaithersburg, Md.) and JM109(DE3)) (Promega Corp., Madison, Wis.) were used for subcloning and gene expression experiments, respectively. Competent *E. coli* strains ES 1301 and JM109 were purchased from Promega Corp. and used in the site-directed mutagenesis procedure described below.

*E. coli* strains were grown at 30 or 37° C. in Luria-Bertani (LB) medium (R. W. Davis, et al. Advanced Bacterial Genetics, Cold Spring Harbor Laboratory, Cold Spring Harbor, N.Y., 1980), or Terrific Broth (TB) medium (Lee, S. -Y., and S. Rasheed, *BioTechniques*, 1990, 9, 676–679). To maintain plasmids, ampicillin or tetracycline was added to final concentrations of 150 and 12 μg/ml, respectively. JM109(DE3) strains carrying plasmids of interest were maintained on minimal medium plates (MSB) (R. Y. Stanier, et al., *J. Gen. Microbiol.*, 1966, 43, 159–271) containing 10 mM glucose, 0.1 mM thiamine, and ampicillin. For plates, MSB was solidified with 1.8% Agar Noble (Difco Laboratories, Detroit, Mich.) and LB was solidified with 1.5% Bactoagar (Difco Laboratories).

Mutagenesis of nahAc (encoding the naphthalene dioxygenase α subunit) was carried out with the Altered Sites II in vitro Mutagenesis System according to the manufacturer's instructions (Promega Corp.). A 1.5-kb KpnI-XbaI fragment carrying the 3' half of the nahAc gene and the complete nahAd gene from pDTG141 (Suen, W.-C, Gene expression of naphthalene dioxygenase from Pseudomonas sp. NCIB 9816-4 in *Escherichia coil* Ph.D. thesis. The University of Iowa, Iowa City, Iowa, 1991) was cloned into KpnI-XbaI-digested pALTER-1 (Promega Corp.). The resulting plasmid, designated pMASTER-1, was used as the template for mutagenesis.

The mutagenic oligonucleotide (5'-TTCAGCG AACGGTCGGGCCTGC-3') (SEQ ID NO:37) was designed such that the restriction pattern of the plasmid was altered (eliminating a Psp1406I site shown by underlined bases; T-G base change shown in bold) to facilitate screening for clones carrying the desired mutation. The same T-G base change alters the TTC codon specifying phenylalanine to GTC, which specifies valine.

The phosphorylated oligonucleotide used for mutagenesis was synthesized by Genosys Biotechnologies Inc., Midland, Tex. pMASTER-1 (2 μg) was denatured at room temperature for 5 min in the presence of 200 mM NaOH, 0.2 mM ethylenediamine tetraacetic acid (EDTA) in a 20 μl volume. The denatured plasmid DNA was precipitated by addition of 2 M ammonium acetate (2 μl; pH 4.6) and 100% ethanol (75 μl) and incubated at −70° C. for 30 minutes. After centrifugation for 15 minutes at 14,000 rpm in an Eppendorf centrifuge, the DNA pellet was dried under vacuum and dissolved in 10 mM Tris, 1 mM EDTA (100 ml; pH 8.0).

The primer annealing reaction was carried out with the following components in a final volume of 20 μl: denatured pMASTER-1 (10 μl); tetracycline repair oligonucleotide (1μl; 5'-GCCGGGCCTCTTGCGGGATATCGTCCA-3') (SEQ ID NO:38); ampicillin knockout oligonucleotide (1 μl; 5'-GTTGCCATTGCTGCAG-GCATCGTGGTG-3') (SEQ ID NO:39); phosphorylated mutagenic oligonucleotide 1.25 pmol); 10× annealing buffer (2 μl; 200 mM Tris-HCl, pH 7.5, 100 mM MgCl$_2$, 500 mM NaCl).

The mixture was heated at 75° C. for 5 minutes and cooled slowly (1° C. per min) to 45° C., then more rapidly to room temperature. The synthesis reaction mix contained the products of the annealing reaction and the following: sterile distilled water (5 µl); 10× synthesis buffer (3 pi, 100 mM Tris-HCl (pH 7.5), 5 mM deoxyribonucleotides, 10 mM adenosine triphosphate, 20 mM dithiothreitol); T4 DNA polymerase (1 µl); T4 DNA ligase (1 µl).

The mixture was incubated at 37° C. for 90 minutes. A portion of this mixture (1.5 µl) was used to transform 100 µl of ES 1301mutS competent cells. The transformation mix was incubated on ice for 10 minutes, heated at 42° C. for 45 seconds and then incubated on ice for 2 minutes. LB (900 µl) was added and the culture was incubated at 37° C. for 30 minutes without shaking. After incubation, 500 µl of this culture was diluted with 4.5 ml of LB containing 1.25 µg/µl ampicillin and incubated over night at 37° C. with shaking. Plasmid DNA was purified from the overnight culture as described by Lee, S.-Y., and S. Rasheed, *BioTechniques*, 1990, 9, 676–679, and was used to transform JM109 using standard procedures similar to those described by F. M. Ausubel et al., Current Protocols in Molecular Biology, John Wiley & Sons, Inc., New York, 1993.

The transformation mixture was plated on LB plates containing ampicillin. Colonies were screened for tetracycline sensitivity on LB plates containing 12 µg/ml tetracycline. Plasmid DNA purified from ampicillin resistant, tetracycline sensitive strains was digested with AclI (New England Biolabs, Beverly, Mass.) and the restriction pattern was compared to that of unmutagenized pMASTER-1 using standard molecular biology methods (for example see F. M. Ausubel et al., Current Protocols in Molecular Biology, John Wiley & Sons, Inc., New York, 1993). The nucleotide sequences of both strands of the entire insertion in pMASTER-1 were determined for one mutant plasmid that contained the restriction site change.

Fluorescent automated DNA sequencing was carried out by the University of Iowa DNA Facility using an Applied Biosystems 373A automated DNA sequencer. After verification of each mutation by restriction digestion and sequence analysis, the 1.5-kb KpnI-XbaI fragments carrying each mutation were individually cloned into KpnI-XbaI-digested pDTG141 (which contains the nahAaAbAcAd genes for the naphthalene dioxygenase reductase, ferredoxin and α and β subunits of the oxygenase, respectively. The resulting plasmids were introduced into JM109(DE3) for expression studies. After this subcloning step, the presence of the mutation was verified by restriction analysis and one sequencing run with a primer that generated sequence in the region of the mutagenized base and continued past the KpnI junction.

Example 2

Biotransformations

To produce induced cells for biotransformation studies, JM109(DE3) carrying the plasmid (pDTG141-F352V) [F=phenylalanine; V=valine] was grown in flasks at 30° C. in minimal medium (MSB) (R. Y. Stanier, et al., *J. Gen. Microbiol.*, 1966, 43, 159–271) containing 10 mM glucose, 0.1 mM thiamine, and 150 µg/ml ampicillin with shaking (200 rpm). JM109(DE3)(pDTG141) was grown under identical conditions to provide the wild-type control. Isopropyl-βD-thiogalactopyranoside (IPTG) was added to a final concentration of 100 µM when culture turbidity reached 0.6–0.8 at 660 nm. After a 2.5 hour induction period, biotransformation reactions were initiated. Cultures were spiked with 20 mM glucose, 100 mM phosphate buffer (pH 7.2), and 0.025% (w/v) substrate (e.g. naphthalene, biphenyl, phenanthrene). Cultures were incubated at 30° C. with shaking (250 rpm) for up to 18 hours. Samples were taken periodically and cells were removed by centrifugation.

Culture supernatants were extracted with sodium hydroxide-washed ethyl acetate and analyzed by thin layer chromatography (S. M. Resnick, et al., *FEMS Microbiol. Lett.*, 1993, 113, 297–302). All extracts were analyzed by gas chromatography-mass spectrometry (GC-MS) as previously described (S. M. Resnick, S. *Appl. Environ. Microbiol.*, 1994, 60, 3323–3328). In some cases, dihydrodiol products were derivatized with approximately equimolar amounts of phenyl boronic acid at room temperature prior to injection onto the GC column.

Generally, biotransformation products were most easily detected by thin-layer chromatography (TLC), high-performance liquid chromatography (HPLC), and/or gas chromatography-mass spectrometry (GC/MS). Preparative TLC, HPLC, column or radial dispersion chromatography are commonly used for the isolation of oxidation products prior to nuclear magnetic resonance (NMR) structural determination and/or stereochemical analysis.

Results from the biotransformation studies are shown in Table 3.

TABLE 3

| NDO Polypeptide | Enantiomeric Composition of cis-naphthalene 1,2-dihydrodiol product | Dihydrodiols From Biphenyl | | Dihydrodiols From Phenanthrene | |
| --- | --- | --- | --- | --- | --- |
| | | %2,3 | %3,4 | %3,4 | %1,2 |
| Wild Type | >99 | 87.2 | 12.8 | 91.3 | 8.7 |
| 352-valine | 92.4 | 4.4 | 95.6 | 17.0 | 83.0 |

In the biotransformations described above, incubation of biphenyl with host cells carrying the plasmid (pDTG141-F352V) yielded predominantly 3,4-dihydroxy-3,4-dihydrobiphenyl. This is in contrast to results obtained with the wild type cells, which yielded predominantly the 2,3-dihydroxy-2,3-dihydrobiphenyl. Additionally, incubation of phenanthrene with host cells carrying the plasmid (pDTG 141-F352V) yielded predominantly 1,2-dihydroxy-1,2-dihydrophenanthrene, rather than the corresponding 3,4 isomer preferentially formed from the wild type cells.

Thus, the polypeptides of the invention and the host cells of the invention are useful for preparing chiral diols for use in the polymer, resin, pharmaceutical or rubber industry. In particular, the polypeptides of the invention and the host cells of the invention are useful for preparing (−)-cis-3,4-dihydroxy-3,4-dihydrobiphenyl, and a single enantiomer (1S,2R) of cis-1,2-dihydroxy-1,2-dihydrophenanthrene.

The compound (−)-cis-3,4-dihydroxy-3,4-dihydrobiphenyl can be dehydrated to provide 4-hydroxybiphenyl, which is useful for the manufacture of rubber and resins (see The Merck Index (Martha Windholz, ed.), 10 ed., 7187 (p-phenylphenol) Merck & Co. Inc. New Jersey, USA). Thus, the invention also provides an environmentally benign route to this useful compound. Additionally, the polypeptides-of the invention and the host cells of the invention may be useful for carrying out bioremediation.

Example 3

(+)-cis-(1R,2S)-Dihydroxy-1,2-dihydronaphthalene cis-Dihydroxy-1,2-dihydronaphthalene formed by naphthalene dioxygenase was purified for chiral HPLC analysis by preparative-layer chromatography (A. M. Jeffrey, et al. *Biochemistry*, 1975, 14, 575–583; S. M. Resnick, S. *Appl. Environ. Microbiol.*, 1994, 60, 3323–3328). Chiral stationary-phase liquid chromatography (CSP-HPLC) was used to resolve the two enantiomers of cis-naphthalene dihydrodiol with a Chirocel OJ column (Chiral Technologies, Exton, Pa.) as described by S. M. Resnick, S. *Appl. Environ. Microbiol.*, 1994, 60, 3323–3328. Under these conditions, the (+)-(1R,2S) and (−)-(1S,2R) enantiomers of cis-naphthalene dihydrodiol eluted with retention times of 30 and 33 minutes, respectively.

Example 4

(−)-cis-Biphenyl-3,4-dihydrodiol

A 6 L culture of JM109(DE3)(pDTG141-F352V) was grown in a 10 L Biostat B fermentor (B.Braun Biotech International, Melsungen, Germany) in MSB at 27° C. Automated addition of $NH_4OH$ was used to maintain the pH at 7.3, and a slow glucose feed was used to maintain dissolved $O_2$ concentration at approximately 25% saturation. The culture was induced for 3 hours with 150 µM IPTG when the optical density of the culture (660 nm) reached 0.8. After 17 hours incubation with 0.025% (w/v) biphenyl, cells were harvested by centrifugation and the culture supernatant was extracted with ethyl acetate and concentrated as described previously (S. M. Resnick, et al., *FEMS Microbiol. Lett.*, 1993, 113, 297–302). Two purification methods were employed: 1) multiple elution preparative thin layer chromatography with a 95:5 mixture of chloroform and acetone as eluting solvent as previously described (D. S. Torok, et al., *J. Bacteriol.*, 1995, 177, 5799–5805); and 2) radial dispersion chromatography eluting with a step gradient of chloroform-methanol (S. M. Resnick, S. *Appl. Environ. Microbiol.*, 1994, 60, 3323–3328).

Over 150 mg of biphenyl 3,4-dihydrodiol was obtained from 500 mg crude product. The purity of the compound was determined by thin layer chromatography. The positions of the hydroxyl groups on the aromatic ring were determined by $^1H$ NMR analysis. The enantiomeric purity was determined to be >97% by subjecting the corresponding phenylboronate derivative to gas-chromatography-mass spectrometry analysis (see S. M. Resnick et al., *J. Org. Chem.*, 1995, 60, 3546–3549). Physical properties of the compound were as follows: λmax (in methanol) 276 and 228 nm, $\epsilon_{276}$=4,336±574 and $\epsilon_{228}$=18,580±1621; calculated mass of the phenyl boronate derivative ($C_{18}H_{15}O_2B$) was 274.1165, found mass, 274.1160; $[\alpha]_D$ −37.5±3.8 (c=0.5 g/100 mL, methanol) as determined using a Jasco P1020 polarimeter with a Na 589 nm lamp.

Using a procedure similar to that described in Example 3, cis-biphenyl 2,3-dihydrodiol and cis-biphenyl 3,4-dihydrodiol were separated following multiple elution preparative thin layer chromatography. Under the same chiral HPLC conditions used to separate enantiomers of cis-naphthalene dihydrodiols, the (+)- and (−)-enantiomers of cis-biphenyl 3,4-dihydrodiol eluted with retention times of 31 and 28 minutes, respectively. The (+)-(2R,3S) and (−)-(2S,3R) enantiomers of cis-biphenyl 2,3-dihydrodiol eluted with retention times of 28 and 33 min, respectively.

Example 5

4-Hydroxybiphenyl

Acid-catalyzed dehydration of biphenyl 3,4-dihydrodiol gave predominantly 4-hydroxybiphenyl. The addition of 50 mM HCl (final concentration) to a 0.3 mM solution of biphenyl 3,4-dihydrodiol in methanol at room temperature gave complete dehydration in minutes.

Example 6

Mutations in NDO

Bacterial strains and plasmids. Bacterial strains and plasmids used in this study are listed in Table 4. *Escherichia coli* strains DH5α and JM109(DE3) were used for subcloning and gene expression experiments, respectively. Competent *E. coli* strains ES1301 and JM109 were purchased from Promega Corp., Madison, Wis. and used in the site-directed mutagenesis procedure described below.

Media and growth conditions. *E. coli* strains were grown at 37° C. in Luria-Bertani (LB) medium (12), or Terrific Broth (TB) medium. Antibiotics were added to the following final concentrations as appropriate: ampicillin, 150 µg/ml; tetracycline, 12.5 µg/ml. To produce induced cells for biotransformation studies, JM109(DE3) strains carrying plasmids of interest were grown at room temperature 30° C. in minimal salts medium (MSB) containing 10 mM glucose, 0.1 mM thiamine, and ampicillin. Isopropyl-β-D-thiogalactopyranoside (IPTG) was added to a final concentration of 100 µM when culture turbidity reached 0.6–0.8 at 660 nm. After a 2 hour induction, biotransformations were initiated as described below. For plates, MSB was solidified with 1.8% Noble Agar (Difco Laboratories, Detroit, Mich.) and LB was solidified with 1.5% Bactoagar (Difco Laboratories).

Molecular techniques. Plasmid DNA was isolated as described previously (S-Y Lee, S. Rasheed, *Biotechniques*, 1990, 9, 676–679) or by using the Qiagen Midi Kit (Qiagen, Inc., Chatsworth, Calif.). For nucleotide sequencing, DNA was further purified using a Centricon-100 filter unit (Amicon, Inc., Beverly, Mass.). Restriction digests were performed as suggested by the enzyme suppliers (New England Biolabs, Inc., Beverly, Mass.; Promega Corp., Madison, Wis.). DNA fragments were purified from gel slices using the GeneClean Spin Kit according to the manufacturer's instructions (BIO101, Vista, Calif.). Ligation reactions, transformation of *E. coli* strains and agarose gel electrophoresis were performed by standard procedures.

TABLE 4

Strains and plasmids used in this study

| Strain or plasmid | Relevant Characteristics[a] | Source or Reference |
|---|---|---|
| E. coli strains | | |
| DH5α | Δ(lacZYA-argF)U169, hdsR17 relA1, supE44, endA1, recA1, thi gyrA96, φ80dlacZΔM15 | Life Technologies, Gaithersburg, MD |
| JM109 | endA1, recA1, gyrA96 thi, hdsR17 relA1, supE44, Δ(lac-proAB), mcrA, [F', traD36, proAB⁺, lacI$^q$ZΔM15] | C. Yanisch-Perron et al., Gene., 1985 33:103–119. |
| JM109(DE3) | endA1, recA1, gyrA96 thi, hdsR17 relA1, supE44, Δ(lac-proAB), mcrA, [F', traD36, proAB⁺, lacI$^q$ZΔM15], λ(DE3) | Promega Corp., Madison, Wis. |
| ES1301 mutS | Km$^r$, lacZ53, mutS201::Tn5, thyA36, rha-5, metB1, deoC, IN(rrnD–rrnE) | Promega Corp., Madison, Wis. |
| Plasmids | | |
| pDTG141 | Ap$^r$, nahAaAbAcAd (encoding the naphthalene dioxygenase components reductase$_{NAP}$, ferredoxin$_{NAP}$, and large and small subunits of the oxygenase, respectively) under the control of the T7 promoter of pT7-5 | W.-C. Suen, 1991. Ph.D. Thesis. The University of Iowa, Iowa City, IA. |
| pMASTER-1 | Tc$^r$, Ap$^s$, pALTER-1 carrying the KpnI-XbaI fragment of pDTG141 (nahAc'Ad) | R.E. Parales et al., *J. Bacteriol.* 1999, 181:1831–1837. |

[a]Km$^r$, kanamycin resistance; Ap$^r$, ampicillin resistance; Tc$^r$, tetracycline resistance Site-directed mutagenesis. Mutagenesis of nahAc was carried out with the Altered Sites II in vitro Mutagenesis System according to the manufacturer's instructions (Promega Corp., Madison, Wis.). Plasmid pMASTER-1 (R. E. Parales et al., *J. Bacteriol.*, 1999, 181, 1831–1837), which contains the 3' end of the nahAc gene and the complete nahAd gene (which encode the α and β subunits of NDO, respectively), was used as the template for mutagenesis. Each mutagenic oligonucleotide was designed with a silent mutation that altered the restriction pattern of the plasmid (Table 5) to facilitate screening for clones carrying the desired mutation. Phosphorylated oligonucleotides used for mutagenesis were synthesized by Genosys Biotechnologies Inc., Midland, Tex. The nucleotide sequences of both strands of the entire insertion in pMASTER-1 were determined for each mutant. Fluorescent automated DNA sequencing was carried out by the University of Iowa DNA Facility using an Applied Biosystems 373A automated DNA sequencer.

After verification of each mutation by restriction digestion and sequence analysis, the 1.5-kb KpnI-XbaI fragments carrying each mutation were individually cloned into KpnI-XbaI-digested pDTG141. After this subcloning step, the presence of each mutation was verified by restriction and sequence analyses. The resulting derivatives of pDTG141 were introduced into JM109(DE3) for expression studies and in this way each protein isoform was produced from an identical expression system.

Whole cell biotransformations. Induced *E. coli* cultures (50 ml) were supplemented with 20 mM glucose and 80 mM phosphate buffer (pH 7.2). Solid substrates (naphthalene, biphenyl, or phenanthrene) were added to a final concentration of 0.025% (w/v). Cultures were incubated at 30° C. with shaking (250 rpm) for 15–18 h. To obtain cells for large scale biotransformations to produce cis-biphenyl 3,4-dihydrodiol, JM109(DE3)(pDTG141-F352V) was grown at 27° C. in MSB containing glucose, thiamine, and ampicillin in a 10 L Biostat B fermentor (B. Braun Biotech International, Melsungen, Germany). Automated addition of NH$_4$OH was used to maintain the pH at 7.3, and a slow glucose feed rate was used to maintain the dissolved O$_2$ concentration at approximately 25% saturation.

Cultures were induced for 3 hours with 150 μM IPTG when the optical density of the culture (660 nm) reached approximately 0.7. Induced cultures (5.5 L) were incubated at 27° C. for 14–17 h with 0.025% (w/w) substrate (biphenyl or phenanthrene), high agitation (700 rpm), automated pH control (pH 7.5) and a slow glucose feed.

Indigo formation. JM109(DE3) strains carrying pDTG 141 derivatives with the various mutations were grown overnight at 37° C. on nitrocellulose filters placed on MSB agar plates containing 10 mM glucose, 1 mM thiamine, and 150 μg/ml ampicillin. Dried Whatman #1 filter papers that had been soaked in a 10% solution of indole dissolved in acetone were placed in the Petri dish covers after colony formation. Production of indigo from indole vapor by NDO was observed as colonies turned blue. No induction was carried out for these studies.

Separation and identification of products. Culture supernatants from whole cell biotransformation experiments were extracted with sodium hydroxide-washed ethyl acetate and analyzed by thin layer chromatography (TLC). Phenyl boronic acid (PBA) derivatives (A. B. Herbert, European Patent EP 0379300A2) were prepared as previously described (S. M. Resnick, D. T. Gibson, *Appl. Environ. Microbiol.* 1996, 62, 4073–4080). PBA-derivatized extracts were analyzed by gas chromatography-mass spectrometry (GC-MS) as previously described (S. M. Resnick, D. T. Gibson, *Appl. Environ. Microbiol.* 1996, 62, 3355–3359). cis-Naphthalene dihydrodiol was purified by preparative-layer chromatography (PLC) with chloroform-acetone (8:2) (S. M. Resnick, et al., *Appl. Environ. Microbiol.* 1994, 60, 3323–3328).

TABLE 5

Amino acid substitutions in the α subunit of NDO generated by site-directed mutagenesis

| Mutation | Mutagenic oligonucleotide[a] | Restriction site change | Indigo formation[b] |
|---|---|---|---|
| N201A | 5'-GAGGCACCCGCGG<u>AAGCTTT</u>TGTGGGAGATGCA-3' (SEQ ID NO:40) | HindIII | + |
| N201Q | 5'-GCACCCGCGG<u>AACAATT</u>TGTGGGAGATGCA-3' (SEQ ID NO:41) | Tsp509I | + |
| N201S | 5'-CCGCGGAA<u>AAGCTTT</u>GTGGGAG-3' (SEQ ID NO:42) | HindIII | ++ |
| F202L | 5'-CCGCGGAA<u>AAGCTT</u>GTGGGAGATG-3' (SEQ ID NO:43) | HindIII | – |
| F202V | 5'-CGCGGAA<u>AACGTT</u>GTGGGAGATG-3' (SEQ ID NO:44) | AclI | ++ |
| V260A | 5'-ATATTCAGG<u>TGCGC</u>ATAGCGCAG-3' (SEQ ID NO:45) | FspI | ++ |
| V260L | 5'-GGACGGATATTCA<u>GGGCTCC</u>ATAGCGCAGACTTG-3' (SEQ ID NO:46) | BanII | ++ |
| V260N | 5'-GACGGATATTCA<u>GGTAACC</u>ATAGCGCAGACTTG-3' (SEQ ID NO:47) | BstEII | ++ |
| W316A | 5'-GGTGTTTTCAAAG<u>TCGCG</u>AACCCGATCGAC-3' (SEQ ID NO:48) | NruI | +++ |
| T351N | 5'-CTGTTCAGCG<u>AAACTT</u>CGGGCCTGCT-3' (SEQ ID NO:49) | remove AclI | ++ |
| T351R | 5'-CTGTTCAGCG<u>AAGGTT</u>CGGGCCTGCT-3' (SEQ ID NO:50) | remove AclI | + |
| T351S | 5'-CTGTTCAGCG<u>AAGCTT</u>CGGGCCTGCT-3' (SEQ ID NO:51) | HindIII | +++ |
| F352L | 5'-TTCAGCG<u>AACGCT</u>CGGGCCTGC-3' (SEQ ID NO:52) | remove AclI | ++ |
| F352V | 5'-TTCAGCG<u>AACGGT</u>CGGGCCTGC-3' (SEQ ID NO:37) | remove AclI | + |
| W358A | 5'-GGCCTGCTGGCTTCGCGGAAAGCGACGACA-3' (SEQ ID NO:53) | none | – |
| D362A | 5'-GAAAGC<u>GACGCC</u>AATGACAAT-3' (SEQ ID NO:54) | BsaHI | – |
| M366W | 5'-ACGACAATGA<u>CAATT</u>GGGAAACAGCTTCGC-3' (SEQ ID NO:55) | MfeI | ++ |

[a]Underlined bases indicate the position of the introduced or eliminated restriction site. Base changes are in bold.
[b]Indigo formation was monitored after 8 h as described in Materials and Methods.
+++, colonies dark blue (corresponds to JM109(DE3)(pDTG141), expressing wild-type NDO;
++, colonies medium blue;
+, colonies pale blue;
–, no blue color (corresponds to negative control, JM109(DE3)(pT7-5).
[c]Colonies pale blue after 12 h.

Regioisomers of biphenyl dihydrodiol were separated by PLC (1.0 or 2.0 mm thickness; E. Merck Industries, Inc., Gibbstown, N.J.) using multiple elution (3–4 developments) with chloroform-acetone (9:1). cis-Biphenyl 3,4-dihydrodiol was also purified by radial-dispersion chromatography (RDC) using a Chromatotron (Harrison Research, Palo Also, Calif.). Extracts in chloroform containing 0. 1% triethylamine were applied to 2.0 mm-thick silica plates and eluted at a flow rate of 7 ml/min with a chloroform-acetone step gradient (0 to 15% acetone in 3% steps over. 1 h; 0.1% triethylamine was present at each step). Fractions (8 ml) were analyzed by TLC, and those containing cis-biphenyl 3,4-dihydrodiol were combined and concentrated at 35° C. under reduced pressure.

Chiral stationary-phase HPLC was used to resolve the enantiomers of cis-naphthalene dihydrodiol. A Chiralcel OJ column (Chiral Technologies, Exton, Pa.) was used as described previously (S. M. Resnick, et al., *Appl. Environ. Microbiol.* 1994, 60, 3323–3328). Under these conditions, the (+)-(1R,2S)- and (−)-(1S,2R)-enantiomers of cis-naphthalene dihydrodiol eluted with retention times of 30 and 33 minutes, respectively. Proton ($^1$H) nuclear magnetic resonance (NMR) spectra were acquired on the Varian UNITY-500 500 MHz spectrometer in the College of Medicine NMR Facility at the University of Iowa. All spectra were obtained using an 8 second relaxation delay, a 5 second acquisition time, a spectral width of 12 ppm and a 90 degree pulse width of 6.6 microseconds. Samples were prepared as described by S. M. Resnick, et al., *Appl. Environ. Microbiol.* 1994, 60, 3323–3328). Optical rotations were determined at 25° C. using a Jasco P1020 polarimeter with a 589 nm Na lamp. The results are the average of rotations given by three independently purified cis-biphenyl 3,4-dihydrodiol samples. High resolution mass spectra were recorded (by Dr. Lynn Teesch, HR-MS facility, The University of Iowa) on a VG ZAB-HF mass spectrometer equipped with direct inlet probe. Absorbance spectra (200 to 350 nm) were recorded on a Beckman DU-70 spectrophotometer.

Chemicals. Naphthalene was obtained from Fisher Scientific Co., Pittsburg, Pa. Indole, biphenyl, phenanthrene, and 4-hydroxybiphenyl were purchased from Aldrich Chemical Co., Milwaukee, Wis. Synthetic (+/−)-cis-naphthalene dihydrodiol and homochiral (+)-cis-naphthalene dihydrodiol were prepared as previously described (A. H. Jaffrey et al., *J. Org. Chem.*, 1974, 39, 1405–1407; S. M. Resnick and D. T. Gibson, *Biodegredations*, 1993, 4, 195–203). Synthetic cis-phenanthrene 9,10-dihydrodiol was provided by Dr. Derek Boyd.

Construction and preliminary analysis of modified NDO proteins. Nine positions near the active site in the a subunit of NDO were chosen for site-directed mutagenesis. Based on the crystal structure of NDO, Asn-201, Phe-202, Val-260, Trp-316, Phe-352, Trp-358 and Met-366 are located near enough to the mononuclear iron to interact with substrates in the active site. Asn-201 is positioned too far from the iron atom to be a ligand in the crystallized form of NDO, but was suggested as a possible ligand during some stage of the catalytic cycle. According to the NDO structure, Asp-362 is one of three amino acids that coordinate the iron at the active site. Asp-362 was replaced by alanine in order to disrupt iron coordination. Amino acid substitutions were also made at Thr-35 1, since the corresponding amino acid has be shown to be critical in determining polychlorinated biphenyl (PCB) congener specificity in biphenyl dioxygenase.

Site-directed mutations made in the a subunit of NDO are shown in Table 5. In most cases, small hydrophobic amino acids (alanine, valine, and leucine) were substituted for larger hydrophobic amino acids such as phenylalanine and tryptophan in order to change the size and/or shape of the active site pocket. In some cases, amino acid substitutions were chosen based on alignments of various related dioxygenase sequences.

Indigo formation was used as an initial screen for NDO activity. Freshly grown cells of JM109(DE3) carrying modified pDTG141 plasmids were incubated in the presence of indole. Most strains carrying mutant NDO enzymes formed blue colonies in the presence of indole. Strains producing NDO isoforms F202L and D362A formed white colonies, suggesting that either these enzymes were inactive or that indole was not a substrate for the modified enzymes. The strain carrying the W358A substitution in NDO formed pale blue colonies upon extended incubation with indole, indicating very weak activity with indole as substrate.

Production of mutant NDO α subunits. Formation of mutant α subunits was verified in Western blots using whole-cell protein samples from induced JM109(DE3) carrying modified pDTG141 plasmids. A monoclonal antibody specific for the a subunit of NDO was used R. E. Parales, et al., *J. Bacteriol.*, 1998, 180, 2337–2344). Results show that all mutant constructs formed full length α subunits and there were minor variations in the amounts of each mutant protein produced. More importantly, these show results demonstrate that the inability of isoforms D362A and F202L to produce products was not due to the absence of protein.

Biotransformations with naphthalene as substrate. Wild-type NDO converts naphthalene to cis-naphthalene 1,2-dihydrodiol. Biotransformations with naphthalene resulted in the formation of cis-naphthalene 1,2-dihydrodiol by all NDO isoforms with the exception of F202L and D362A, which formed no product. W358A transformations were very inefficient, with less than 5% of the substrate transformed within 15 h as judged by GC-MS analysis of extracted culture supernatants. The wild-type and all mutant NDO enzymes formed enantiomerically pure (>99%) (+)-(1R,2S)-cis-naphthalene dihydrodiol except for those with amino acid substitutions at Phe-352. Isoforms F352V and F352L formed 92% and 96% (+)-(1R,2S)-cis-naphthalene dihydrodiol, respectively. This result show the importance of a specific amino acid, Phe-352, in determining the enantioselectivity of NDO.

Biotransformations with biphenyl as substrate. Wild-type NDO oxidized biphenyl to two metabolites which were detected by TLC. The major metabolite ($R_f$, 0.2) and the minor metabolite ($R_f$, 0.18) dehydrated to phenolic products ($M^+$, 170) when analyzed by GC-MS. These results suggested that both metabolites were dihydrodiol isomers and this was confirmed by GC-MS of their stable respective phenyl boronic acid derivatives which gave molecular ions at m/e 274. The major metabolite (87% relative yield) had a retention time of 13.8 min and was identical to cis-2,3-dihydroxy-1-phenylcyclohexa4,6-diene (cis-biphenyl 2,3-dihydrodiol) produced from biphenyl by *Sphingomonas yanoikuyae* B8/36 (formerly Beijerinckia sp. strain B8/36) (D. T. Gibson et al., *Biochem. Biophys. Res. Commun.* 1973, 50, 211–219). The minor product (13% relative yield) had a retention time of 14.2 min and was identified as cis-3,4-dihydroxy-1-phenylcyclohexa-1,5-diene (cis-biphenyl 3,4-dihydrodiol; see below).

Isoforms F202L and D362A formed no products from biphenyl. isoforms N201A and W358A formed only a trace amounts of cis-biphenyl 2,3-dihydrodiol. Amino acid substitutions at N201, F202, V260, W316, and T351 had slight effects on the regiospecificity of NDO as seen by the product distributions shown in FIG. 1. However, both NDO isoforms with changes at position 352 formed cis-biphenyl 3,4-dihydrodiol as the major product. The isoform with the largest specificity change, F352V, formed 96% cis-biphenyl 3,4-dihydrodiol.

Identification and characterization of cis-biphenyl 3,4-dihydrodiol. The second product ran slightly slower than cis-biphenyl 2,3-dihydrodiol on TLC plates and, when analyzed by GC-MS as its PBA derivative, had a retention time of 14.2 min compared to 13.8 min for the PBA derivative of cis-biphenyl 2,3-dihydrodiol. The products formed from biphenyl by the F352V isoform were isolated by RDC. Approximately 140 mg of crude extract was applied to a 2.0 mm-thick silica chromatotron plate and eluted as described in the Materials and Methods to allow isolation of 40–60 mg pure cis-biphenyl 3,4-dihydrodiol and 1–2 mg of cis-biphenyl 2,3-dihydrodiol (fractions eluting before the 3,4-diol). The 3,4-regiochemistry of the diol and $^1$H NMR shift assignments were established by chemical shift multiplicities and independent H—H decoupling experiments. The 3,4-regiochemistry of the dihydrodiol was apparent by decoupling at H-3 (4.31 ppm) which reduced the multiplicity of the H-2 signal (ddd, 6.16) to a singlet with fine splitting. Acid dehydration resulted in the formation of a product that coeluted with authentic 4-hydroxybiphenyl in TLC and GC-MS analyses.

Physical characteristics of the cis-biphenyl 3,4-dihydrodiol were as follows: $\lambda_{max}$ [MeOH], 204, 228, and 276 nm, $\epsilon_{204}$=11,860, $\epsilon_{228}$=18,580, and $\epsilon_{276}$=4,336 $M^{-1}cm^{-1}$; calculated mass for the phenylboronate derivative, $^{12}C_{18}{}^1H_{15}{}^{16}O_2{}^{11}B$, 274.1160, found mass 274.1165; mass spectrum of phenyl boronate derivative m/z (relative intensity), 174 ($M^+$, 100), 170 (55), 152 (11), 142 (84), 115 (22), 77 (6); $[\alpha]_D$ –37.5±4.4, n=3 (c 0.5, MeOH); $^1$H NMR (chloroform), δ 4.21 (ddd, J=6.4, 4.0, 1.5 Hz, H-4), 4.31 (dd, J=6.4, 4.2 Hz, H-3), 6.09 (ddd, J=9.8, 4.0, 0.8 Hz, H-5), 6.16 (ddd, J=4.2, 1.7, 0.7 Hz, H-2), 6.37 (dt, J=9.9, 1.6 Hz, H-6), 7.30 (tt, 1H aromatic-p), 7.37 (m, 2H, aromatic-m), 7.46 (m, 2H, aromatic-o).

Figure 2:
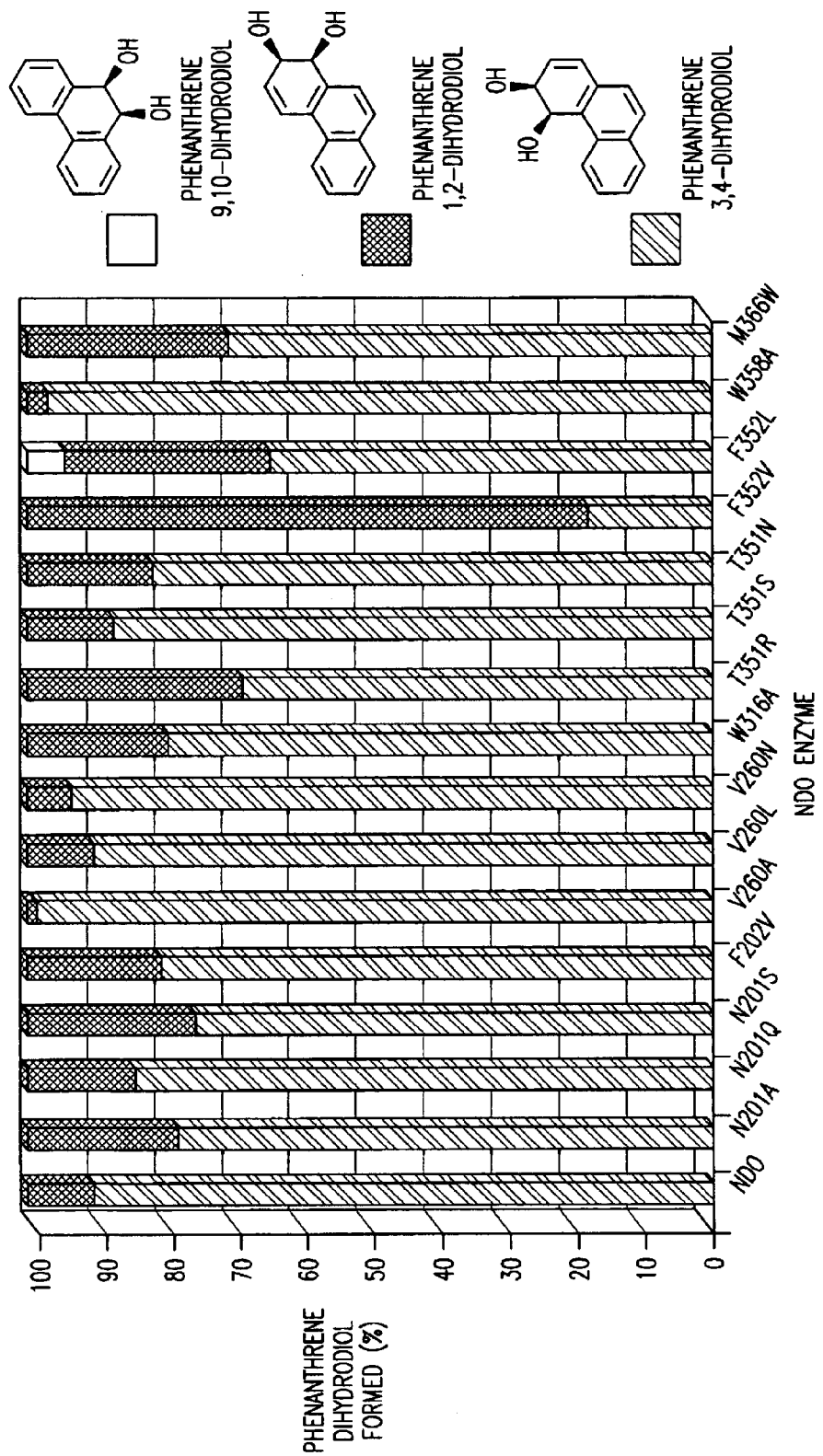
FIG. 2 illustrates the effect of specific amino acid substitutions in an alpha-subunit having SEQ ID NO: 26 on the regiospecificity of a naphthalene dioxygenase during the oxidation of phenanthrene.

Biotransformations with phenanthrene as substrate. Since many of the amino acid substitutions would be predicted to increase the size of the NDO active site, a larger substrate, phenanthrene, was tested. Identification of the three regioisomers of cis-phenanthrene dihydrodiol were carried out by comparing GC-MS data with cis-3,4-dihydroxy-3,4-dihydrophenanthrene (cis-phenanthrene 3,4-dihydrodiol) and cis-1,2-dihydroxy-1,2-dihydrophenanthrene (cis-phenanthrene 1,2-dihydrodiol) produced by *S. yanoikuyae* B8136 (D. M. Jerina et al., *J. Am. Chem. Soc.* 1976, 98, 5988–5996), and synthetic cis-9,10-dihydroxy-9,10- dihydrophenanthrene (cis-phenanthrene 9,10-dihydrodiol). The PBA derivatives of cis-phenanthrene 9,10-dihydrodiol, cis-phenanthrene 3,4-dihydrodiol and cis-phenanthrene 1,2-dihydrodiol had GC retention times of 18.0, 19.1, and 20.2 min, respectively. Wild-type NDO from Pseudomonas sp. strain NCIB 9816-4 formed a 9:1 mixture of cis-phenanthrene 3,4-dihydrodiol and cis-phenanthrene 1,2-dihydrodiol (FIG. 2). These results are similar to those obtained with NDO from Pseudomonas sp. strain 119 and biphenyl dioxygenase from *S. yanoikuyae* B8/36 (D. M. Jerina et al., *J. Am. Chem. Soc.* 1976, 98, 5988–5996).

With the exception of isoforms F202L and D362A, all mutant NDO enzymes formed products with phenanthrene as substrate. Amino acid substitutions at all positions changed product ratios to some extent. Isoforms V260A and W358A preferentially oxidized phenanthrene at the C3 and C4 positions, forming almost no cis-phenanthrene 1,2-dihydrodiol (FIG. 2). Several isoforms, including N201A, N201S, F202V, W316A, T351R, F352V, F352L, and M366W produced a significantly greater proportion of cis-phenanthrene 1,2-dihydrodiol than did wild-type NDO (FIG. 2). Of particular interest is the result with the F352V isoform. This enzyme had the opposite regioselectivity to wild-type NDO, forming 83% cis-phenanthrene 1,2-dihydrodiol in contrast to wild type, which formed 90% cis-phenanthrene 3,4-dihydrodiol. The F352L isoform oxidized phenanthrene to a small amount (5% of the total product) of cis-phenanthrene 9,10-dihydrodiol (FIG. 2).

Table 6 shows the amino acids in related dioxygenases that are located at positions corresponding to those mutated in NDO. Some amino acids listed in Table 6 are conserved in all of the enzymes shown (Phe-202 and Asp-362). In other cases, amino acids are not conserved and an amino acid in NDO was changed to one present in one of the other enzymes. Some of the NDO mutations were chosen based on the identification of amino acids critical for determining substrate specificity in other dioxygenases. In NDO, Thr-35 1, when changed to Asn, had a minor effect on product formation from phenanthrene. Replacement of this amino acid with Arg in NDO had a slight effect on product formation from biphenyl and a larger effect when phenanthrene was provided as the substrate (FIGS. 1 and 2). This position corresponds to the important amino acid in BPDO$_{LB400}$ Asn-377 that was mentioned above.

Changes at Val-260 in NDO resulted in minor changes in product formation with biphenyl and phenanthrene. Substitution of Val for Asn260 in 2NTDO resulted in an enzyme that no longer oxidized the aromatic ring of 2-nitrotoluene, forming only the monooxygenation product 2-nitrobenzylalcohol (J. V. Parales and D. T. Gibson, *Abstracts of the 99th General Meeting of the American Society for Microbiology*, 1999, Q-249, p-579). The opposite change in specificity did not occur with the NDO isoform V260N. Like wild-type NDO, the V260N isoform did not oxidize the aromatic ring of 2-nitrotoluene, but formed only 2-nitrobenzyl alcohol.

Toluene dioxygenase, which has a Trp residue at the position corresponding to 366 in NDO, dihydroxylates the aromatic ring of toluene to form cis-toluene dihydrodiol. However, the M366W isoform of NDO oxidized toluene to benzyl alcohol, the same product formed by the wild-type enzyme. Changing Trp-316 to Ala resulted in a minor change in regioselectivity with phenanthrene. Changing this conserved amino acid to Phe in 2NTDO had a slight effect on the stereochemistry of cis-naphthalene dihydrodiol formed from naphthalene (J. V. Parales and D. T. Gibson, *Abstracts of the 99th General Meeting of the American Society for Microbiology*, 1999, Q-249, p-579).

TABLE 6

Comparison of amino acids at the active sites of selected dioxygenase α subunits

| Position[b] | NDO$_{9816-4}$ | 2NTDO$_{JS42}$ | DNTDO$_{DNT}$ | TDO$_{F1}$ | BPDO$_{LB400}$ | BPDO$_{KF707}$ | NDO mutations |
|---|---|---|---|---|---|---|---|
| 201 | Asn | Asn | Asn | Gln | Gln | Gln | Ala, Gln, Ser |
| 202 | Phe | Phe | Phe | Phe | Phe | Phe | Leu, Val |
| 260 | Val | Asn | Val | Leu | Ser | Met | Ala, Leu, Asn |
| 316 | Trp | Trp | Phe | Trp | Trp | Trp | Ala |
| 351 | Thr | Ser | Ser | Thr | Asn | Thr | Asn, Arg, Ser |
| 352 | Phe | Ile | Thr | Phe | Phe | Phe | Leu, Val |
| 358 | Trp | Trp | Trp | Phe | Phe | Phe | Ala |
| 362 | Asp | Asp | Asp | Asp | Asp | Asp | Ala |
| 366 | Met | Met | Met | Trp | Trp | Trp | Trp |

[a]Enzymes: 2NTDO, 2-nitrotoluene dioxygenase from Pseudomonas sp. strain JS42 (49); DNTDO, 2,4-dinitrotoluene dioxygenase from Burkholderia sp. strain DNT (64); TDO, toluene dioxygenase from *Pseudomonas pudtida* F1 (67); BPDO$_{LB400}$, biphenyl dioxygenase from Burkholderia sp. strain LB400 (18); BPDO$_{KP707}$, biphenyl dioxygenase from *Pseudomonas pseudoalcaligenes* KF707 (K. Taira et al., J. Biol. Chem., 1992, 267:4844–4853.)
[b]Position numbers refer to NDO. Alignments were carried out with the Pileup program (Wisconsin Sequence Analysis Package: Genetics Computer Group, Madison, Wisc.) using a gap weight of 3.5 and a gap length of 0.1.

The amino acid at position 352 appears to play an important role in controlling both the stereochemistry of cis-naphthalene dihydrodiol formed from naphthalene, as well as the regioselectivity with substrates such as biphenyl and phenanthrene. In addition, a product that is not made by wild-type NDO, cis-phenanthrene 9,10-dihydrodiol, was formed from phenanthrene by the F352L isoform.

To compare substrate specificities of NDO and the new NDO isoforms with those of the closely related enzymes 2NTDO and DNTDO, biotransformations were carried out with biphenyl and phenanthrene. Both were found to be poor substrates for 2NTDO and DNTDO. Both enzymes made a trace amount of cis-biphenyl 2,3-dihydrodiol from biphenyl, and DNTDO made a trace amount of phenanthrene 3,4-dihydrodiol from phenanthrene. It is not clear at this time why biphenyl and phenanthrene are such poor substrates for 2NTDO and DNTDO.

In NDO, Asp-205 is located between the two redox centers at the junction of two adjacent a subunits. Substitution of Asp-205 by glutamine resulted in an isoform of NDO with no activity (R. E. Parales, et al. *J. Bacteriol.*, 1999, 181, 1831–1837). In the glutamine-containing enzyme, electron transfer between the Rieske center and the mononuclear iron was shown to be blocked, indicating that Asp-205 is essential for this electron transfer step to occur (R. E. Parales, et al. *J. Bacteriol.*, 1999, 181, 1831–1837). Iron at the active site of NDO is coordinated by His-208, His-213, and Asp-362. All three of these residues are conserved in the ring-hydroxylating dioxygenases whose sequences have been determined to date.

The corresponding histidine residues in toluene dioxygenase, from *P. putida* F1 (His-222 and His 228) were replaced with alanine residues and these substitutions resulted in completely inactive enzymes (H. Jiang, et al., *J. Bacteriol.* 19%, 178, 3133–3139). The inability to detect products from four different substrates indicates that substitution of Ala at position 362 results in an inactive form of NDO. No activity was detected in crude cell extracts of the D362A isoform with either oxygen uptake assays or product formation assays with $^{14}$C-naphthalene. These results are consistent with the identification of Asp-362 as a ligand to the mononuclear iron at the active site.

Asn-20 1, a possible fourth iron-coordinating amino acid was observed in the crystal structure of NDO. This residue was too far from the iron atom to serve as a ligand in the crystallized form of the enzyme, but was suggested as a possible ligand during a step in the catalytic cycle (B. Kauppi, et al., *Structure*, 1998, 6, 571–586). Amino acid substitutions at Asn-201 resulted in enzymes with reduced but significant activity, indicating that this residue does not participate in the coordination of iron at the active site. Crude cell extracts of the N201A and N201Q isoforms had 5–10% of the activity of wild-type NDO. Results presented in FIGS. 1 and 2 suggest that Asn-201 may play a minor role in determining regioselectivity with biphenyl and phenanthrene as substrates. However, Asn-201 may be more important for maintaining appropriate interactions between a subunits through its hydrogen bond with Tyr-103 near the Rieske center in an adjacent α subunit (B. Kauppi, et al., *Structure*, 1998, 6, 571–586). Substitution of an alanine at Asn-201 would disrupt this hydrogen bond and could affect the flow of electrons from the Rieske center to the mononuclear iron, thus reducing enzyme activity. The incorporation of the larger Gln residue at this position may prevent the normal interaction of α subunits even though Gln would be capable of forming a hydrogen bond with Tyr-103. The N201S isoform showed 35–40% of the wild-type NDO activity, indicating that serine is a reasonably good substitute for Asn at this position (B. V. Plapp, *Methods Enzymol.*, 1995, 249, 91–119).

Of the three substrates tested, the most significant effects of mutations at the active site were observed with the largest substrate, phenanthrene. This is not an unexpected result since the substrate pocket is of limited size and larger substrates are likely to come in contact with more amino acids in the active site. Many of the mutations involved the substitution of a small hydrophobic amino acid for a larger one, and in most cases this type of substitution did not severely reduce the activity of the enzyme as can sometimes occur (M. S. Caffrey, *Biochimie*, 1994, 76, 622–630). However, one exception was the substitution of Trp-358 by Ala, which resulted in an enzyme with very poor activity with naphthalene and biphenyl, but somewhat better activity with the larger substrate phenanthrene.

Another exception was isoform F202L, which failed to form products with all substrates tested. The reason that this substitution resulted in an inactive enzyme while isoform F202V had good activity is not understood. Somewhat surprisingly, mutations that introduced changes in polarity or charge (V260N, T351R) resulted in enzymes with good activity toward hydrophobic substrates. In general, most changes at the active site, with the exception of those that affect iron binding (Asp-362) and electron transfer (Asp-205) were tolerated well, suggesting that there is significant flexibility in the range of amino acids that can be introduced at the active site. This suggests that oxygenases with novel catalytic capabilities can be generated by introducing single or multiple mutations near the active site.

Example 7

Other Mutants Related to SEQ ID NO:25

Using procedures similar to those described in Example 1 (as described below), NDO mutant genes encoding glycine, alanine, threonine, leucine, isoleucine, tryptophane, or tyrosine instead of phenylalanine at position 352 were also prepared. Table 7 shows the SEQ ID No's for these DNA sequences and for proteins they encode.

TABLE 7

| Amino Acid At Position 352 | SEQ ID NO: For Modified Sequence | SEQ ID NO: For Corresponding Polypeptide |
|---|---|---|
| glycine | SEQ ID NO:27 | SEQ ID NO:32 |
| alanine | SEQ ID NO:28 | SEQ ID NO:33 |
| threonine | SEQ ID NO:29 | SEQ ID NO:34 |
| leucine | SEQ ID NO:30 | SEQ ID NO:35 |
| isoleucine | SEQ ID NO:31 | SEQ ID NO:36 |
| tyrptophane | SEQ ID NO:56 | SEQ ID NO:58 |
| tyrosine | SEQ ID NO:57 | SEQ ID NO:59 |

Activity of modified NDO proteins. The formation of indigo from indole was used to screen for NDO activity. Freshly grown colonies JM109(DE3) carrying modified pDTG141 plasmids were incubated in the presence of indole. Strains producing NDO enzymes with the mutations F352W and F352Y formed white colonies, suggesting that these enzymes were inactive or that indole was no longer a substrate for the modified enzymes. All other NDO isoforms constructed in this study appeared to be active. Table 8 shows the substitutions in the α subunit of NDO generated by site-directed mutagenesis.

TABLE 8

| Mutation | Mutagenic Oligonucleotide | SEQ ID NO: | Indigo Formation |
|---|---|---|---|
| F352G | 5'-GTTCAGCG<u>AACGGG</u>CGGGCCTGCTGG-3' | 60 | + |
| F352A | 5'-GTTCAGCG<u>AACGGC</u>CGGGCCTGCTGG-3' | 61 | + |
| F352T | 5'-GTTCAGCG<u>AACGAC</u>CGGGCCTGCTGG-3' | 62 | + |
| F352I | 5'-GTTCAGCG<u>AACGAT</u>CGGGCCTGCTGG-3' | 63 | + |
| F352L | 5'-TTCAGCG<u>AACGCT</u>CGGGCCTGC-3' | 52 | + |
| F352W | 5'-GTTCAGCG<u>AACGTG</u>GGGGCCTGCTGG-3' | 64 | – |
| F352Y | 5'-TTCAGCG<u>AACGTA</u>CGGGCCTGCTGG-3' | 65 | – |

Underlined bases in Table 8 indicate the position of the eliminated restriction site, AclI. BAase changes are in bold. Indigo formation was monitored after 8 hours; (+) indicates pale blue colonies, (–) indicates no blue color.

Regioselectivity of Modified NDO Proteins. Biotransformations with naphthalene resulted in the formation of cis-1,2-dihydroxy-1,2-dihydronaphthalene (cis-naphthalene dihydrodiol) by all NDO isoforms with substitutions at position 352 except F352Y, which formed no product. NDO-F352W transformations were very inefficient. In contrast to wild-type NDO, all enzymes with amino acid substitutions at position 352 formed small amounts of the (−)-enantiomer of cis-naphthalene dihydrodiol from naphthalene as determined from chiral HPLC analysis (Table 9).

TABLE 9

| NDO Enzyme | cis-Naphthalene 1,2-dihydrodiol | cis-Biphenyl 2,3-dihydrodiol | cis-Biphenyl 3,4-dihydrodiol |
|---|---|---|---|
| NDO (wild type) | >99% (+)-(1R,2S) | >95% (+)-(2R,3S) | >98% (+)-(3R,4S) |
| F352G | 98% (+)-(1R,2S) | >95% (+)-(2R,3S) | 60% (+)-(3R,4S) |
| F352A | 96% (+)-(1R,2S) | >95% (+)-(2R,3S) | 65% (+)-(3R,4S) |
| F352T | 93% (+)-(1R,2S) | >95% (+)-(2R,3S) | 60% (−)-(3S,4R) |
| F352V | 92% (+)-(1R,2S) | | 77% (−)-(3S,4R) |
| F352I | 94% (+)-(1R,2S) | >95% (+)-(2R,3S) | 53% (+)-(3R,4S) |
| F352L | 96% (+)-(1R,2S) | >95% (+)-(2R,3S) | 70% (+)-(3R,4S) |

When biphenyl was used as a biotransformation substrate, wild-type NDO converted it to an 87:13 mixture of cis-biphenyl 2,3-dihydrodiol and cis-biphenyl 3,4-dihydrodiol. However, a major change in regioselectivity with biphenyl was seen when amino acid substitutions were introduced at F352. All active mutant NDO enzymes with changes at this position formed cis-biphenyl 3,4-dihydrodiol as the major product (Table 10). The F352Y isoform formed no detectable product from biphenyl, and F352W formed only a trace amount of cis-biphenyl 2,3-dihydrodiol.

TABLE 10

| Enzyme | Biphenyl 2,3-diol | Biphenyl 3,4-diol | phenanthrene 3,4-diol | phenanthrene 1,2-diol | phenanthrene 9,10-diol |
|---|---|---|---|---|---|
| NDO | 87 | 13 | 90 | 10 | — |
| F352G | 32 | 68 | 79 | 21 | — |
| F352A | 23 | 77 | 53 | 47 | — |
| F352T | 8 | 92 | 59 | 41 | — |
| F352V | 4 | 96 | 17 | 83 | — |
| F352L | 15 | 85 | 64 | 31 | 5 |
| F352I | 17 | 83 | 76 | 24 | — |

Like wild-type NDO, isoforms F352G, F352A, F352T, F352I and F352L formed cis-phenanthrene 3,4-dihydrodiol as the major product from phenanthrene, although product ratios varied significantly depending on the enzyme (Table 10). The F352V isoform had the opposite regioselectivity, forming primarily (83%) cis-phenanthrene 1,2-dihydrodiol. Isoforms F352W and F352Y did not form detectable amounts of product from phenanthrene.

The enantiomeric composition of cis-biphenyl 2,3-dihydrodiol was unaffected by amino acid substitutions at this position, but that of the cis-biphenyl 3,4-dihydrodiol was significantly different in all cases from that formed by wild type (Table 9). Isoforms F352V and F352T formed the opposite enantiomer of cis-biphenyl 3,4-dihydrodiol as wild-type NDO (Table 9).

Absolute stereochemistry of cis-biphenyl 3,4-dihydrodiol. The formation of diastereomeric 2-(1-methoxyethyl)-phenyl boronic acid (MPBA) derivatives of the F352V-generated cis-biphenyl 3,4-dihydrodiol provided a means for determining the enantiomeric purity of the compound. The results also allow an empirical prediction of absolute configuration based on trends for vicinal cis-diols with a benzylic hydroxymethine (S. M. Resnick, et al., *J. Org. Chem.*, 1995, 60, 3546–3549). These trends were employed in the absence of MPBA directional shift data for a series of cis-3,4-dihydrodiols of known absolute configuration. Proton ($^1$H) nuclear magnetic resonance (NMR) spectra were acquired on the Bruker AMX-600 MHz NMR spectrometer at 600.14 MHz in the University of Iowa High-Field NMR Facility. All spectra were obtained using a 14 s recovery delay, a 4.06 s acquisition time, a spectral width of 13.4 ppm and a 90 degree pulse width of 7.5 $\mu$s. Samples were prepared as previously described (S. M. Resnick et al., *J. Org. Chem.*, 1995, 60, 3546–3549; S. M. Resnick et al., *Appl. Enviorn. Microbiol.*, 1994, 60, 3323–3328). $^1$H-NMR analysis ($d_6$-benzene) showed that the methoxy signal of the derivative formed with the (−)-cis-3,4-biphenyl dihydrodiol and (S)-MPBA was shifted downfield ($\Delta\delta$+21 ppb; 3.1987 ppm) relative to the corresponding signal of the (R)-MPBA derivative. The enantiomeric purity of the major diol was approximately 75%, based on integration of the methoxy groups of the major and minor MPBA diastereomers. This result confirms the data obtained by chiral HPLC analysis (Table 9). The downfield shifted methoxy signal for the (S)-MPBA derivative would indicate an S-configuration at the benzylic carbon for a 2,3-dihydrodiol. Application of this trend to the hydroxymethine nearest the benzylic position allows the suggestion of S-stereochemistry at C-3, and an absolute configuration of (−)-cis-(3S,4R)-biphenyl dihydrodiol.

Preparation of enantiomerically pure (−)-cis-(3S,4R)-biphenyl dihydrodiol. Three dihydrodiol dehydrogenases were tested for the ability to oxidize the (+)- and (−)-enantiomers of cis-biphenyl 2,3- and 3,4-dihydrodiols. Toluene dihydrodiol dehydrogenase from *Pseudomonas putida* F1 (J. E. Rogers and D. T. Gibson, *J. Bacteriol.*, 1977, 130, 1117–1124) was shown to specifically attack the (+)-enantiomers of both dihydrodiols at a significant rate. Plasmid pDTG511 carries the todD gene encoding toluene dihydrodiol dehydrogenase from *P. putida* F1 (G. J. Zylstra and D. T. Gibson Arromatic Hydrocarbon Degredation: a molecular approach, p. 183–203, in K. Setlow (ed.) Genetic Enginering: Principles and Methods, vol. 13, Plenum Press, New York). A bacterial strain was constructed which produces the F352V isoform of NDO and toluene dihydrodiol dehydrogenase. When this strain, JM109(DE3)(pDTG 141-F352V)(pDTG5 11), was used in biotransformations with biphenyl, the only dihydrodiol detected by chiral HPLC anaylsis was (−)-cis-biphenyl 3,4-dihydrodiol. The (+)-enantiomers of cis-biphenyl 2,3-dihydrodiol and cis-biphenyl 3,4-dihydrodiol were completely converted to the respective catechols, compounds which were easily separated from the dihydrodiol by preparative thin layer chromatography.

Absolute stereochemistry of cis-phenanthrene 3,4-dihydrodiol and 1,2-dihydrodiol. The formation of diastereomeric MPBA derivatives of the F352V-generated mixture of cis-phenanthrene dihydrodiols provided a means for determining the enantiomeric purity of the compounds. The results also allow an empirical prediction of absolute configuration based on trends for vicinal cis-diols with a benzylic hydroxymethine (S. M. Resnick et al., *J. Org. Chem.*, 1995, 60, 3546–3549). Samples were prepared as previously described (S. M. Resnick et al., *J. Org. Chem.*, 1995, 60, 3546–3549; S. M. Resnick et al., *Appl. Enviorn. Microbiol.*, 1994, 60, 3323–3328). Proton ($^1$H) nuclear magnetic resonance (NMR) spectra were acquired as described above. An upfield directional shift for the methoxy signal of many (S)-MPBA deriviatives of polyaromatic cis-1,2-dihydrodiols is indicative of an R-configuration at the benzylic position of the cis-diol. For the cis-phenanthrene 1,2-dihydrodiol, the methoxy signal of the (S)-MPBA deriviative was +72 ppb downfield from the corresponding signal of the opposite diastereomer formed with (R)-MPBA and predicting an S-configuration at the benzylic center.

Based on trends previously documented, the absolute configuration of the major dihydrodiol formed by F352V from phenanthrene is cis-(1S,2R)-phenanthrene dihydrodiol (91% e.e., approx. 83% relative yield). The facial selectivity in this case was the opposite to that shown for wild type biphenyl dioxygenase from *Sphingomonas yanoikuyae* B8/36. Analysis of the (±)-MPBA derivative of the isolated cis-phenanthrene dihydrodiol fraction formed by B8/36 showed resolution of the mixed racemates (of 3,4- and 1,2-diols) with minor methoxy signals of the 1,2-diol at 3.148 and 3.220 ppm. The same sample derivatized with (S)-MPBA showed the upfield shift for the methoxy signal at 3.148 ppm which corresponds to the an R-configuration of the benzylic center consistent with and confirmed by the previously determined (1R,2S)-configuration (M. Koreeda et al., *J. Org. Chem.*, 1978, 43, 1023–1027). The results of the above stereochemical correlation also suggest that the empirical application of the trends in the directional shifts of polycyclic aromatic diols appears to be valid for both the "bay-region" cis-3,4- and "non-bay region" cis-1,2-dihydrodiols of phenanthrene.

The minor diol formed from phenanthrene by F352V was identified as cis-(3S,4R)-phenanthrene dihydrodiol (>95% e.e., 17% relative yield). This assignment is based on the correlation of the methoxy signal at 3.115 ppm (but not 3.241 ppm) in the (S)-MPBA derivative of the F352V minor phenanthrene 3,4-dihydrodiol with that of the identical directional shifts of the known B8/36 cis-phenanthrene 3,4-dihydrodiol derivatives.

Relative activities of the mutant NDO enzymes. Cultures (50 ml in 500 ml flasks) were grown and induced, and biotransformations with naphthalene or biphenyl were initiated as described previously. Samples (1 ml each) were taken at 30 minute intervals over a period of 5 hours. Cells were removed by centrifugation and pellets were stored at −20° C. for protein determinations. cis-Naphthalene dihydrodiol formation was monitored at 262 nm ($\epsilon_-=8114$ $M^{-1}cm^{-1}$). cis-Biphenyl 2,3-dihydrodiol formation was monitored at 303 nm ($\epsilon_-=13,600$ $M^{-1}cm^{-1}$; (2)). cis-Biphenyl 3,4-dihydrodiol formation was monitored at 276 nm ($\epsilon_-=4340$ $M^{-1}cm^{-1}$; (5)) using a correction for the absorbance of cis-biphenyl 2,3-dihydrodiol at this wavelength. The extinction coefficient of cis-biphenyl 2,3-dihydrodiol at 276 nm (the λmax of of cis-biphenyl 3,4-dihydrodiol) was determined to be 7950 $M^{-1}cm^{-1}$ using purified cis-biphenyl 2,3-dihydrodiol from *S. yanoikuyae* B8/36 (2). The concentration of cis-biphenyl 3,4-dihydrodiol was calculated using the ratios of products formed by each mutant enzyme and subtracting the contribution of cis-biphenyl 2,3-dihydrodiol. Absorbance of the negative control strain (JM109(DE3)(pT7-5) was subtracted at each time point. Protein concentrations were determined by the method of Bradford (M. M. Bradford, *Anal. Biochem.* 1976, 72, 248–254) after boiling cell pellets for 1 h in 0.1 N NaOH. Bovine serum albumin was used as the standard. Rates reported are the averages of three independent experiments.

The in vivo rates of formation of cis-naphthalene dihydrodiol by wild-type and mutant NDO enzymes are shown in Table 11.

TABLE 11

| NDO Enzyme | Naphthalene dihydrodiol formation | | Biphenyl 2,3-dihydrodiol formmation | | Biphenyl 3,4dihydrodiol formation | |
|---|---|---|---|---|---|---|
| | Specific Activity (nmol/min/mg) | Relative Activity (%) | Specific Activity (nmol/min/mg) | Relative Activity (%) | Specific Activity (nmol/min/mg) | Relative Activity (%) |
| NDO | 20.4 | 100 | 4.81 | 100 | 0.95 | 100 |
| F352G | 7.4 | 37 | <0.05 | <1 | <0.25 | <26 |
| F352A | 9.9 | 49 | 0.07 | 1 | 0.25 | 26 |
| F352T | 15.6 | 77 | 0.14 | 3 | 0.73 | 77 |
| F352V | 16.9 | 83 | 0.15 | 3 | 0.94 | 99 |
| F352I | 16.5 | 81 | 0.16 | 3 | 0.74 | 78 |
| F352L | 19.5 | 96 | 0.21 | 4 | 0.82 | 86 |

The F352L isoform produced cis-naphthalene dihydrodiol at wild-type rates, while the F352T, F352V, and F352I isoforms were slightly less efficient, with rates 75–85% that of wild-type NDO. The F352G and F352A enzymes were the least efficient in catalyzing this reaction. A similar trend is seen in the rates of formation of cis-biphenyl 3,4-dihydrodiol from biphenyl by the enzymes with substitutions at postion 352 (Table 11). The F352T, V, I and L isoforms formed product at slightly reduced rates compared to wild-type NDO, while F352A was significantly slower and F352G rates were not measurable. In contrast, all enzymes with substitutions at position 352 were severely defective in forming cis-biphenyl 2,3-dihydrodiol from biphenyl (Table 11). These studies demonstrate that the amino acid substitutions at position 352 result in enzymes with a decreased tendency to oxidize at the 2,3-position of biphenyl. However, the rate of oxidation at the 3,4-position of biphenyl was not improved in the mutant enzymes.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A dioxygenase complex comprising a plurality of polypeptides, wherein the complex catalyzes the oxidation of an aromatic substrate and comprises at least one alpha-subunit polypeptide selected from the group consisting of:
   (a) a polypeptide comprising SEQ ID NO: 26 with a substituted amino acid at position 352 of SEQ ID NO: 26,
   (b) a polypeptide comprising SEQ ID NO: 26 with a substituted amino acid at position 201, 202, 260, 316, 351, 358, 362, or 366 of SEQ ID NO: 26,
   (c) a polypeptide comprising SEQ ID NO: 26 with a substituted amino acid at position 352 of SEQ ID NO: 26 and a substituted amino acid at position 201, 202, 260, 316, 351, 358, 362, or 366 of SEQ ID NO: 26,
   or a fragment of said dioxygenase complex that catalyzes oxidation of an aromatic substrate.

2. The dioxygenase complex of claim 1 having an alpha-subunit that comprises SEQ ID NO:26 with an amino acid other than phenylalanine at position 352 of SEQ ID NO: 26, or a fragment thereof that catalyzes oxidation of an aromatic substrate.

3. The dioxygenase complex of claim 1 having an alpha-subunit that comprises SEQ ID NO:26 with a substituted acid at position 201, 202, 260, 316, 351, 352, 358, 362, or 366 of SEQ ID NO: 26, or a fragment thereof that catalyzes oxidation.

4. The dioxygenase complex of claim 1 having an alpha-subunit that comprises a substituted amino acid at the position corresponding to position 352 of SEQ ID NO:26, and a substituted amino acid at the position corresponding to position 201, 202, 260, 316, 351, 358, 362, or 366 of SEQ ID NO: 26; or a fragment thereof that catalyzes oxidation of an aromatic substrate.

5. The dioxygenase complex of claim 2 wherein the amino acid at position 352 is a naturally occurring amino acid.

6. The dioxygenase complex of claim 2 wherein the alpha-subunit comprises SEQ ID NO:2, 32, 33, 34, 35, or 36.

7. The dioxygenase complex of claim 2 wherein the alpha-subunit comprises SEQ ID NO:2.

8. The dioxygenase complex of claim 3 having an alpha-subunit that comprises alanine, glutamine, or serine at position 201.

9. The dioxygenase complex of claim 3 having an alpha-subunit that comprises leucine or valine at position 202.

10. The dioxygenase complex of claim 3 having an alpha-subunit that comprises alanine, leucine, or asparagine at position 260.

11. The dioxygenase complex of claim 3 having an alpha-subunit that comprises alanine at position 316.

12. The dioxygenase complex of claim 3 having an alpha-subunit that comprises asparagine, arginine, or serine at position 351.

13. The dioxygenase complex of claim 3 having an alpha-subunit that comprises alanine at position 358.

14. The dioxygenase complex of claim 3 having an alpha-subunit that comprises alanine at position 362.

15. The dioxygenase complex of claim 3 having an alpha-subunit that comprises tryptophan at position 366.

* * * * *

UNITED STATES PATENT AND TRADEMARK OFFICE
CERTIFICATE OF CORRECTION

PATENT NO. : 6,794,167 B2
DATED : September 21, 2004
INVENTOR(S) : Parales et al.

It is certified that error appears in the above-identified patent and that said Letters Patent is hereby corrected as shown below:

Column 3,
Lines 54-57, delete "The invention also provides an isolated and purified DNA segment encoding a polypeptide of the invention, or a variant or fragment thereof." and insert the same as a new paragraph on line 55.

Column 7,
Line 45, delete "4dihydrobiphenyl" and insert -- 4-dihydrobiphenyl --, therefor.

Column 12,
Line 35, delete "coil" and insert -- coli. --, therefor.

Column 13,
Line 5, delete "3 pi" and insert -- 3 $\mu$I --, therefor.

Column 14,
Line 2, delete "$\beta$D-thiogalactopyranoside" and insert -- $\beta$-D-thiogalactopyranoside --, therefor.

Columns 19-20,
Line 7, in "Table 5" delete "CCGCGGAAAAGCTTTGTGGGAG" and insert -- CCGCGGAAAGCTTTGTGGGAG --, therefor.

Column 21,
Line 12, delete "Thr-35 1" and insert -- Thr-351 --, therefor.
Line 15, delete "a" and insert -- $\alpha$ --, therefor.

Column 22,
Line 5, delete "phenylcyclohexa4" and insert -- phenylcyclohexa-4 --, Columns 23-24,
Line 3, "Table 3", delete "pudtida" and insert -- putida --, therefor.

Column 25,
Line 23, delete "Asn-20 1" and insert -- Asn-201 --, therefor.

Column 26,
Line 57, in "Table 8" delete "F3521" and insert -- F352I --, therefor.

UNITED STATES PATENT AND TRADEMARK OFFICE
CERTIFICATE OF CORRECTION

PATENT NO. : 6,794,167 B2
DATED : September 21, 2004
INVENTOR(S) : Parales et al.

It is certified that error appears in the above-identified patent and that said Letters Patent is hereby corrected as shown below:

Column 27,
Line 48, delete "F3521" and insert -- F352I --, therefor.

Column 29,
Line 51, delete "Amax" and insert -- λmax --, therefor.

Column 30,
Line 32, delete "F3521" and insert -- F352I --, therefor.

Signed and Sealed this

Fifth Day of April, 2005

JON W. DUDAS
*Director of the United States Patent and Trademark Office*